US010899786B2

United States Patent
Cai et al.

(10) Patent No.: US 10,899,786 B2
(45) Date of Patent: Jan. 26, 2021

(54) NUCLEOSIDE PHOSPHATE COMPOUND AND PREPARATION METHOD AND USE THEREOF

(71) Applicant: SICHUAN KELUN-BIOTECH BIOPHARMACEUTICAL CO., LTD., Chengdu (CN)

(72) Inventors: Jiaqiang Cai, Chengdu (CN); Shuai Song, Chengdu (CN); Qiang Tian, Chengdu (CN); Yitao Zhang, Chengdu (CN); Haitao Huang, Chengdu (CN); Guoqing Zhong, Chengdu (CN); Wei Zhong, Chengdu (CN); Yongjia Hao, Chengdu (CN); Mingliang Zhao, Chengdu (CN); Hong Zeng, Chengdu (CN); Hongmei Song, Chengdu (CN); Xin Zhou, Chengdu (CN); Yao Liu, Chengdu (CN); Yuting Tan, Chengdu (CN); Lichun Wang, Chengdu (CN); Jingyi Wang, Chengdu (CN)

(73) Assignee: SICHUAN KELUN-BIOTECH BIOPHARMACEUTICAL CO., LTD., Sichuan (CN)

( * ) Notice: Subject to any disclaimer, the term of this patent is extended or adjusted under 35 U.S.C. 154(b) by 26 days.

(21) Appl. No.: 16/344,317

(22) PCT Filed: Dec. 19, 2017

(86) PCT No.: PCT/CN2017/117126
§ 371 (c)(1),
(2) Date: Apr. 23, 2019

(87) PCT Pub. No.: WO2018/113652
PCT Pub. Date: Jun. 28, 2018

(65) Prior Publication Data
US 2020/0308214 A1    Oct. 1, 2020

(30) Foreign Application Priority Data

Dec. 23, 2016 (CN) .......................... 2016 1 1204909
Jan. 24, 2017 (CN) .......................... 2017 1 0059345
Oct. 23, 2017 (CN) .......................... 2017 1 0991293

(51) Int. Cl.
*A01N 43/04*    (2006.01)
*A61K 31/70*    (2006.01)
*C07H 19/10*    (2006.01)
*A61P 1/16*    (2006.01)
*C07H 1/02*    (2006.01)

(52) U.S. Cl.
CPC ............... *C07H 19/10* (2013.01); *A61P 1/16* (2018.01); *C07H 1/02* (2013.01)

(58) Field of Classification Search
None
See application file for complete search history.

(56) References Cited

FOREIGN PATENT DOCUMENTS

| CN | 105504007 A | 4/2016 |
|---|---|---|
| WO | 2008/005555 A1 | 1/2008 |
| WO | 2010/075549 A2 | 7/2010 |
| WO | 2011/130557 A2 | 10/2011 |
| WO | 2012/117246 A1 | 9/2012 |
| WO | 2013/025788 A1 | 2/2013 |
| WO | 2014/076490 A1 | 5/2014 |
| WO | WO 2014/143643 A1 | 9/2014 |
| WO | 2015/013352 A2 | 1/2015 |
| WO | WO 2016/044281 A1 | 3/2016 |

OTHER PUBLICATIONS

Intellectual Property Office of Singapore; Written Opinion in Singapore Appl. No. 11201903593S; dated Mar. 23, 2020; 6 pgs.
Chapman et al., "Purification of Pmpa Amidate Prodrugs by Smb Chromatography and X-Ray Crystallography of the Diastereomerically Pure Gs-7340", Nucleosides, Nucleotides & Nucleic Acids, 20(4-7), 1085-1090 (2001), 7 pages.
Krecmerova, et al., "New prodrugs of two pyrimidine acyclic nucleoside phosphonates: Synthesis and antiviral activity", Elsevier, Bioorganic & Medicinal Chemistry 25 (2017) 4637-4648, 12 pages.
Kwong et al., "Recent progress in the development of selected hepatitis C virus NS3•4A protease and NS5B polymerase inhibitors", Elsevier, Current Opinion in Pharmacology 2008, 8:522-531, 10 pages.
Shi et al., "Acquired Resistance of Pancreatic Cancer Cells towards 5-Fluorouracil and Gemcitabine is Associated with Altered Expression of Apoptosis-Regulating Genes", Oncology 2002;62:354-362, 9 pages.
Simmonds, Peter, "Genetic diversity and evolution of hepatitis C virus—15 years on", Journal of General Virology (2004), 85, 3173-3188, 16 pages.
Sofia, et al.., "Discovery of a β-D-2'-Deoxy-2'-α-fluoro-2'-β-C-methyluridine Nucleotide Prodrug (PSI-7977) for the Treatment of Hepatitis C Virus", J. Med. Chem. 2010, 53, 7202-7218, 17 pages.
Zeuzem et al., "Expert opinion on the treatment of patients with chronic hepatitis C", Journal of Viral Hepatitis, 2009, 16, 75-90, 16 pages.
State Intellectual Property Office of the P.R. China; International Search Report; PCT/CN2017/117126, dated Mar. 28, 2018.
European Patent Office; Extended European Search Report for App. No. 17882690.5; dated Aug. 3, 2020.

*Primary Examiner* — Patrick T Lewis
(74) *Attorney, Agent, or Firm* — Kilpatrick Townsend & Stockton LLP

(57) ABSTRACT

Provided in the present invention are a compound of Formula (I), a pharmaceutical composition comprising the same, a method for preparing the same, and use thereof as a NS5B polymerase inhibitor, a DNA polymerase inhibitor or a reverse transcriptase inhibitor for the prevention or treatment of viral diseases or cancers.

28 Claims, No Drawings

US 10,899,786 B2

NUCLEOSIDE PHOSPHATE COMPOUND AND PREPARATION METHOD AND USE THEREOF

CROSS-REFERENCE TO RELATED APPLICATIONS

The present application is a National Phase Entry of PCT/CN2017/117126, filed Dec. 19, 2017, which claims the benefit of priority of Chinese Patent Application No. 201611204909.4, filed on Dec. 23, 2016, Chinese Patent Application No. 201710059345.8, filed on Jan. 24, 2017, and Chinese Patent Application No. 201710991298.8, filed on Oct. 23, 2017, the contents of which are incorporated herein by reference in their entirety.

FIELD OF THE INVENTION

The present invention relates to a nucleoside phosphate compound, a pharmaceutical composition comprising the same, a process for the preparation thereof, and use thereof as a nonstructural protein 5B (NS5B) polymerase inhibitor, a DNA polymerase inhibitor or a reverse transcriptase inhibitor for the prevention or treatment of a viral disease or cancer.

BACKGROUND OF THE INVENTION

A virus consists of a nucleic acid (DNA or RNA) and protein, or consists of protein only (e.g., prion). A virus can cause a variety of infectious diseases. Common diseases caused by a virus include, but are not limited to, viral hepatitis type A, viral hepatitis type B, viral hepatitis type C, influenza, herpes and acquired immunodeficiency syndrome (AIDS).

Antiviral drugs, presently used in clinic, including RNA and DNA polymerase inhibitors, reverse transcriptase inhibitors, interferons and the like, function by inhibiting viral attachment, uncoating, viral gene duplication, maturation or release, or by affecting the host's immune system.

Hepatitis C virus (HCV) is a positive-sense single-stranded RNA (ssRNA) virus and belongs to the genus of Hepatitis virus, and the Flaviviridae family. Based on the gene encoding NS5B ribonucleic acid-dependent ribonucleic acid polymerase, hepatitis C virus is classified into 6 genotypes with 50 subtypes. The genotypes are distributed differently across the world. In North America and Europe, genotypes 1, 2 and 3 have been found, predominately genotype 1. In Africa, almost only patients with genotype 4 and genotype 5 infections are found. The common genotypes in China are 1b and 2a, predominately 1b, and genotype 6 is found the predominate type in Hong Kong and Macao (Simmonds, P. Journal of General Virology, 2004, 85, 3173-3188). Among them, genotype 1b is found in patients of cirrhosis and liver cancer significantly more frequently than in patients of chronic hepatitis. HCV genotype 1b is a marker for more severe HCV-associated liver disease, with earlier recurrence and more severe hepatitis than liver disease caused by other genotypes. The incidence of hepatitis B coinfection is high in genotypes 1a and 2a, and most (74%) patients of acute hepatitis are of genotype 1a. Genotype 4 infection tends to cause decompensated liver complications. Genotype 3a infection is closely related to fatty liver.

The standard therapeutic regimen in the prior art is peginterferon plus ribavirin. However, this regimen is only effective in 40-50% of genotype 1 patients and 75% of genotypes 2 and 3 patients (Zeuzem, S., et al., Journal of Viral Hepatitis, 2009, 16, 75-90). For some sub-populations, peginterferon plus ribavirin is not quite effective. Therefore, there is an urgent need to develop safe and effective "direct-acting antiviral drugs". The first generation of hepatitis C virus protease inhibitors, telaprevir and boceprevir, came out in succession. These two drugs, when combined with peginterferon/ribavirin, can improve the viral clearance rate and shorten the course of treatment in genotype 1 patients. However, this new triple combination therapy brings new problems, such as more side effects, complicated dosing regimens, more drug resistance, and it is only effective in patients infected by genotype 1 virus (Kwong, A. D. et al., Current Opinion in Pharmacology, 2008, 8, 522-531). The new "direct-acting antiviral drugs" need to meet three requirements: (1) capability of oral administration; (2) effectiveness for all genotypes; and (3) no need to be combined with peginterferon and ribavirin.

The HCV virion is a spherical positive stranded ssRNA virus with a genome of about 9600 nucleotides, encoding a polyprotein consisting of 3010 amino acids. The genome sequence thereof is: CE1E2/NS1NS2NS3NS4ANS4BNS5ANS5B. The HCV viral polyprotein is cleaved by host cellular and the viral proteases into individual viral proteins including three structural proteins (i.e., structural protein C, structural protein E1, and structural protein E2/NS1) and four non-structural proteins (i.e., non-structural protein NS2, non-structural protein NS3, non-structural protein NS4, and non-structural protein NS5). Among them, structural protein E1 and structural protein E2/NS1 are glycoproteins, which can produce a neutralizing effect against HCV. Non-structural protein NS provides a catalytic structure for viral replication. At present, the function of non-structural protein NS2 and non-structural protein NS4 has not been known yet. Non-structural protein NS3 has helicase activity, and is involved in the unwinding of HCV-RNA molecules, which in turn release NS5B. NS5B is an RNA-dependent RNA polymerase (i.e., HCV NS5B polymerase) that is involved in the reaction in the HCV replication cycle, in which reaction dsRNA is synthesized from a viral ssRNA as template. Therefore, if a compound can effectively inhibit HCV NS5B polymerase, it can block HCV dsRNA synthesis, and effectively control HCV virus infection.

A nucleoside analogue cannot inhibit viral polymerase unless it is converted to a nucleoside triphosphate. This process requires the participation of three different kinases. The efficiency of phosphorylation determines the activity of a nucleoside analogue as a viral polymerase inhibitor. In addition, the activity of the inhibitor also depends on the time of existence of the nucleoside triphosphate. The longer time the nucleoside triphosphate exists, the higher the activity of the inhibitor. In the process of phosphorylation, the nucleoside analogue and monophosphate and diphosphate metabolites thereof may not be good substrates for the corresponding kinases. Studies have shown that the first kinase is most selective for the substrate in the process of phosphorylation. Therefore, the first phosphorylation step is usually the most difficult one. In order to overcome this difficulty, delivery of monophosphate into cells is a necessary means. However, nucleoside monophosphates are negatively charged. It is difficult for them to pass through the cell membrane, and they are prone to be degraded by phosphatases.

Sofosbuvir is a HCV NS5B polymerase inhibitor. It is a uracil nucleotide analogue having a nucleoside phosphoramidate structure. This structure provides this type of drugs with good cell penetration and plasma stability. Sofosbuvir can be metabolized by hepatocytes into the active compound of a uridine triphosphate analogue. The analogue competes with intracellular uridine triphosphate for insertion into the newly generated nucleotide chain, leading to premature termination of the RNA chain elongation, and achieving the inhibition of RNA polymerase (Journal of Medicinal Chemistry, 2010, 53, 7202-7218).

The production amount and the duration of existence of the nucleoside triphosphate in liver directly affects the inhibitory effect on viral polymerase NS5B. Sofosbuvir is less effective for patients with hepatitis C genotype 3 infection, and a 24-week course of treatment is needed; and even for patients with genotypes 1, 2 and 4 infections, the course of treatment is still 12 weeks. Therefore, invention of a more effective novel nucleoside phosphate derivative has great significance and application value.

Hepatitis B virus, a DNA virus, belongs to the Hepadnaviridae family. The DNA synthesis thereof relies on hepatitis B virus DNA polymerase. The use of DNA polymerase inhibitors as anti-HBV drugs has become a very competitive option. Tenofovir (PMPA) is a nucleotide DNA polymerase and a reverse transcriptase inhibitor, and has anti-HBV and HIV activity. The phosphoramidate derivative thereof, tenofovir alafenamide (TAF), has been approved by the FDA for the treatment of human immunodeficiency syndrome and viral hepatitis type B. TAF produces an adenosine triphosphate analogue in hepatocytes by esterase hydrolysis, phosphorylation and the like, which inserts newly generated DNA strands, thereby blocking DNA polymerase-catalyzed DNA synthesis and inhibiting viral replication (WO2013025788A1; Nucleosides Nucleotides Nucleic Acids, 2001, 20, 1085-1090). Nucleoside anticancer drugs produce nucleoside triphosphates through the metabolic process of phosphorylation in the body, and the latter insert DNA strands, inhibiting DNA synthesis, preventing progression of cells from G1 to S phase, and causing G1 phase arrest in tumor cells, thereby inhibiting the malignant proliferation of tumor cells (Oncology, 2002, 62(4), 354-362).

In summary, many nucleoside drugs play an active role in antiviral and anticancer fields, and the key point is that these drugs, as nucleoside analogues, are absorbed and metabolized by cells in the body, and prevent RNA or DNA synthesis in virus and tumor cells. Among them, the nucleoside triphosphate analogues, as metabolites in the body, are important active ingredients, and the production rate, concentration and retention time thereof determine the efficacy.

SUMMARY OF THE INVENTION

In one aspect, the present invention provides a nucleoside phosphate compound, a pharmaceutically acceptable salt, ester, solvate, isomer thereof, any crystalline form or racemate of the foregoing, a metabolite form of the foregoing, or a mixture of the foregoing. The compound is metabolized by liver tissue to produce a large amount of nucleoside triphosphate metabolites, and is rapidly converted to a nucleoside triphosphate metabolite. Therefore, the nucleoside phosphate compound of the present invention (hereinafter also referred to as "the compound of the invention") are useful as an NS5B polymerase inhibitor, a DNA polymerase inhibitor or a reverse transcriptase inhibitor, for example, for the treatment of diseases, e.g. a viral disease such as viral hepatitis type C (HCV), viral hepatitis type B (HBV), viral hepatitis type A (HAV), influenza, herpes, and acquired immunodeficiency syndrome (AIDS), or cancer. The compound of the invention can be efficiently metabolized in vivo to be converted to active nucleoside triphosphate metabolites. Compared with the existing (HCV) NS5B polymerase inhibitors, hepatitis B virus DNA polymerase inhibitors, and retroviral reverse transcriptase inhibitors, the compound of the invention can be converted to a nucleoside triphosphate metabolite more efficiently, and thus has superior activity.

Specifically, the compound of the invention is represented by Formula (I):

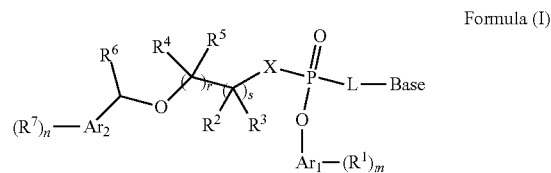

Formula (I)

wherein

L is selected from the group consisting of substituted or unsubstituted $C_{1-12}$ alkylene, $C_{2-12}$ alkenylene, $C_{2-12}$ alkynylene, and the alkylene, alkenylene or alkynylene is optionally interrupted by one or more —O—, —NR$^8$— or —S—; or L represents a group of Formula (c), Formula (d) or Formula (e), wherein $=\!=\!=$ represents a single bond or a double bond, position 1 is attached to the Base, and position 2 is attached to the phosphorus atom (P):

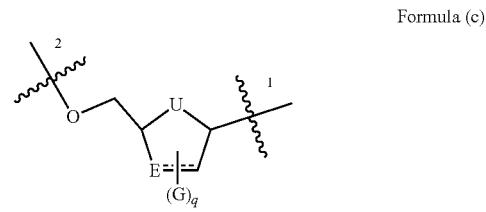

Formula (c)

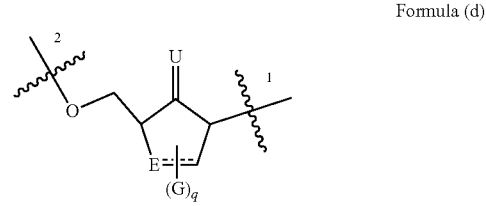

Formula (d)

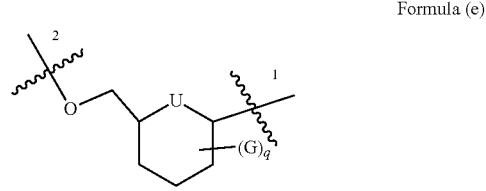

Formula (e)

Base represents a group of Formula (a) or Formula (b):

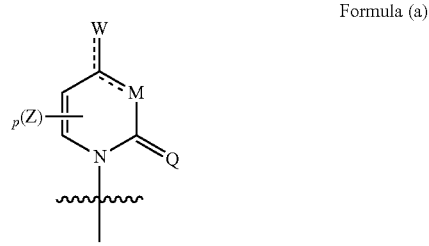

Formula (a)

-continued

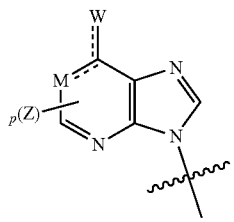

Formula (b)

⚌ represents a single bond or a double bond;
M represents N or NR$^8$;
W represents H, NR$^8$R$^9$, NR$^8$, CH$_2$, O or S;
Q represents O, S, NR$^8$ or CH$_2$;
each Z, at each occurrence, independently represents hydrogen, halogen, hydroxy, cyano, nitro, azido, NR$^8$R$^9$, substituted or unsubstituted C$_{1-6}$ alkyl, substituted or unsubstituted C$_{1-6}$ alkoxy, or substituted or unsubstituted C$_{3-8}$ cycloalkyl, and if there are multiple Z groups, they each may be the same or different;
p represents 0, 1, 2, 3, 4 or 5;
provided that when M is attached by a double bond, W is attached by a single bond; and when M is attached by a single bond, W is attached by a double bond;
U represents O, S, NR$^8$ or CR$^{10}$R$^{11}$;
E represents CR$^{10}$, CR$^{10}$R$^{11}$ or S, provided that when E is attached by a double bond, it is CR$^{10}$;
each G, at each occurrence, independently represents hydrogen, halogen, hydroxyl, cyano, nitro, azido, NR$^8$R$^9$, substituted or unsubstituted C$_{1-6}$ alkyl, substituted or unsubstituted C$_{1-6}$ alkoxy, or substituted or unsubstituted C$_{3-8}$ cycloalkyl, and if there are multiple G groups, they each may be the same or different;
q represents an integer from 0 to 5;
Ar$_1$ represents C$_{6-14}$ aryl or 5- to 14-membered heteroaryl;
each R$^1$, at each occurrence, represents hydrogen, halogen, —OH, —CN, —NO$_2$, —NR$^8$R$^9$, substituted or unsubstituted C$_{1-6}$ alkyl, substituted or unsubstituted C$_{1-6}$ alkoxy, substituted or unsubstituted C$_{1-6}$ haloalkyl, substituted or unsubstituted C$_{1-6}$ alkylthio, substituted or unsubstituted C$_{3-8}$ cycloalkyl, substituted or unsubstituted 3- to 10-membered heterocycloalkyl, substituted or unsubstituted C$_{2-10}$ alkenyl, or substituted or unsubstituted C$_{2-10}$ alkynyl, and if there are multiple R' groups, they each may be the same or different;
m represents an integer from 0 to 7;
X represents CH$_2$, —S—, —O— or —NR$^8$—;
R$^2$ and R$^3$, at each occurrence, each independently represent hydrogen, substituted or unsubstituted C$_{1-6}$ alkyl, substituted or unsubstituted C$_{1-6}$ alkoxy, substituted or unsubstituted C$_{6-14}$ aryl, substituted or unsubstituted C$_{7-20}$ aralkyl, or substituted or unsubstituted C$_{3-8}$ cycloalkyl; or R$^2$ and R$^3$ together with the carbon atom to which they are attached, form substituted or unsubstituted C$_{3-8}$ cycloalkyl, or substituted or unsubstituted 3- to 10-membered heterocycloalkyl;
R$^4$ and R$^5$, at each occurrence, each independently represent hydrogen, substituted or unsubstituted C$_{1-6}$ alkyl, substituted or unsubstituted C$_{1-6}$ alkoxy, substituted or unsubstituted C$_{6-14}$ aryl, substituted or unsubstituted C$_{7-20}$ aralkyl, or substituted or unsubstituted C$_{3-8}$ cycloalkyl group; or R$^4$ and R$^5$ together with the carbon atom to which they are attached, form substituted or unsubstituted C$_{3-8}$ cycloalkyl, or substituted or unsubstituted 3- to 10-membered heterocycloalkyl; or
R$^3$ and R$^4$ are linked to each other, together with the carbon atoms to which they each are attached, form substituted or unsubstituted C$_{3-8}$ cycloalkyl, or substituted or unsubstituted 3- to 10-membered heterocycloalkyl;
R$^6$ represents hydrogen, substituted or unsubstituted C$_{1-6}$ alkyl, substituted or unsubstituted C$_{3-8}$ cycloalkyl, substituted or unsubstituted C$_{6-14}$ aryl group, substituted or unsubstituted C$_{7-20}$ aralkyl, or substituted or unsubstituted C$_{1-6}$ alkoxy;
each R$^2$, at each occurrence, independently represents hydrogen, halogen, —OH, —CN, —NO$_2$, —NR$^8$R$^9$, substituted or unsubstituted C$_{1-6}$ alkyl, substituted or unsubstituted C$_{1-6}$ haloalkyl, substituted or unsubstituted C$_{1-6}$ alkylthio, substituted or unsubstituted C$_{3-8}$ cycloalkyl, substituted or unsubstituted 3- to 10-membered heterocycloalkyl, substituted or unsubstituted C$_{2-10}$ alkynyl, or substituted or unsubstituted C$_{1-6}$ alkoxy, and if there are multiple R$^7$ groups, they each may be the same or different; or
R$^6$ and R$^7$ are linked to each other, together with the carbon atoms therebetween, form substituted or unsubstituted C$_{3-8}$ carbocyclyl or 3- to 10-membered heterocyclyl;
n represents an integer of from 0 to 7;
Ar$_2$ represents C$_{6-14}$ aryl or 5- to 14-membered heteroaryl;
r and s each independently represent 1, 2 or 3;
R$^8$ and R$^9$, at each occurrence, each independently represent hydrogen, substituted or unsubstituted C$_{1-6}$ alkyl, or substituted or unsubstituted C$_{3-8}$ cycloalkyl, if there are multiple R$^8$ and R$^9$ groups, they each may be the same or different; and
R$^{10}$ and R$^{11}$, at each occurrence, each independently represent hydrogen, substituted or unsubstituted C$_{1-6}$ alkyl, or substituted or unsubstituted C$_{3-8}$ cycloalkyl, or R$^{10}$ and R$^{11}$ together form C$_{1-6}$ alkylene, and if there are multiple R$^{10}$ and R$^{11}$ groups, they each may be the same or different.

In another aspect, the present invention provides a pharmaceutical composition comprising the compound of the invention, a pharmaceutically acceptable salt, ester, solvate, isomer thereof, any crystalline form or racemate of the foregoing, a metabolite form of the foregoing, or a mixture of the foregoing, wherein the pharmaceutical composition is in the form of a solid formulation, a semisolid formulation, a liquid formulation, or a gaseous formulation.

In another aspect, the present invention provides use of the compound of the invention, a pharmaceutically acceptable salt, ester, solvate, isomer thereof, any crystalline form or racemate of the foregoing, a metabolite form of the foregoing, or a mixture of the foregoing, or the pharmaceutical composition of the invention in the manufacture of a medicament for the prevention or treatment of a NS5B polymerase mediated disease, a DNA polymerase mediated disease or a reverse transcriptase mediated disease.

In another aspect, the present invention provides use of the compound of the invention, a pharmaceutically acceptable salt, ester, solvate, isomer thereof, any crystalline form or racemate of the foregoing, a metabolite form of the foregoing, or a mixture of the foregoing, or the pharmaceutical composition of the invention in the manufacture of a medicament for the prevention or treatment of a viral disease or cancer.

In another aspect, the present invention provides the compound of the invention, a pharmaceutically acceptable salt, ester, solvate, isomer thereof, any crystalline form or racemate of the foregoing, a metabolite form of the foregoing, or a mixture of the foregoing, or the pharmaceutical composition of the invention for use in the prevention or treatment of a NS5B polymerase mediated disease, a DNA polymerase mediated disease or a reverse transcriptase mediated disease.

In another aspect, the present invention provides the compound represented by Formula (I) of the invention, a pharmaceutically acceptable salt, ester, solvate, isomer thereof, any crystalline form or racemate of the foregoing, a metabolite form of the foregoing, or a mixture of the foregoing, or the pharmaceutical composition of the invention for use in the prevention or treatment of a viral disease or cancer.

In another aspect, the present invention provides a method for preventing or treating a NS5B polymerase mediated disease, a DNA polymerase mediated disease or a reverse transcriptase mediated disease, comprising administering to a subject in need thereof an effective amount of the compound of the invention, a pharmaceutically acceptable salt, ester, solvate, isomer thereof, any crystalline form or racemate of the foregoing, a metabolite form of the foregoing, or a mixture of the foregoing, or the pharmaceutical composition of the invention.

In another aspect, the present invention provides a method for preventing or treating a viral disease or cancer, comprising administering to a subject in need thereof an effective amount of the compound of the invention, a pharmaceutically acceptable salt, ester, solvate, isomer thereof, any crystalline form or racemate of the foregoing, a metabolite form of the foregoing, or a mixture of the foregoing, or the pharmaceutical composition of the invention.

In another aspect, the present invention provides a method for preparing the compound of the invention, comprising the following steps:

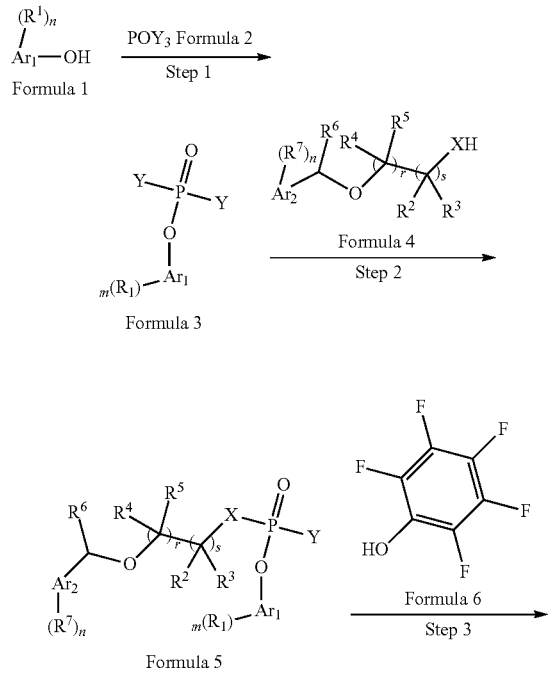

Step 1: reacting a phosphorus oxyhalide of Formula 2 with a compound of Formula 1 to obtain a compound of Formula 3;

Step 2: reacting the compound of Formula 3 with a compound of Formula 4 to obtain a compound of Formula 5;

Step 3: reacting the compound of Formula 5 with pentafluorophenol of Formula 6 to obtain a compound of Formula 7; and Step 4: reacting the compound of Formula 7 with a compound of Formula 8 to obtain a compound of Formula (1);

wherein $R^1$, $R^2$, $R^3$, $R^4$, $R^5$, $R^6$, $R^7$, m, n, s, r, X, $Ar_1$, $Ar_2$, L and Base are as defined above; and each Y is the same or different, and is each independently selected from halogen;

or

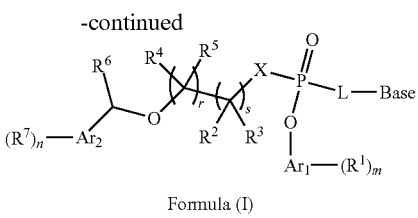

Formula (I)

wherein $R^1$, $R^2$, $R^3$, $R^4$, $R^5$, $R^6$, $R^7$, m, n, s, r, X, $Ar_1$, $Ar_2$, L and Base are as defined above;

or

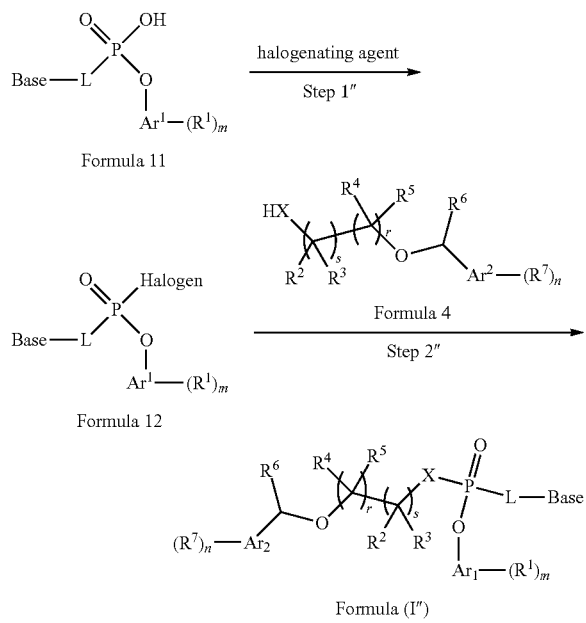

The method in Scheme 3 is a method for synthesizing a chirally pure phosphorus compound (I″), wherein ⁓ represents either a solid wedge (▬) or dashed wedge (⋯) chemical bond; and
$R^1$, $R^2$, $R^3$, $R^4$, $R^5$, $R^6$, $R^7$, m, n, s, r, X, $Ar_1$, $Ar_2$, L and Base are as defined above.

DETAILED DESCRIPTION OF THE INVENTION

Definition

Unless otherwise defined below, all the technical and scientific terms used herein are intended to have the same meaning commonly understood by those skilled in the art. References to techniques used herein are intended to refer to techniques commonly understood in the art, including those variations or replacements of equivalent techniques that are obvious to those skilled in the art. While it is believed that the following terms are well understood by those skilled in the art, the following definitions are set forth for better explaining the invention.

In the present invention, combinations of substituents and variables are only allowed where such combinations can bring about chemically stable compounds. Where a substituent per se is substituted by two or more groups, these multiple groups may exist on the same carbon or different carbons as long as it leads to a stable structure.

The terms "including", "comprising", "having", "containing", or "relating to" and other variants thereof, as used herein, are inclusive or open-ended, and not exclusive of other elements or steps of methods that are not enumerated.

In the present invention, the subscripted numeral of a carbon atom "C" represents the number of carbon atoms. For example, $C_1$ represents 1 carbon atom, $C_2$ represents 2 carbon atoms, and $C_{p-q}$ represents p-q (0<p<q) carbon atoms. The group name after the carbon atom "C" indicates the kind of the group. For example, $C_1$ alkyl represents methyl, $C_2$ alkenyl represents ethenyl, and $C_{p-q}$ alkyl represents alkyl having a carbon number of p-q.

The term "halo" or "halogen", as used herein, means fluoro, chloro, bromo or iodo.

The term "$C_{1-6}$ alkyl", as used herein, means a linear or branched aliphatic saturated hydrocarbyl group having 1 to 6 carbon atoms, and examples thereof include methyl, ethyl, n-propyl, isopropyl, n-butyl, isobutyl, sec-butyl, tert-butyl, n-pentyl, isopentyl, neopentyl, n-hexyl, isohexyl and the like. Alkyl having 1 to 4 carbon atoms (i.e., $C_{1-4}$ alkyl) is preferred, and examples thereof include methyl, ethyl, n-propyl, isopropyl, n-butyl, isobutyl, sec-butyl and the like.

The term "$C_{1-6}$ alkoxy", as used herein, means a linear or branched aliphatic saturated hydrocarbyloxy group in which the alkyl moiety is the above-mentioned "$C_{1-6}$ alkyl", and examples thereof include methoxy, ethoxy, propoxy, isopropoxy, butoxy, isobutoxy, pentyloxy, isopentyloxy, hexyloxy and the like. $C_{1-4}$ alkoxy is preferred.

The term "$C_{1-6}$ alkylene", as used herein, means a divalent radical formed by the loss of one hydrogen atom from each of two different carbon atoms of a linear or branched "$C_{1-6}$ alkane". Examples thereof include methylene (—$CH_2$—), ethylene (dimethylene, —$CH_2CH_2$—), propylene (trimethylene, —$CH_2CH_2CH_2$—), butylene (tetramethylene, —$CH_2CH_2CH_2CH_2$—), isobutylene (—$CH_2CH(CH_3)CH_2$—) and the like. Among them, $C_{1-4}$ alkylene is preferred, and $C_{1-3}$ alkylene is more preferred.

The term "$C_{1-6}$ alkylidene", as used herein, means a divalent radical formed by the loss of two hydrogen atoms from a same carbon atom of a linear or branched "$C_{1-6}$ alkane". Examples thereof include methylidene ($CH_2$=), ethylidene ($CH_3CH$=), propylidene ($CH_3CH_2CH$=), butylidene ($CH_3CH_2CH_2CH$=) and the like. Among them, $C_{1-4}$ alkylidene is preferred, and $C_{1-3}$ alkylidene is more preferred.

The term "$C_{2-10}$ alkenyl", as used herein, means a linear or branched aliphatic hydrocarbyl group having 2 to 10 carbon atoms and having one or more unsaturated double bonds, and examples thereof include ethenyl, 1-propenyl, 2-propenyl, 2-methyl-1-propenyl, 2-methyl-2-propenyl, 2-buten-1-yl, 3-buten-1-yl, 2-penten-1-yl, 3-penten-1-yl, 4-penten-1-yl, 5-hexen-1-yl, 4-hexen-1-yl, 3-hexene-1-yl, 2-hexen-1-yl, 3-methyl-2-buten-1-yl, 3-methyl-3-penten-1-yl, 3-methyl-2-pentene-1-yl, 4-methyl-3-penten-1-yl, 4-methyl-2-penten-1-yl, 2-methyl-2-penten-1-yl and the like. It is preferred to have one double bond. $C_{2-6}$ alkenyl is preferred.

The term "$C_{2-10}$ alkynyl", as used herein, means a straight or branched aliphatic hydrocarbyl group having 2 to 10 carbon atoms and having one or more unsaturated triple bonds, and examples thereof include ethynyl, 1-propyn-1-yl, 2-propyn-1-yl, 2-butyn-1-yl, 3-butyn-1-yl, 2-pentyn-1-yl, 3-pentyn-1-yl, 4-pentyn-1-yl, 5-hexyn-1-yl, 4-hexyn-1-yl, 3-hexyn-1-yl, 2-hexyn-1-yl and the like. It is preferred to have one triple bond. $C_{2-6}$ alkynyl is preferred.

The term "$C_{3-8}$ cycloalkyl", as used herein, means a cyclic aliphatic hydrocarbyl group having 3 to 8 carbon atoms, and examples thereof include cyclopropyl, cyclobutyl, cyclopentyl, a cyclohexyl, cycloheptyl and the like. $C_{3-4}$ cycloalkyl is preferred, and examples thereof include cyclopropyl or cyclobutyl. Correspondingly, "$C_{4-8}$ cycloalkyl" means a cycloalkyl group having 4 to 8 carbon atoms. In some cases, the cycloalkyl can be fused to aryl or heteroaryl.

The term "$C_{3-8}$ heterocycloalkyl", as used herein, means a group further comprising at least one heteroatom selected from the group consisting of N, O and S in the ring of the above "$C_{3-8}$ cycloalkyl", and examples thereof include oxetanyl, azetidinyl, thietanyl, tetrahydrofuranyl, pyrrolidinyl, imidazolidinyl, dioxanyl, piperidinyl, piperazinyl, tetrahydropyranyl and the like. It is preferred to have one heteroatom selected from the group consisting of N, O and S in the $C_{3-8}$ cycloalkyl. $C_{3-6}$ heterocycloalkyl is preferred. Correspondingly, "$C_{4-8}$ heterocycloalkyl" means a heterocycloalkyl group having 4 to 8 carbon atoms. The term "3- to 10-membered heterocycloalkyl" means a heterocycloalkyl group having 3 to 10 ring atoms (including at least one heteroatom selected from the group consisting of N, O and S); and the term "4- to 10-membered heterocycloalkyl" means a heterocycloalkyl group having 4 to 10 ring atoms (including at least one heteroatom selected from the group consisting of N, O and S). In some cases, the heterocycloalkyl is fused to aryl or heteroaryl.

The term "aralkyl", as used herein, denotes an aryl-substituted alkyl group, wherein the aryl and the alkyl are as defined herein. Typically, the aryl can have 6 to 14 carbon atoms, and the alkyl can have 1 to 6 carbon atoms. Exemplary aralkyl groups include, but are not limited to, benzyl, phenylethyl, phenylpropyl, phenylbutyl and the like.

The term "alkylthio", as used herein, means an alkyl group as defined above that is attached to the parent molecular moiety through a sulfur atom. Representative examples of $C_{1-6}$ alkylthio include, but are not limited to, methylthio, ethylthio, tert-butylthio, hexylthio and the like.

The term "$C_{4-8}$ carbocyclyl", as used herein, means a cyclic group having 4 to 8 carbon atoms, which may be a saturated ring or an unsaturated ring. In the case of a saturated ring, it corresponds to a cycloalkyl group having 4 to 8 carbon atoms. Unsaturated rings may include $C_{4-8}$ cycloalkenyl which is a cyclic hydrocarbyl group having 4 to 8 carbon atoms and having at least one unsaturated double bond in the ring, and examples thereof include cyclopentenyl, cyclohexenyl, cycloheptenyl, cyclooctenyl and the like; $C_{4-8}$ cycloalkynyl which is a cyclic hydrocarbyl group having 4 to 8 carbon atoms and having at least one unsaturated triple bond in the ring, and examples thereof include cyclohexynyl, cycloheptynyl and the like; and also an aromatic $C_{4-8}$ carbocyclyl group such as phenyl.

The term "$C_{4-8}$ heterocyclyl", as used herein, means a group further comprising at least one heteroatom selected from the group consisting of N, O and S in the ring of the above $C_{4-8}$ carbocyclyl, and it may be a saturated or unsaturated ring. In the case of a saturated ring, it corresponds to a heterocycloalkyl group having 4 to 8 carbon atoms. In the case of an unsaturated ring, it is a group having at least one unsaturated double bond and/or unsaturated triple bond at any position of the above heterocycloalkyl having 4 to 8 carbon atoms, and examples thereof include imidazolinyl, isooxazolinyl, pyrrolyl, pyrazolyl, pyrazolinyl, imidazolyl, oxazolyl, isoxazolyl, thiazolyl, thiadiazolyl, isothiazolyl, furyl, thienyl, oxadiazolyl, pyridyl, pyrazinyl, pyrimidinyl, pyridazinyl, triazinyl and the like.

The term "$C_{6-10}$ aryl", as used herein, means a monocyclic or bicyclic aromatic hydrocarbyl group having 6 to 8 carbon atoms, such as phenyl, 1-naphthyl, 2-naphthyl and the like.

The term "$C_{3-10}$ heteroaryl", as used herein, means an aromatic 5- or 6-membered monocyclic or 9- or 10-membered bicyclic group having from 3 to 10 carbon atoms and containing at least one heteroatom selected from the group consisting of N, O and S in at least one ring, and the ring containing heteroatom(s) preferably has 1, 2 or 3 heteroatoms selected from the group consisting of O, S and N. Each heteroatom-containing ring of the heteroaryl may contain 1 or 2 oxygen or sulfur atoms and/or 1 to 4 nitrogen atoms, provided that the total number of heteroatoms in each ring is 4 or less, and each ring contains at least one carbon atom. The nitrogen and sulfur atoms can be optionally oxidized, and the nitrogen atom can optionally be quaternized. Examples of monocyclic heteroaryl include pyrrolyl, pyrazolyl, pyrazolinyl, imidazolyl, oxazolyl, isoxazolyl, thiazolyl, isothiazolyl, furyl, thienyl, pyridyl, pyrazinyl, pyrimidinyl, pyridazinyl, triazinyl and the like. Examples of bicyclic heteroaryl include indolyl, benzothiazolyl, benzodioxolyl, benzoxazolyl, benzothienyl, quinolyl, tetrahydroisoquinolyl, isoquinolyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolyl and the like. The term "5- to 6-membered heteroaryl" means a heteroaryl group having 5 or 6 ring atoms (including at least one heteroatom selected from the group consisting of N, O and S), and examples thereof include pyrrolyl, pyrazolyl, pyrazolinyl, imidazolyl, oxazolyl, isoxazolyl, thiazolyl, isothiazolyl, furyl, thienyl, pyridyl, pyrazinyl, pyrimidinyl, pyridazinyl, triazinyl and the like. The term "5- to 14-membered heteroaryl" means a heteroaryl group having 5 to 14 ring atoms (including at least one heteroatom selected from the group consisting of N, O and S).

In the present invention, the substituent of the above "$C_{1-6}$ alkyl", "$C_{1-6}$ alkoxy", "$C_{1-6}$ alkylene", "$C_{1-6}$ alkylidene", "$C_{2-10}$ alkenyl", "$C_{2-10}$ alkynyl", "$C_{3-8}$ cycloalkyl", "$C_{3-8}$ heterocycloalkyl", "$C_{4-8}$ carbocyclyl", "$C_{4-8}$ heterocyclyl", "$C_{6-10}$ aryl" and "$C_{3-10}$ heteroaryl" can be, for example, one or more same or different groups selected from the group consisting of cyano, hydroxyl, carboxyl, halo (F, Cl, Br, I), $C_{1-6}$ alkyl, $C_{1-6}$ haloalkyl, $C_{1-6}$ haloalkoxy (e.g., $CF_3O$), $C_{3-6}$ cycloalkyl (e.g., cyclopropyl), $C_{1-6}$ alkoxy (e.g., methoxy, ethoxy, propoxy, butoxy and the like), $C_{2-10}$ alkenyloxy (e.g., ethenyloxy, allyloxy and the like), $C_{1-6}$ alkoxycarbonyl (e.g., methoxycarbonyl, ethoxycarbonyl, tert-butoxycarbonyl and the like, nitro, nitroso, azido, amino, aminocarbonylamino, $C_{1-6}$ alkylaminocarbonylamino, aminocarbonyl $C_{1-6}$ alkyl, $C_{1-6}$ alkyl aminocarbonyl $C_{1-6}$ alkyl, aminocarbonyloxy, amino $C_{1-6}$ alkoxycarbonyl, $C_{1-6}$ alkoxycarbonylamino, $C_{1-6}$ alkoxy $C_{1-6}$ alkylamino, $C_{2-10}$ alkenyl $C_{2-10}$ alkynyl, $C_{1-6}$ alkylamino (e.g., methylamino, ethylamino, dimethylamino and the like), acylamino (e.g., acetylamino, benzoylamino and the like), $C_{6-10}$ arylalkylamino (e.g., benzylamino, tritylamino), hydroxyamino, $C_{1-6}$ alkylsulfonylamino (e.g., methylsulfonylamino), $C_{1-6}$ alkylsulfinylamino (e.g., methylsulfinylamino), imino, hydroxyimino, $C_{1-6}$ alkylimino (e.g., methylimino, ethylimino, dimethylimino and the like), $C_{1-6}$ alkoxyimino (e.g., methoxyimino, ethoxyimino and the like), acylimino (e.g., acetylimino, benzoylimino and the like), azido, $C_{6-10}$ aryl (e.g., phenyl and the like), $C_{6-10}$ aryl $C_{1-6}$ alkyl (e.g., benzyl, phenylethyl and the like), $C_{6-10}$ aryl $C_{1-6}$ alkoxy (e.g., benzyloxy), $C_{1-6}$ alkylcarbonyloxy, $C_{4-8}$ heterocyclyl (including aliphatic heterocyclyl and heteroaryl), non-aromatic $C_{4-8}$ heterocyclyl (e.g., pyrrolinyl, piperidinyl, piperazinyl, pyrrolidinyl, morpholinyl, morpholino and the like), $C_{3-10}$ heteroaryl (e.g., furyl, thienyl, pyridyl, isoxazolyl, thiazolyl, thiadiazolyl, oxazolyl, oxadiazolyl, tetrazolyl, indolyl, benzofuranyl and the like), $C_{3-10}$ heteroaryl $C_{1-6}$ alkyl (pyridylmethyl, pyridylethyl and the like), cyano, isocyano, isocyanato, thiocyanato, isothiocyanato, mercapto, $C_{1-6}$ alkylthio (e.g., methylthio and the like), $C_{1-6}$ alkylsulfonyl (e.g., methylsulfonyl, ethylsulfonyl), $C_{1-6}$ alkylsulfinyl, aminocarbonyl, $C_{1-6}$ alkylaminocarbonyl (e.g., methylaminocarbonyl, ethylaminocarbonyl, dimethylaminocarbonyl and the like), sulfamoyl, alkylaminocarbonylalkylsulfamoyl, acyl (e.g., formyl, acetyl and the like), formyloxy, thioformyl, thiocarboxy, dithiocarboxy, thiocarbamoyl, sulfinyl, sulfo, hydrazino, azido, ureido, amidino, guanidino, phthalimido, tri-$C_{1-6}$ alkylsilyl (trimethylsilyl and the like), oxo and the like. The above substituent is preferably selected from the group consisting of halo, cyano, nitro, carboxyl, hydroxy, amino, aminocarbonyl, azido, $C_{1-6}$ alkyl, $C_{3-6}$ cycloalkyl, $C_{1-6}$ alkoxy, $C_{1-6}$ alkoxycarbonyl, $C_{1-6}$ alkylthio, $C_{1-6}$ alkylsulfinyl, $C_{1-6}$ alkylsulfonyl, $C_{1-6}$ alkylsulfamoyl, $C_{1-6}$ alkylsulfonylamino, $C_{1-6}$ alkylamino, $C_{1-6}$ alkylcarbonyloxy, $C_{1-6}$ alkylaminocarbonyl, aminocarbonylamino, $C_{1-6}$ alkylaminocarbonylamino, aminocarbonyl $C_{1-6}$ alkyl, $C_{1-6}$ alkylaminocarbonyl $C_{1-6}$ alkyl, aminocarbonyloxy, amino $C_{1-6}$ alkoxycarbonyl, $C_{1-6}$ alkoxycarbonylamino, $C_{1-6}$ alkoxy $C_{1-6}$ alkylamino, $C_{2-10}$ alkenyl, $C_{2-10}$ alkyne, $C_{6-10}$ aryl and $C_{4-8}$ heterocyclyl (including aliphatic heterocyclyl and heteroaryl); and particularly preferably selected from the group consisting of hydroxyl, halo, azido, methyl, ethyl, propyl, butyl, halomethyl, haloethyl, halopropyl, halobutyl, carboxyl, cyano and nitro.

Unless otherwise indicated, as used herein, a substituent can be attached at any suitable position thereof.

When a bond of a substituent is shown to pass through a bond connecting two atoms in a ring, such substituent can bond to any of the ring-forming atoms in the substitutable ring.

The invention also contemplates all pharmaceutically acceptable isotopically-labeled compounds, which are identical to the compounds of the invention except that one or more atoms are replaced by the atom(s) of the same atomic number but having atomic mass or mass number different from the atomic mass or mass number prevailing in nature. Examples of isotopes suitable for inclusion in the compounds of the invention include, but are not limited to, isotopes of hydrogen (e.g., $^2H$ and $^3H$, preferably $^2H$); isotopes of carbon (e.g., $^{11}C$, $^{13}C$ and $^{14}C$); isotopes of chlorine (e.g., $^{36}Cl$); isotopes of fluorine (e.g., $^{18}F$); isotopes of iodine (e.g., $^{123}I$ and $^{125}I$); isotopes of nitrogen (e.g., $^{13}N$ and $^{15}N$); isotopes of oxygen (e.g., $^{15}O$, $^{17}O$ and $^{18}O$); isotopes of phosphorus (e.g., $^{32}P$); and isotopes of sulfur (e.g., $^{35}S$). Certain isotopically-labeled compounds of the invention (e.g., those incorporating radioisotopes) are useful in studies (e.g., assays) on tissue distribution of drug and/or substrate. The radioisotopes tritium (i.e., $^3H$) and carbon-14 (i.e., $^{14}C$) are particularly useful for this purpose due to their ease of incorporation and detection. Substitution with positron-emitting isotopes (e.g., $^{11}C$, $^{18}F$, $^{15}O$ and $^{13}N$) may be useful for examining substrate receptor occupancy in a positron emission tomography (PET) study. Isotopically labeled compounds of the invention can be prepared by replacing the previously employed non-labeled reagents with suitable isotopically labeled reagents, using methods similar to those described in the accompanying schemes and/or examples and preparations. The pharmaceutically acceptable solvates of the invention include those in which the crystalline solvent can be isotopically substituted, e.g., $D_2O$, acetone-$d_6$ or DMSO-$d_6$.

The chemical bond in the compound of the invention can be depicted herein with a solid line [———], a wavy line [∿∿∿], a solid wedge [━━▬] or a dashed wedge [⋯⋯⋯]. It is intended that a bond to an asymmetric atom depicted with a solid line indicates that all possible stereoisomers at the atom (e.g., specific enantiomers, racemic mixtures and the like) are contemplated. It is intended that a bond to an asymmetric atom depicted with a wavy line indicates that the bond is either a solid wedge [━━▬] bond or a dashed wedge [⋯⋯⋯] bond. It is intended that a bond to an asymmetric atom depicted with a solid or dashed wedge indicates the existence of the stereoisomer that is shown. When present in a racemic mixture, a solid or dashed wedge is used to define relative stereochemistry rather than absolute stereochemistry. Unless otherwise indicated, it is intended that the compound of the invention can be present in the form of stereoisomers (including cis- and trans-isomers, optical isomers (e.g., R and S enantiomers), diastereomers, geometric isomers, rotamers, conformers, atropisomers, and mixtures thereof). The compound of the invention can exhibit one or more types of the above isomerism, and can be consisted of a mixture thereof (e.g., a racemic mixture and a diastereomeric pair).

The compound of the invention contains one or more asymmetric centers, and thereby can be present in the form of a racemate, a racemic mixture, a single enantiomer, a diastereomeric mixture, a single diastereomer, or the like.

The invention encompasses all possible crystalline forms or polymorphs of the compound of the invention, which can be a single polymorph or a mixture of more than one polymorph in any ratio.

It will also be understood that certain compounds of the invention can exist in a free form for treatment, or where appropriate, in the form of a pharmaceutically acceptable derivative thereof. In the present invention, pharmaceutically acceptable derivatives include, but are not limited to, pharmaceutically acceptable salts, esters, solvates, metabolites or prodrugs, which can provide the compound of the invention or a metabolite or residue thereof directly or indirectly after administered to a patient in need thereof. Thus, when reference is made herein to "the compound of the invention," it is also intended to encompass the various derivative forms of the compound described above.

The "pharmaceutically acceptable salt" of the compound of the invention contemplates a salt formed with an inorganic acid such as sulfuric acid, hydrochloric acid, hydrobromic acid, phosphoric acid or nitric acid; a salt formed with an organic acid such as acetic acid, benzoic acid, oxalic acid, lactic acid, malic acid, tartaric acid, fumaric acid, maleic acid, citric acid, malonic acid, mandelic acid, gluconic acid, galactaric acid, glucoheptonic acid, glycolic acid, glutamic acid, trifluoroacetic acid, methanesulfonic acid, ethanesulfonic acid, benzenesulfonic acid, p-toluenesulfonic acid, camphorsulfonic acid or naphthalene-2-sulfonic acid; a salt formed with one or more metal ions such as a lithium ion, a sodium ion, a potassium ion, a calcium ion, a magnesium ion, a zinc ion, an aluminum ion; or a salt formed with an amine such as ammonia, arginine, lysine, piperazine, choline, diethylamine, 4-phenylcyclohexylamine, 2-aminoethanol or benzathine. It is not particularly limited as long as it is a pharmaceutically acceptable salt. The conversion from the free form to a salt can be carried out by an existing method.

The term "ester", as used herein, means an ester derived from a compound of each general formula herein, which includes a physiologically hydrolyzable ester (which can be hydrolyzed under physiological condition to release the compound of the invention in the form of a free acid or alcohol). The compound of the invention per se can also be an ester.

The compound of the invention can be present in the form of a solvate (preferably a hydrate) wherein the compound of the invention contains a polar solvent, particularly e.g., water, methanol or ethanol, as a structural element of the crystal lattice of the compound. The polar solvent, particularly water, can be present in an amount of a stoichiometric or non-stoichiometric ratio.

Also included within the scope of the invention are metabolites of the compound of the invention, i.e., substances formed in vivo upon administration of the compound of the invention. Such products can be generated, e.g., by the oxidation, reduction, hydrolysis, amidation, deamidation, esterification, delipidization, enzymatic hydrolysis or the like of the compound administered. Accordingly, the invention contemplates metabolites of the compound of the invention, including compounds prepared by contacting the compound of the invention with a mammal for a time sufficient to produce a metabolite thereof.

Further included within the scope of the invention are prodrugs of the compound of the invention, which are certain derivatives of the compound of the invention that have less or no pharmacological activity themselves but when administered into or onto the body, can be converted to the compound of the invention having the desired activity by, e.g., hydrolytic cleavage. Typically, such prodrugs will be functional group derivatives of the compound that are readily converted in vivo to the desired therapeutically active compound. Additional information on the use of prodrugs can be found in "Pro-drugs as Novel Delivery Systems", Vol. 14, ACS Symposium Series (T. Higuchi and V. Stella), and "Bioreversible Carriers in Drug Design," Pergamon Press, 1987 (ed. E. B. Roche, American Pharmaceutical Association). Prodrugs of the invention can be prepared, e.g., by replacing an appropriate functional group in the compound of the invention with a certain moiety as "pro-moiety" known to those skilled in the art (e.g., those described in "Design of Prodrugs", H. Bundgaard (Elsevier, 1985))".

The present invention also encompasses the compound of the invention containing a protective group. In any process for preparing the compound of the invention, it may be necessary and/or desirable to protect sensitive or reactive groups on any of a relevant molecule, thereby forming a chemically protected form of the compound of the invention. This can be achieved by conventional protective groups, for example, those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991, which are incorporated herein by reference. The protective groups can be removed at a suitable subsequent stage using methods known in the art.

The term "about" means a range of ±10%, preferably and more preferably ±2% of a specified value.

Compound

It is an object of the present invention to provide a compound represented by Formula (I), a pharmaceutically acceptable salt, ester, solvate, isomer thereof, any crystalline form or racemate of the foregoing, a metabolite form of the foregoing, or a mixture of the foregoing,

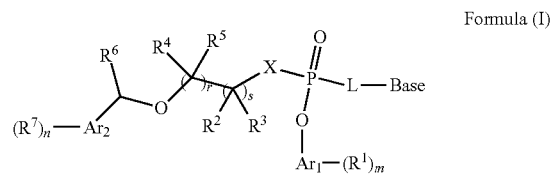

Formula (I)

wherein

L is selected from the group consisting of substituted or unsubstituted $C_{1-12}$ alkylene, $C_{2-12}$ alkenylene, $C_{2-12}$ alkynylene, and the alkylene, alkenylene or alkynylene is optionally interrupted by one or more —O—, —$NR^8$— or —S—; or L represents a group of Formula (c), Formula (d) or Formula (e), wherein ⁒ represents a single bond or a double bond, position 1 is attached to the Base, and position 2 is attached to the phosphorus atom (P):

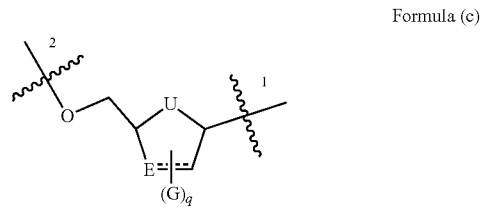

Formula (c)

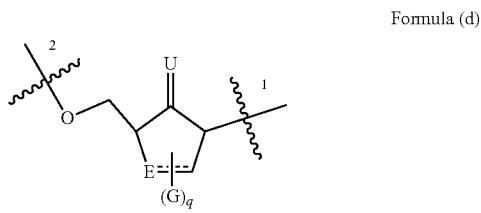

Formula (d)

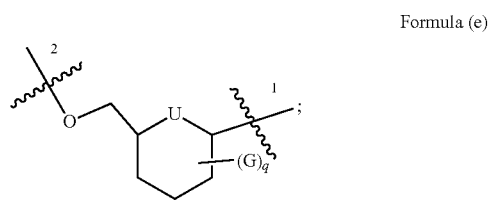

Formula (e)

Base represents a group of Formula (a) or Formula (b):

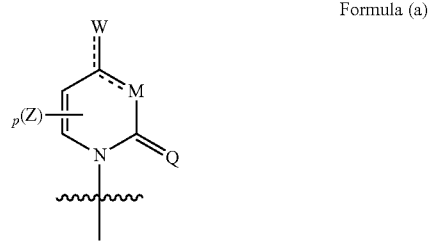

Formula (a)

-continued

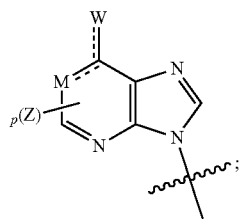

Formula (b)

═══ represents a single bond or a double bond;
M represents N or $NR^8$;
W represents H, $NR^8R^9$, $NR^8$, $CH_2$, O or S;
Q represents O, S, $NR^8$ or $CH_2$;
each Z, at each occurrence, independently represents hydrogen, halogen, hydroxy, cyano, nitro, azido, $NR^8R^9$, substituted or unsubstituted $C_{1-6}$ alkyl, substituted or unsubstituted $C_{1-6}$ alkoxy, or substituted or unsubstituted $C_{3-8}$ cycloalkyl, and if there are multiple Z groups, they each may be the same or different;
p represents 0, 1, 2, 3, 4 or 5;
provided that when M is attached by a double bond, W is attached by a single bond; and when M is attached by a single bond, W is attached by a double bond;
U represents O, S, $NR^8$ or $CR^{10}R^{11}$;
E represents $CR^{10}$, $CR^{10}R^{11}$ or S, provided that when E is attached by a double bond, it is $CR^{10}$;
each G, at each occurrence, independently represents hydrogen, halogen, hydroxyl, cyano, nitro, azido, $NR^8R^9$, substituted or unsubstituted $C_{1-6}$ alkyl, substituted or unsubstituted $C_{1-6}$ alkoxy, or substituted or unsubstituted $C_{3-8}$ cycloalkyl, and if there are multiple G groups, they each may be the same or different;
q represents an integer of from 0 to 5;
$Ar_1$ represents $C_{6-14}$ aryl or 5- to 14-membered heteroaryl;
each $R^1$, at each occurrence, represents hydrogen, halogen, —OH, —CN, —$NO_2$, —$NR^8R^9$, substituted or unsubstituted $C_{1-6}$ alkyl, substituted or unsubstituted $C_{1-6}$ alkoxy, substituted or unsubstituted $C_{1-6}$ haloalkyl, substituted or unsubstituted $C_{1-6}$ alkylthio, substituted or unsubstituted $C_{3-8}$ cycloalkyl, substituted or unsubstituted 3- to 10-membered heterocycloalkyl, substituted or unsubstituted $C_{2-10}$ alkenyl, or substituted or unsubstituted $C_{2-10}$ alkynyl, and if there are multiple R' groups, they each may be the same or different;
m represents an integer of from 0 to 7;
X represents $CH_2$, —S—, —O— or —$NR^8$—;
$R^2$ and $R^3$, at each occurrence, each independently represent hydrogen, substituted or unsubstituted $C_{1-6}$ alkyl, substituted or unsubstituted $C_{1-6}$ alkoxy, substituted or unsubstituted $C_{6-14}$ aryl, substituted or unsubstituted $C_{7-20}$ aralkyl, or substituted or unsubstituted $C_{3-8}$ cycloalkyl; or $R^2$ and $R^3$ together with the carbon atom to which they are attached, form substituted or unsubstituted $C_{3-8}$ cycloalkyl, or substituted or unsubstituted 3- to 10-membered heterocycloalkyl;
$R^4$ and $R^5$, at each occurrence, each independently represent hydrogen, substituted or unsubstituted $C_{1-6}$ alkyl, substituted or unsubstituted $C_{1-6}$ alkoxy, substituted or unsubstituted $C_{6-14}$ aryl, substituted or unsubstituted $C_{7-20}$ aralkyl, or substituted or unsubstituted $C_{3-8}$ cycloalkyl group; or $R^4$ and $R^5$ together with the carbon atom to which they are attached, form substituted or unsubstituted $C_{3-8}$ cycloalkyl, or substituted or unsubstituted 3- to 10-membered heterocycloalkyl; or $R^3$ and $R^4$ are linked to each other, together with the carbon atoms to which they each are attached, form substituted or unsubstituted $C_{3-8}$ cycloalkyl, or substituted or unsubstituted 3- to 10-membered heterocycloalkyl;
$R^6$ represents hydrogen, substituted or unsubstituted $C_{1-6}$ alkyl, substituted or unsubstituted $C_{3-8}$ cycloalkyl, substituted or unsubstituted $C_{6-14}$ aryl group, substituted or unsubstituted $C_{7-20}$ aralkyl, or substituted or unsubstituted $C_{1-6}$ alkoxy;
each $R^7$, at each occurrence, independently represents hydrogen, halogen, —OH, —CN, —$NO_2$, —$NR^8R^9$, substituted or unsubstituted $C_{1-6}$ alkyl, substituted or unsubstituted $C_{1-6}$ haloalkyl, substituted or unsubstituted $C_{1-6}$ alkylthio, substituted or unsubstituted $C_{3-8}$ cycloalkyl, substituted or unsubstituted 3- to 10-membered heterocycloalkyl, substituted or unsubstituted $C_{2-10}$ alkynyl, or substituted or unsubstituted $C_{1-6}$ alkoxy, and if there are multiple $R^7$ groups, they each may be the same or different; or
$R^6$ and $R^7$ are linked to each other, together with the carbon atoms therebetween, form substituted or unsubstituted $C_{3-8}$ carbocyclyl or 3- to 10-membered heterocyclyl;
n represents an integer of from 0 to 7; Are represents $C_{6-14}$ aryl or 5- to 14-membered heteroaryl;
r and s each independently represent 1, 2 or 3;
$R^8$ and $R^9$, at each occurrence, each independently represent hydrogen, substituted or unsubstituted $C_{1-6}$ alkyl, or substituted or unsubstituted $C_{3-8}$ cycloalkyl, if there are multiple $R^8$ and $R^9$ groups, they each may be the same or different; and
$R^{10}$ and $R^{11}$, at each occurrence, each independently represent hydrogen, substituted or unsubstituted $C_{1-6}$ alkyl, or substituted or unsubstituted $C_{3-8}$ cycloalkyl, or $R^{10}$ and $R^{11}$ together form $C_{1-6}$ alkylene, and if there are multiple $R^{10}$ and $R^{11}$ groups, they each may be the same or different.

According to some embodiments of the invention, the compound of the invention is a compound of Formula (Ia):

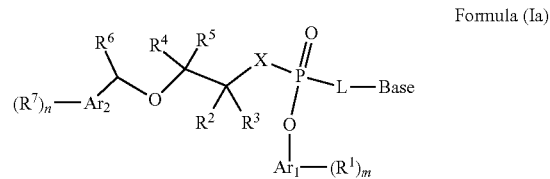

Formula (Ia)

wherein
L-Base represents a group of Formula (f) or Formula (g):

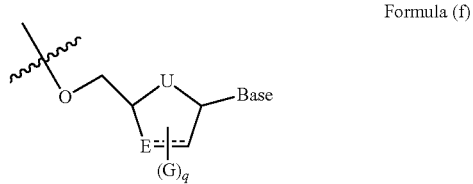

Formula (f)

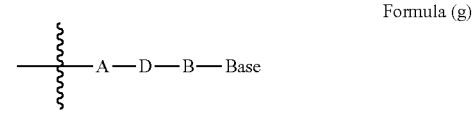

Formula (g)

Base represents a group of Formula (a) or Formula (b):

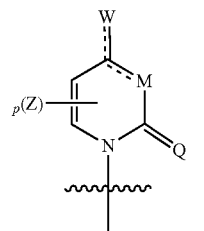

Formula (a)

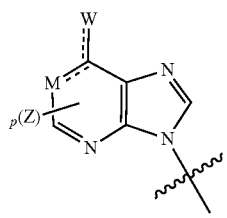

Formula (b)

wherein
===== represents a single bond or a double bond;
M represents N or $NR^8$;
W represents $NR^8R^9$ or O;
Q represents O or S;
each Z, at each occurrence, independently represents hydrogen, halogen, $NR^8R^9$, substituted or unsubstituted $C_{1-6}$ alkyl, substituted or unsubstituted $C_{1-6}$ alkoxy, or substituted or unsubstituted $C_{3-8}$ cycloalkyl, and if there are multiple Z groups, they each may be the same or different;
p represents an integer of from 0 to 2;
provided that when M is attached by a double bond, W is attached by a single bond, M represents N, and W represents $NR^8R^9$; and when M is attached by a single bond, W is attached by a double bond, M represents $NR^8$, and W represents O;
U represents O, S or $CR^{10}R^{11}$;
E represents $CR^{10}$, $CR^{10}R^{11}$ or S, provided that when E is attached by a double bond, it is $CR^{10}$;
each G, at each occurrence, independently represents hydrogen, halogen, hydroxy, azido, substituted or unsubstituted $C_{1-6}$ alkyl, substituted or unsubstituted $C_{1-6}$ alkoxy, or substituted or unsubstituted $C_{3-8}$ cycloalkyl, and if there are multiple G groups, they each may be the same or different;
q represents an integer of from 0 to 4;
A represents substituted or unsubstituted $C_{1-6}$ alkylene;
B represents substituted or unsubstituted alkylene;
D represents O, S or $NR^B$;
$Ar_1$ represents $C_{6-10}$ aryl or $C_{3-10}$ heteroaryl;
each $R^1$, at each occurrence, independently represents hydrogen, halogen, substituted or unsubstituted $C_{1-6}$ alkyl, substituted or unsubstituted $C_{1-6}$ alkoxy, substituted or unsubstituted $C_{3-8}$ cycloalkyl, substituted or unsubstituted $C_{3-8}$ heterocycloalkyl, substituted or unsubstituted $C_{2-10}$ alkenyl group, or substituted or unsubstituted $C_{2-10}$ alkynyl, and if there are multiple $R^1$ groups, they each may be the same or different;
m represents an integer of from 0 to 7;
X represents —O— or $-NR^8-$;
$R^2$ and $R^3$ each independently represent hydrogen, substituted or unsubstituted $C_{1-6}$ alkyl, substituted or unsubstituted $C_{3-8}$ cycloalkyl; or $R^2$ and $R^3$ together with the carbon atom to which they are attached, form substituted or unsubstituted $C_{3-8}$ cycloalkyl, or substituted or unsubstituted $C_{3-8}$ heterocycloalkyl;
$R^4$ and $R^5$ each independently represent hydrogen, substituted or unsubstituted $C_{1-6}$ alkyl, substituted or unsubstituted $C_{3-8}$ cycloalkyl; or $R^4$ and $R^5$ together with the carbon atom to which they are attached, form substituted or unsubstituted $C_{3-8}$ cycloalkyl, or substituted or unsubstituted $C_{3-8}$ heterocycloalkyl; or
$R^3$ and $R^4$ are linked to each other, together with the carbon atoms to which they each are attached, form substituted or unsubstituted $C_{4-8}$ cycloalkyl, or substituted or unsubstituted $C_{4-8}$ heterocycloalkyl;
$R^6$ represents hydrogen, substituted or unsubstituted $C_{1-6}$ alkyl, substituted or unsubstituted $C_{3-8}$ cycloalkyl, or substituted or unsubstituted $C_{1-6}$ alkoxy;
each $R^7$, at each occurrence, independently represents hydrogen, halogen, substituted or unsubstituted $C_{1-6}$ alkyl, substituted or unsubstituted $C_{3-8}$ cycloalkyl, or substituted or unsubstituted $C_{1-6}$ alkoxy, and if there are multiple $R^7$ groups, they each may be the same or different; or
$R^6$ and $R^7$ are linked to each other, together with the carbon atoms therebetween, form substituted or unsubstituted $C_{4-8}$ carbocyclyl or $C_{4-8}$ heterocyclyl;
n represents an integer of from 0 to 7;
$Ar_2$ represents $C_{6-10}$ aryl or $C_{3-10}$ heteroaryl;
$R^8$ and $R^9$, at each occurrence, each independently represent hydrogen, substituted or unsubstituted $C_{1-6}$ alkyl, or substituted or unsubstituted $C_{3-8}$ cycloalkyl, and if there are multiple $R^8$ and $R^9$ groups, they each may be the same or different, and
$R^{10}$ and $R^{11}$, at each occurrence, each independently represent hydrogen, substituted or unsubstituted $C_{1-6}$ alkyl, or substituted or unsubstituted $C_{3-8}$ cycloalkyl, or $R^{10}$ and $R^{11}$ together form $C_{1-6}$ alkylene, and if there are multiple $R^{10}$ and $R^{11}$ groups, they each may be the same or different.

According to some embodiments of the invention, the invention provides a compound represented by the above Formula (I), a pharmaceutically acceptable salt, ester, solvate, isomer thereof, any crystalline form or racemate of the foregoing, a metabolite form of the foregoing, or a mixture of the foregoing,
wherein
r and s are both 1;
Base is selected from the group consisting of:

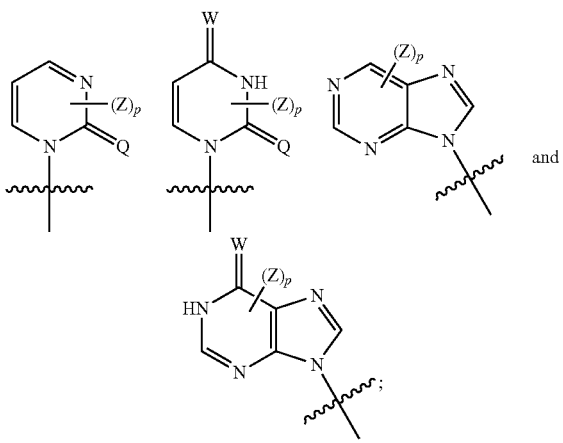

L is selected from the group consisting of $C_{1-6}$ alkylene and $C_{2-6}$ alkenylene, $C_{2-6}$ alkynylene, which are optionally substituted by one or more G groups, and the alkylene, alkenylene or alkynylene is optionally interrupted by one or more —O—, —$NR^8$— or —S—; or L is selected from the group consisting of:

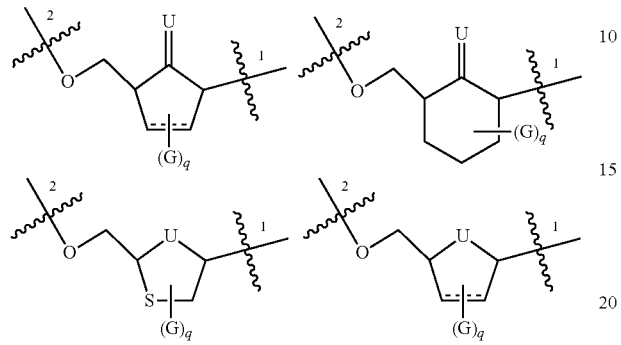

wherein

═══ represents a single bond or a double bond, position 1 is attached to the Base, and position 2 is attached to the phosphorus atom (P);

X, U, W and Q, at each occurrence, are each independently selected from the group consisting of $CH_2$, O, S and $NR^8$;

G and Z, at each occurrence, are each independently selected from the group consisting of halogen, —OH, —CN, —$NO_2$, —$NR^8R^9$, —$N_3$, $C_{1-6}$ alkyl and $C_{3-6}$ cycloalkyl;

p and q, at each occurrence, are each independently 0, 1, 2, 3, 4 or 5, provided that p is not greater than the number of substitutable positions on the corresponding group and q is not greater than the number of substitutable positions on the corresponding group; when p is greater than 1, each Z may be the same or different; and when q is greater than 1, each G may be the same or different;

$Ar_1$ and $Ar_2$ are each independently selected from the group consisting of $C_{6-14}$ aryl and 5- to 14-membered heteroaryl;

m and n are each independently selected from the group consisting of 1, 2, 3, 4 or 5, preferably 1 or 2;

$R^1$ and $R^7$ are each independently selected from the group consisting of hydrogen, halogen, —OH, —CN, —$NO_2$, —$NR^8R^9$, $C_{1-6}$ alkyl, $C_{1-6}$ haloalkyl, $C_{1-6}$ alkoxy, $C_{1-6}$ alkylthio, $C_{3-6}$ cycloalkyl, 3- to 10-membered heterocycloalkyl and $C_{2-6}$ alkynyl;

$R^8$ and $R^9$, at each occurrence, each independently represent hydrogen, $C_{1-6}$ alkyl and $C_{3-6}$ cycloalkyl;

$R^2$ and $R^3$ are each independently selected from the group consisting of hydrogen, $C_{1-6}$ alkyl, $C_{3-6}$ cycloalkyl, $C_{1-6}$ alkoxy, $C_{6-14}$ aryl and $C_{7-20}$ aralkyl, the alkyl, cycloalkyl, alkoxy, aryl and aralkyl are each optionally substituted by one or more substituents selected from the group consisting of halogen, —OH, —CN and —$NO_2$; or $R^2$ and $R^3$ together with the carbon atom to which they are attached, form $C_{3-6}$ cycloalkyl or 3- to 10-membered heterocycloalkyl;

$R^4$ and $R^5$ are each independently selected from the group consisting of hydrogen, $C_{1-6}$ alkyl, $C_{3-6}$ cycloalkyl, $C_{1-6}$ alkoxy, $C_{6-14}$ aryl and $C_{2-20}$ aralkyl, and the alkyl, cycloalkyl, alkoxy, aryl and aralkyl are each optionally substituted by one or more substituents selected from the group consisting of halogen, —OH, —CN and —$NO_2$; or $R^4$ and $R^5$ together with the carbon atom to which they are attached, form $C_{3-6}$ cycloalkyl or 3- to 10-membered heterocycloalkyl; or $R^3$ and $R^4$ together with the carbon atoms to which they are attached, form $C_{3-6}$ cycloalkyl or 3- to 10-membered heterocycloalkyl; and $R^6$ is selected from the group consisting of hydrogen, $C_{1-6}$ alkyl, $C_{3-6}$ cycloalkyl, $C_{1-6}$ alkoxy, $C_{6-14}$ aryl and $C_{7-20}$ aralkyl, the alkyl, cycloalkyl, alkoxy, aryl and aralkyl are each optionally substituted by one or more substituents selected from the group consisting of halogen, —OH, —CN and —$NO_2$; or $R^6$ and $R^7$ together with the carbon atom to which they are attached, form $C_{3-6}$ cycloalkyl or 3- to 10-membered heterocycloalkyl fused to $Ar_2$; and preferably, $R^6$ and $R^7$ together with the carbon atom to which they are attached, form $C_{4-6}$ cycloalkyl or 4- to 10-membered heterocycloalkyl fused to $Ar_2$.

According to some embodiments of the invention, $R^8$ is hydrogen, $C_{1-6}$ alkyl or $C_{3-8}$ cycloalkyl. In some preferred embodiments, $R^8$ is hydrogen, methyl, ethyl, propyl or cyclopropyl.

According to some embodiments of the invention, $R^9$ is hydrogen, $C_{1-6}$ alkyl or $C_{3-8}$ cycloalkyl. In some preferred embodiments, $R^9$ is hydrogen, methyl, ethyl, propyl or cyclopropyl. In some particularly preferred embodiments, $R^9$ is hydrogen.

According to some embodiments of the invention, each Z, at each occurrence, is independently hydrogen, halogen, $NR^8R^9$ or $C_{1-6}$ alkyl. In some preferred embodiments, each Z, at each occurrence, is independently hydrogen, fluoro, chloro, methyl, ethyl or propyl.

According to some embodiments of the invention, p is 0, 1, 2, 3 or 4.

According to some embodiments of the invention, $R^{10}$ and $R^{11}$, at each occurrence, are each independently hydrogen, $C_{1-6}$ alkyl or $C_{3-8}$ cycloalkyl, or $R^{10}$ and $R^{11}$ together form $C_{1-6}$ alkylene. In some preferred embodiments, $R^{10}$ and $R^{11}$, at each occurrence, are each independently hydrogen, methyl, ethyl, propyl, cyclopropyl, cyclobutyl or cyclopentyl, or $R^{10}$ and $R^{11}$ together form methylene or ethylene.

According to some embodiments of the invention, U is O or S. In some preferred embodiments, U is O.

According to some embodiments of the invention, E is $CH_2$.

According to some embodiments of the invention, each G, at each occurrence, is independently hydrogen, halogen, hydroxy, azido or $C_{1-6}$ alkyl. In some preferred embodiments, each G, at each occurrence, is independently hydrogen, fluoro, chloro, hydroxy, methyl, ethyl, propyl, butyl or azido.

According to some embodiments of the invention, q is 0, 1, 2, 3 or 4.

According to some embodiments of the invention, A is $C_{1-3}$ alkylene that is unsubstituted or substituted by $C_{1-3}$ alkyl. In some preferred embodiments, A is methylene, ethylene or isopropylene.

According to some embodiments of the invention, B is $C_{1-3}$ alkylene that is unsubstituted or substituted by $C_{1-3}$ alkyl. In some preferred embodiments, B is ethylene or isopropylene.

According to some embodiments of the invention, D is O.

According to some embodiments of the invention, Base is a group represented by the a formula of
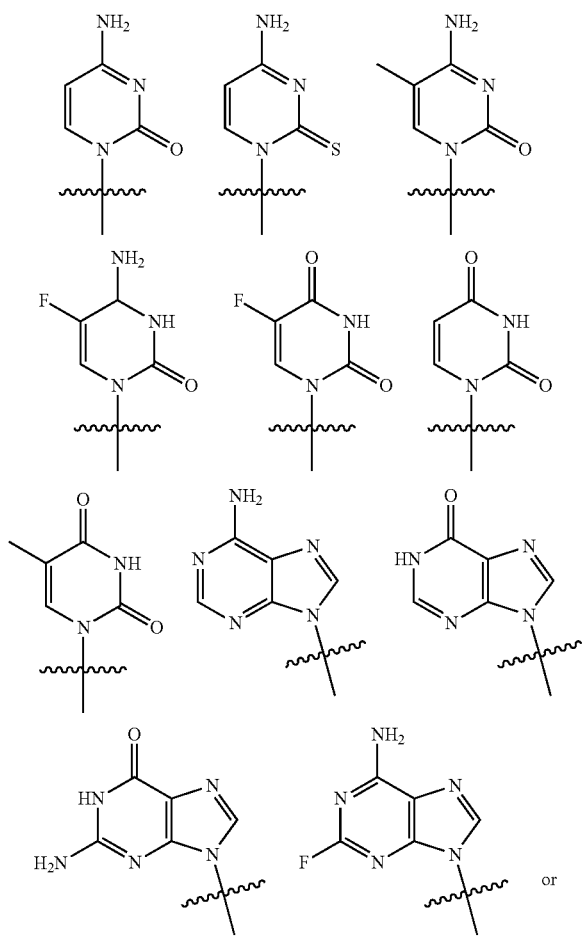
According to an embodiment of the invention, L is selected from the group consisting of:
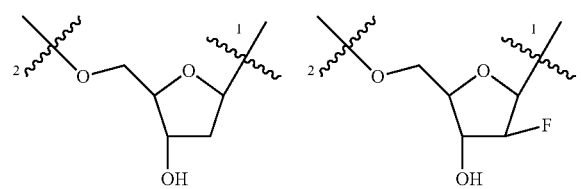
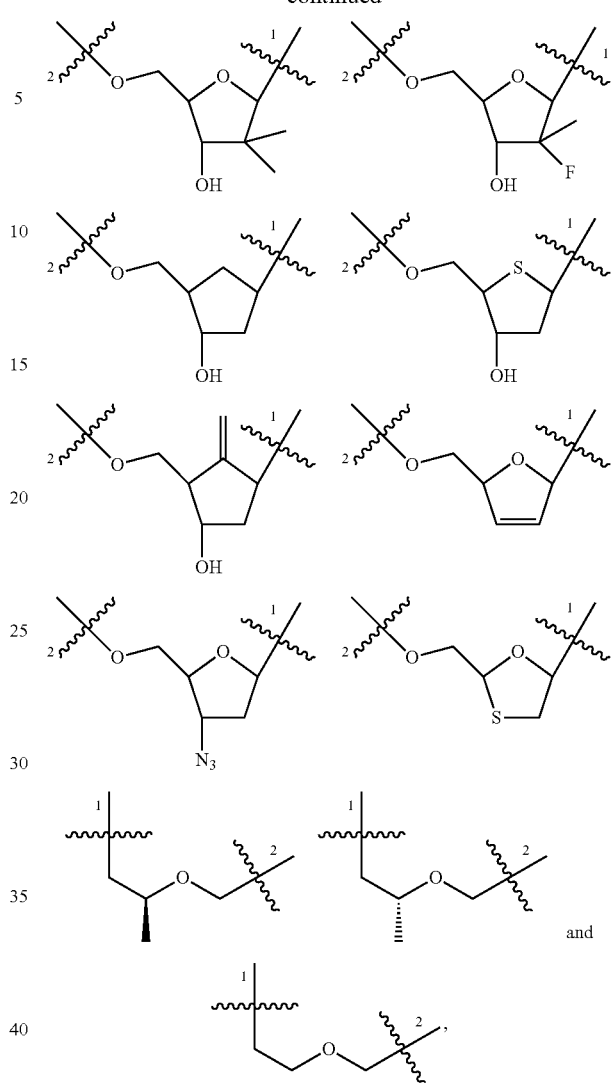
wherein position 1 is attached to B, and position 2 is attached to the phosphorus atom (P).
According to some embodiments of the invention, L-Base is a group represent by a formula of
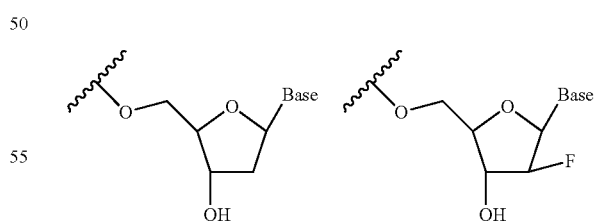
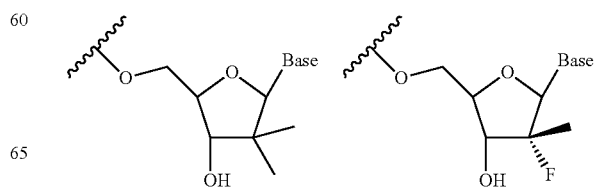

According to some embodiments of the invention, $R^2$ and $R^3$ together with the carbon atom to which they are attached, form $C_{3-8}$ cycloalkyl. In some preferred embodiments, $R^2$ and $R^3$ together with the carbon atom to which they are attached, form cyclopropyl, cyclobutyl, cyclopentyl or cyclohexyl.

According to some embodiments of the invention, $R^4$ and $R^5$, at each occurrence, are each independently hydrogen or $C_{1-6}$ alkyl. In some preferred embodiments, $R^4$ and $R^5$, at each occurrence, are each independently hydrogen, methyl, ethyl or propyl.

According to some embodiments of the invention, $R^6$ is hydrogen, $C_{1-6}$ alkyl or $C_{3-8}$ cycloalkyl. In some preferred embodiments, $R^6$ is hydrogen, methyl, ethyl, propyl, cyclopropyl or cyclobutyl.

According to some embodiments of the invention, each $R^7$, at each occurrence, is independently hydrogen, $C_{1-6}$ alkyl, $C_{3-8}$ cycloalkyl or $C_{1-6}$ alkoxy. In some preferred embodiments, each $R^7$, at each occurrence, is independently hydrogen, fluoro, chloro, bromo, methyl, ethyl, propyl, t-butyl, methoxy, cyclopropyl or cyclobutyl.

According to some embodiments of the invention, n is 0, 1, 2, 3 or 4.

In the present invention, if there are multiple G, Z, $R^1$, $R^2$, $R^3$, $R^4$, $R^5$, $R^7$, $R^8$, $R^9$ and $R^{10}$ groups in a same formula, each group is independently selected. That is, in a same formula, the groups represented by a same symbol can be the same or different.

According to some embodiments of the invention, the compound of the invention is a compound of Formula (II),

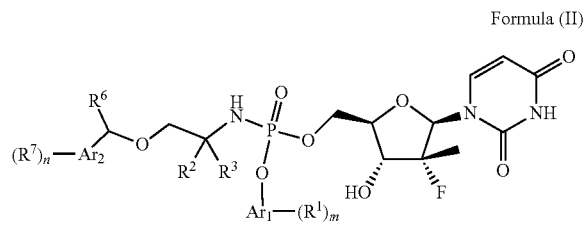

Formula (II)

wherein $R^1$, $R^2$, $R^3$, $R^6$, $R^7$, m, n, $Ar_1$ and $Ar_2$ are as defined above.

In some preferred embodiments, the compound of the invention is a compound of Formula (IIa),

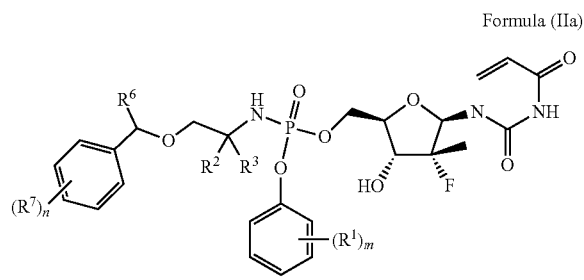

Formula (IIa)

wherein $R^1$, $R^2$, $R^3$, $R^6$, $R^7$, m and n are as defined above.

According to some embodiments of the invention, X is NH, N—$C_{1-6}$ alkyl (e.g., N-methyl) or O. In some preferred embodiments, X is NH.

According to some embodiments of the invention, $Ar_1$ is phenyl, 1-naphthyl, 2-naphthyl or 5- to 6-membered heteroaryl (e.g., thienyl, pyridyl or pyrazolyl).

According to some embodiments of the invention, $Ar_2$ is phenyl, 1-naphthyl, 2-naphthyl or a 5- to 6-membered heteroaryl (e.g., thienyl, pyridyl or pyrazolyl).

According to some embodiments of the invention, each $R^1$, at each occurrence is independently hydrogen, halogen, $C_{1-6}$ alkyl or $C_{1-6}$ alkoxy. In some preferred embodiments, each $R^1$, at each occurrence, is independently hydrogen, fluoro, chloro, bromo, methyl, ethyl or propyl.

According to some embodiments of the invention, m is 0, 1, 2, 3 or 4.

According to some embodiments of the invention, $R^2$ and $R^3$, at each occurrence, are each independently hydrogen or $C_{1-6}$ alkyl. In some preferred embodiments, $R^2$ and $R^3$, at each occurrence, are each independently hydrogen, methyl, ethyl or propyl.

In some particularly preferred embodiments, the compound of the invention is a compound of Formula (IIb),

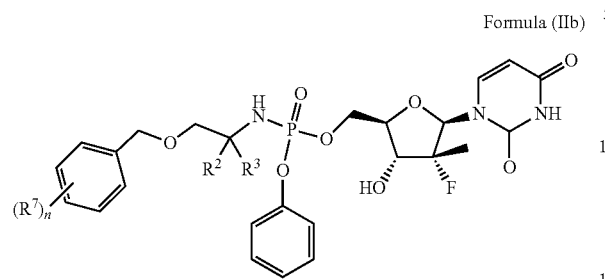

Formula (IIb)

wherein $R^2$, $R^3$, $R^7$ and n are as defined above.

According to some embodiments of the invention, the compound of the invention is a compound of Formula (III),

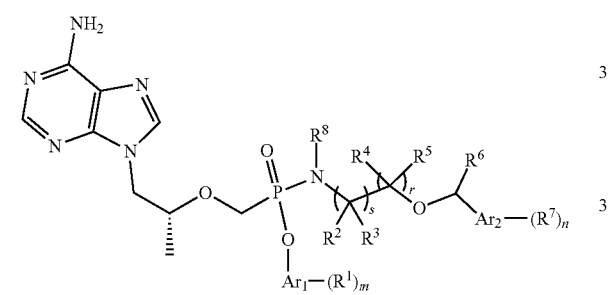

Formula (III)

wherein $R^1$, $R^2$, $R^3$, $R^4$, $R^5$, $R^6$, $R^7$, $R^8$, m, n, s, r, $Ar_1$ and $Ar_2$ are as defined above.

In some preferred embodiments, the compound of the invention is a compound of Formula (IIIa),

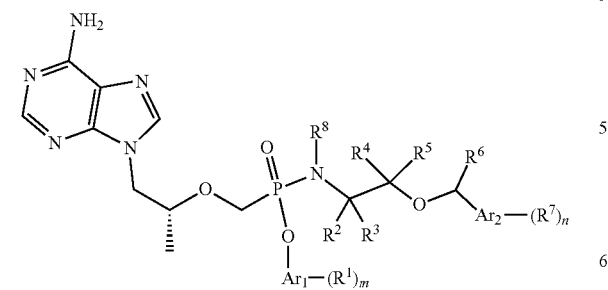

Formula (IIIa)

wherein $R^1$, $R^2$, $R^3$, $R^4$, $R^5$, $R^6$, $R^7$, $R^8$, m, n, $Ar_1$ and $Ar_2$ are as defined above.

In some particularly preferred embodiments, the compound of the invention is a compound of Formula (IIIb),

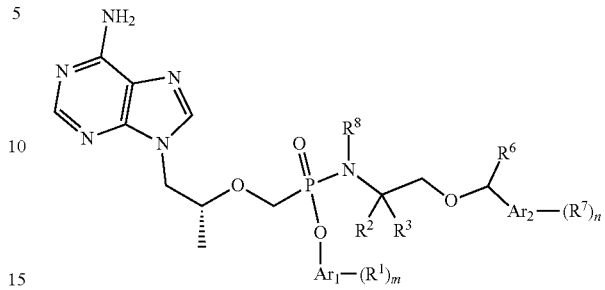

Formula (IIIb)

wherein $R^1$, $R^2$, $R^3$, $R^6$, $R^7$, $R^8$, m, n, $Ar_1$ and $Ar_2$ are as defined above.

In some particularly preferred embodiments, the compound of the invention is a compound of Formula (IIIc-1) or Formula (IIIc-2),

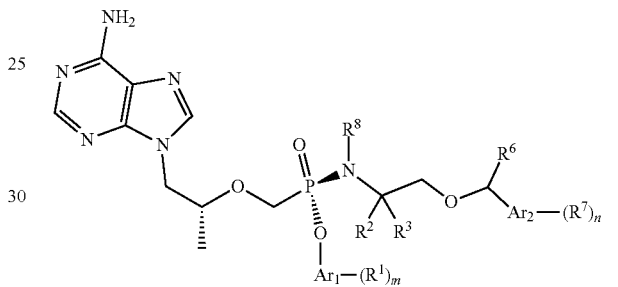

Formula (IIIc-1)

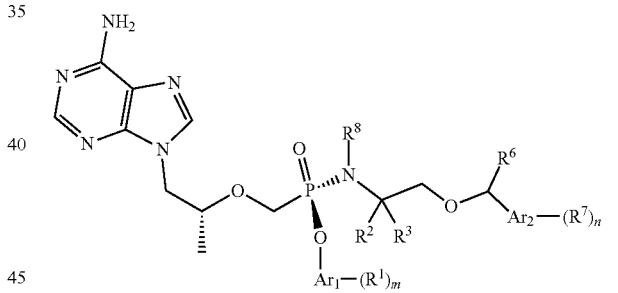

Formula (IIIc-2)

wherein $R^1$, $R^2$, $R^3$, $R^6$, $R^7$, $R^8$, m, n, $Ar_1$ and $Ar_2$ are as defined above.

According to some embodiments of the invention, the compound of the invention is a compound of Formula (IV),

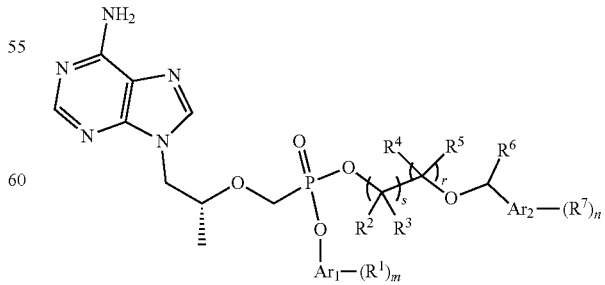

Formula (IV)

wherein $R^1$, $R^2$, $R^3$, $R^4$, $R^5$, $R^6$, $R^7$, m, n, s, r, $Ar_1$ and $Ar_2$ are as defined above.

According to some embodiments of the invention, the compound of the invention is
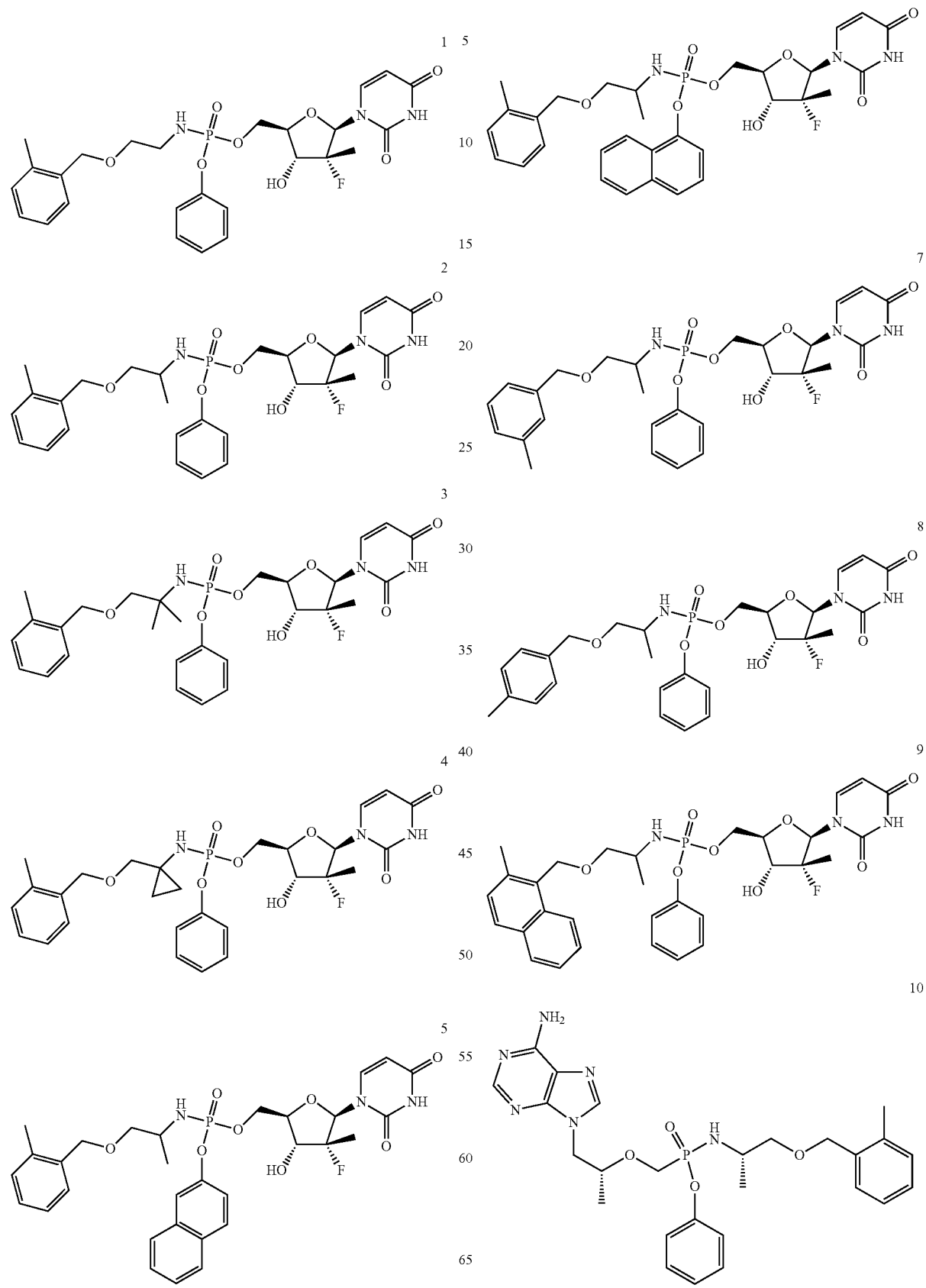

31
-continued
11
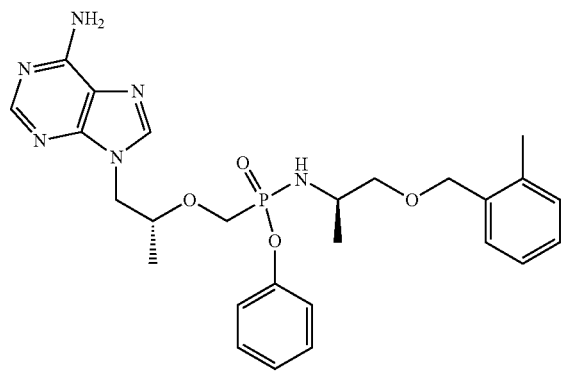
12
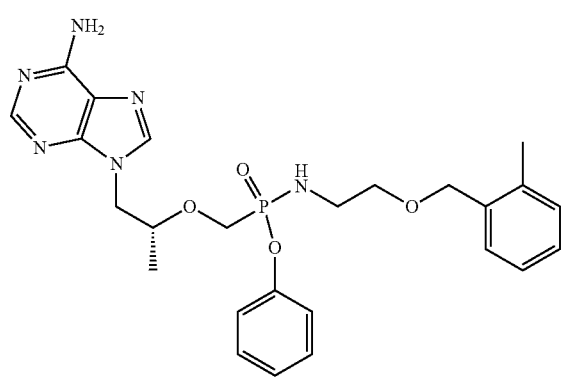
13
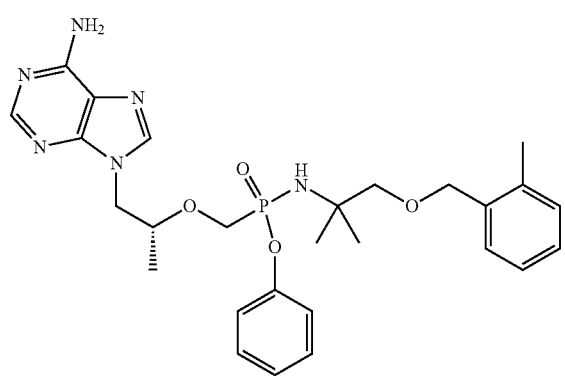
14
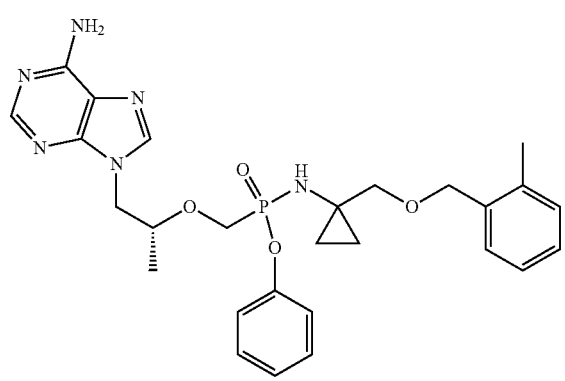
32
-continued
15
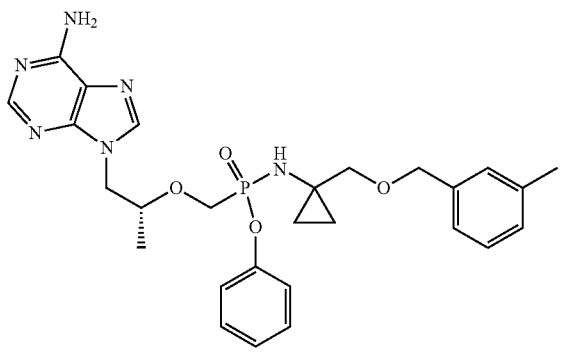
16
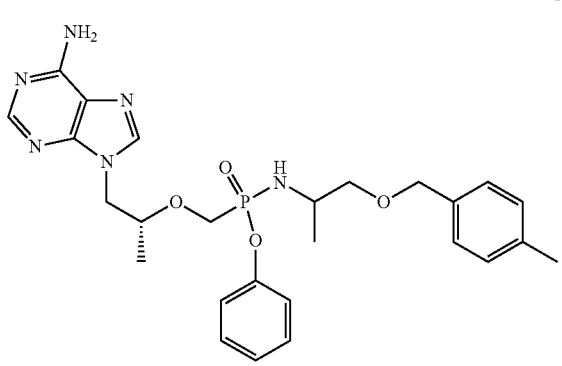
17
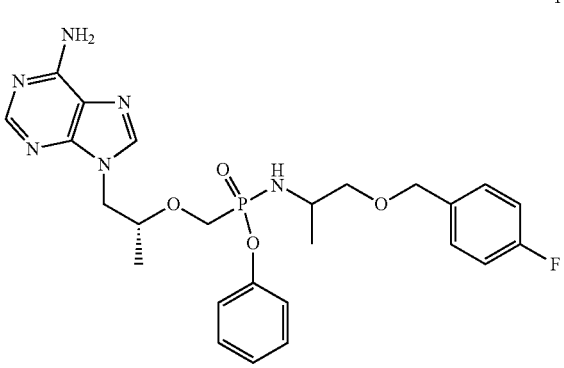
18
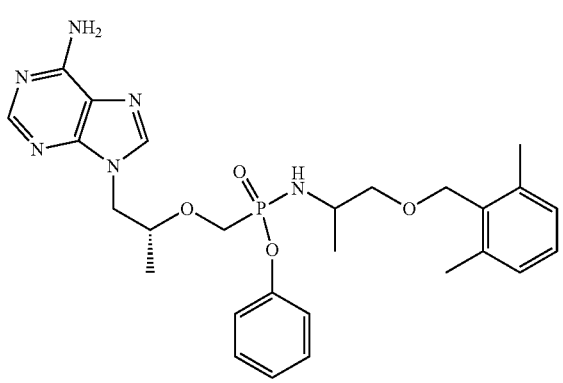

33
-continued
19
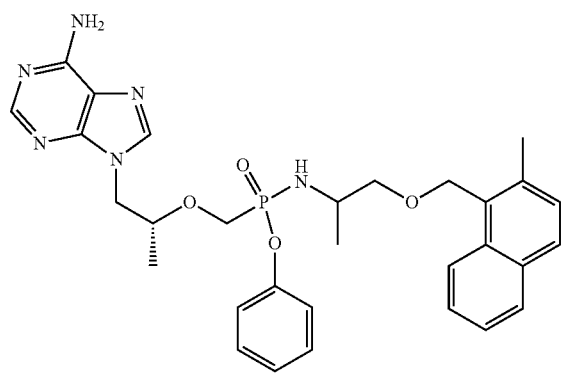
20
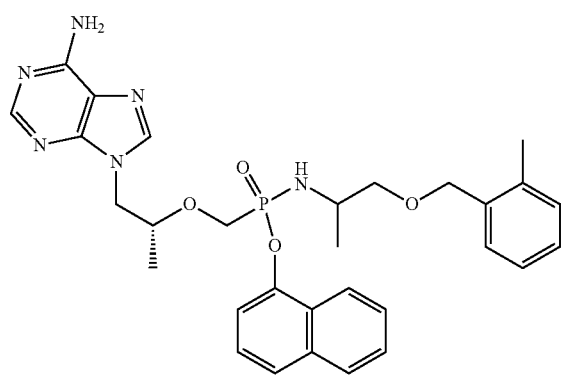
21
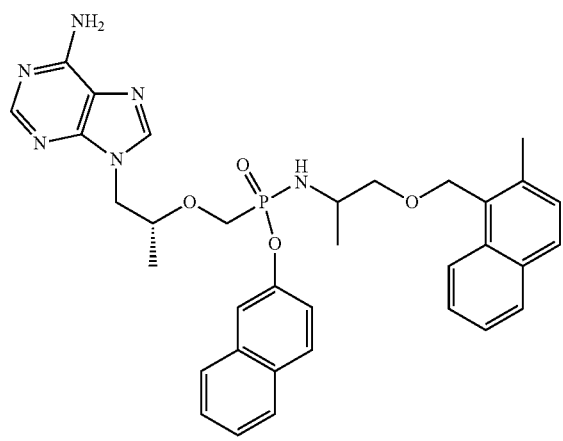
22
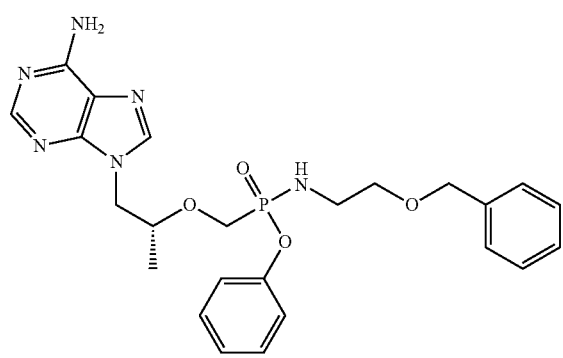
34
-continued
23
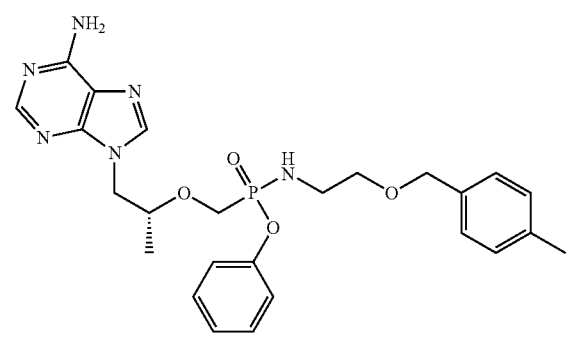
24
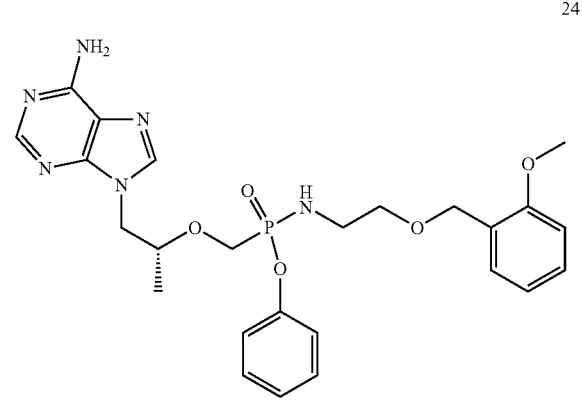
25
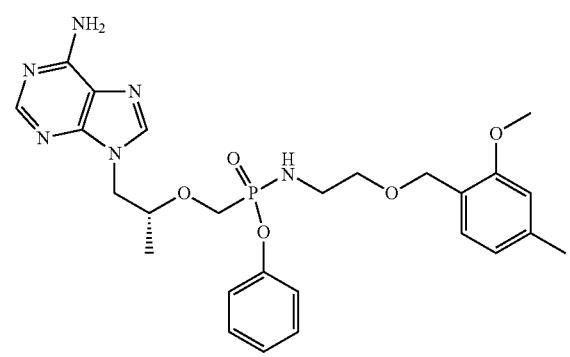
26
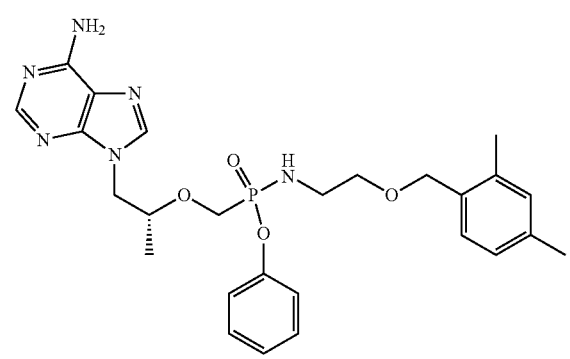

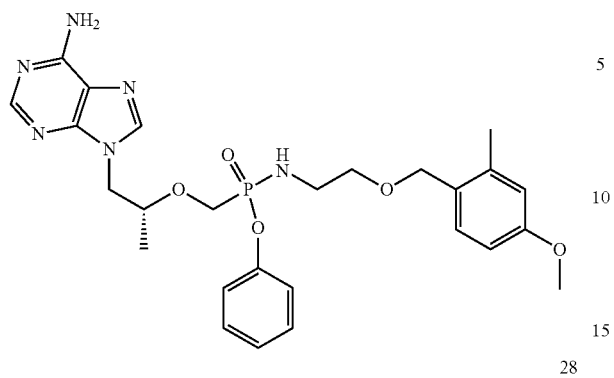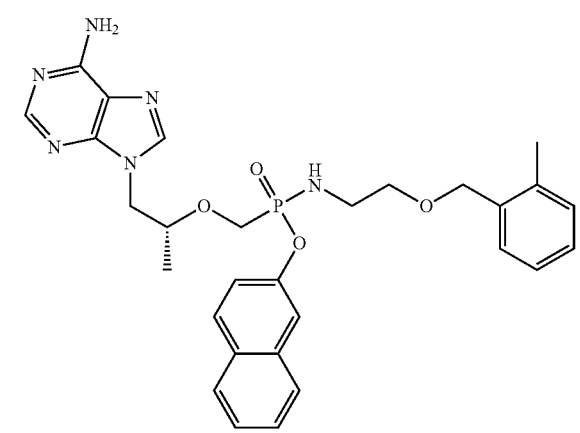

35
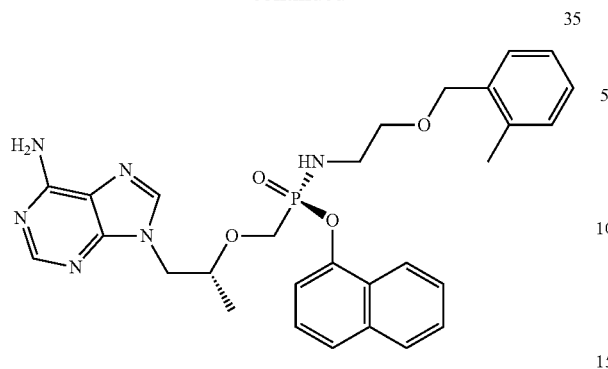
39
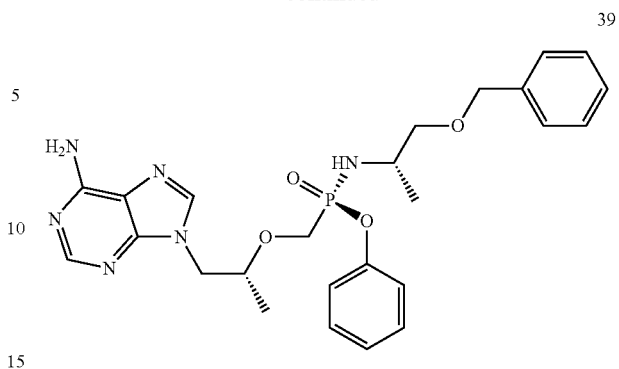
36
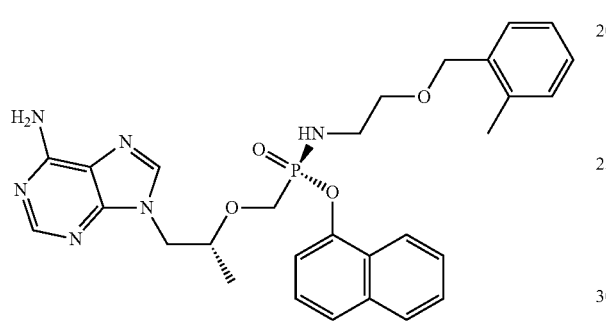
40
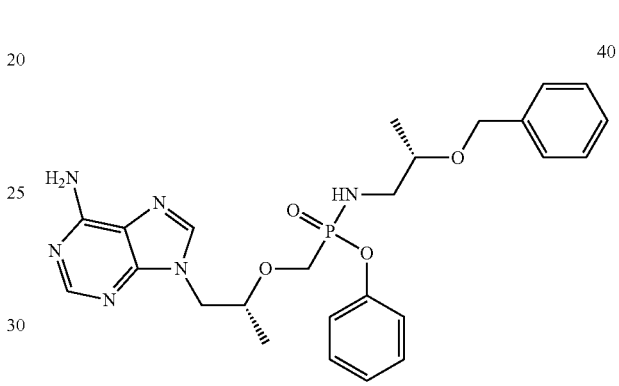
37
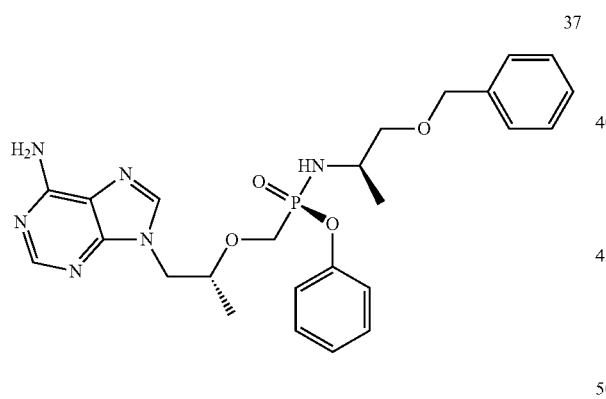
41
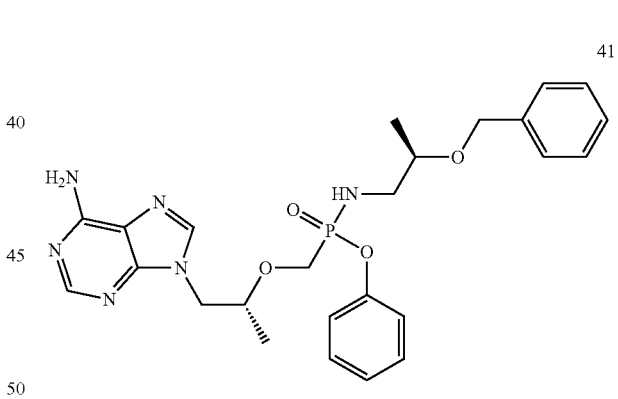
38
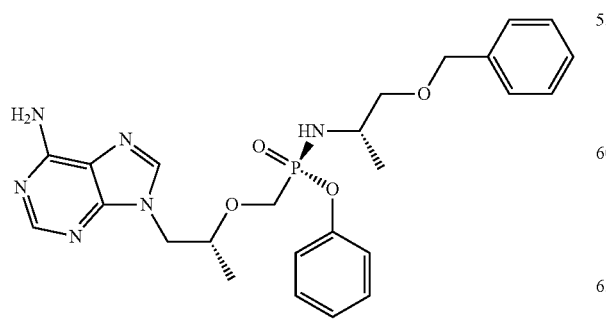
42
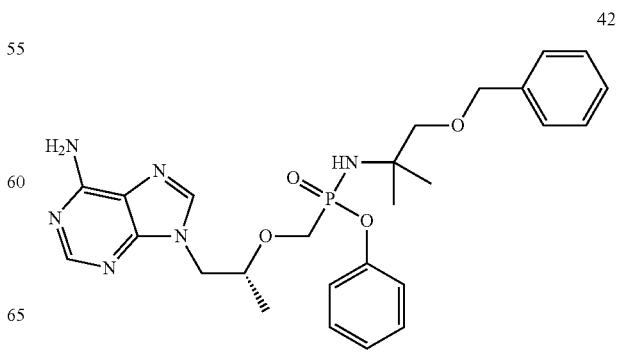

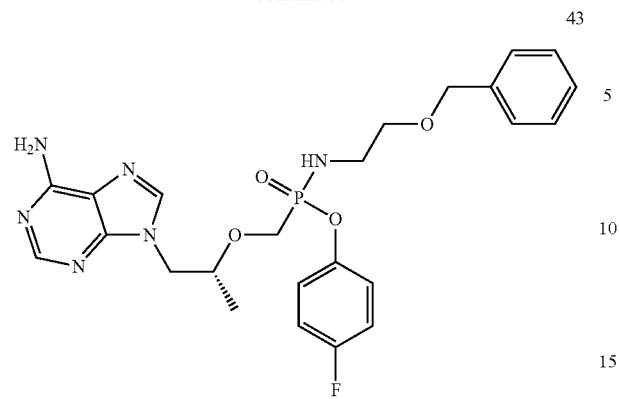
43
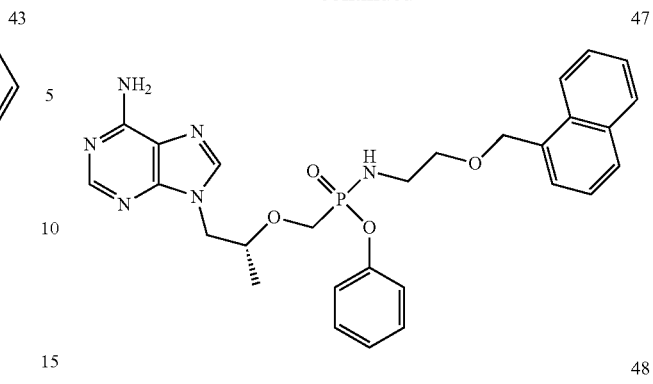
47
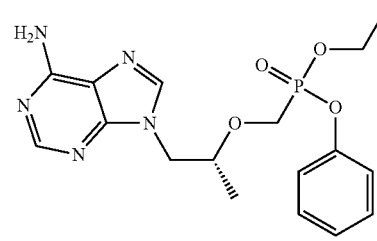
44
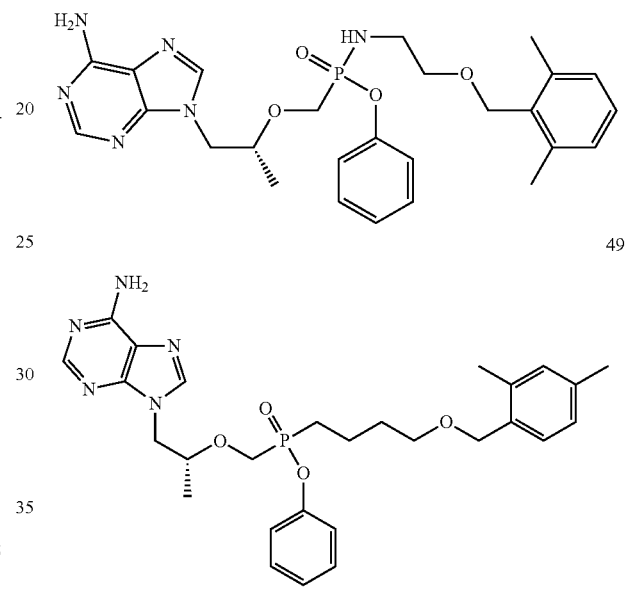
48
49
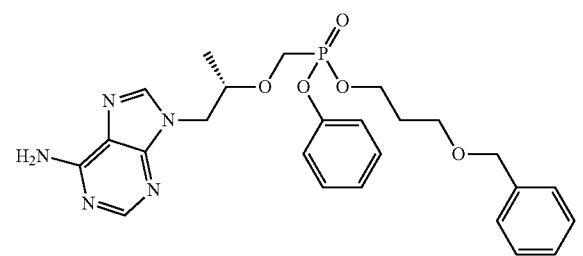
45
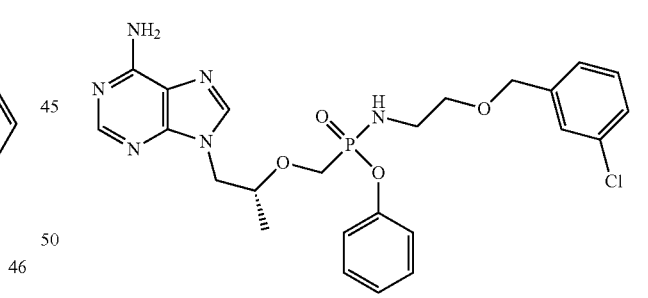
50
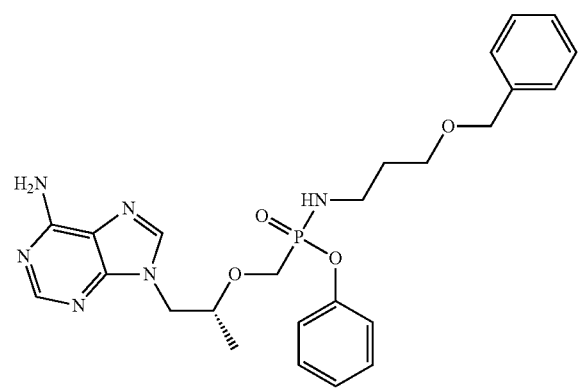
46
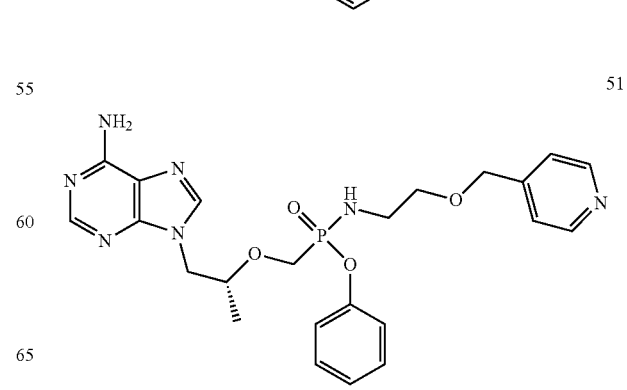
51

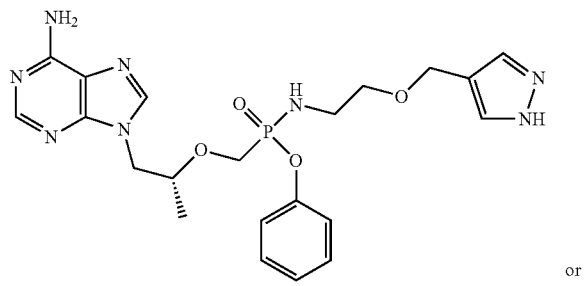

52 or

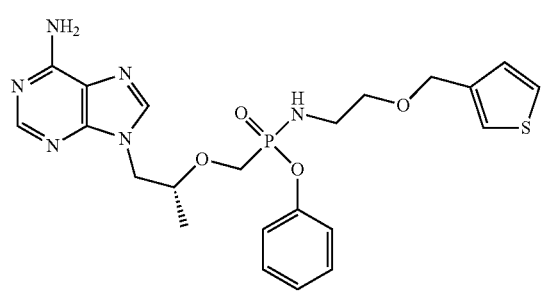

53

Pharmaceutical Composition

Another object of the invention is to provide a pharmaceutical composition comprising the compound of the invention, a pharmaceutically acceptable salt, ester, solvate, isomer thereof, any crystalline form or racemate of the foregoing, a metabolite form of the foregoing, or a mixture of the foregoing, wherein the pharmaceutical composition is in the form of a solid formulation, a semisolid formulation, a liquid formulation, or a gaseous formulation.

According to some embodiments of the invention, the pharmaceutical composition of the invention further comprises a pharmaceutically acceptable adjuvant for forming a pharmaceutical formulation. The adjuvant can be a carrier, an excipient, a diluent, or a combination thereof. The carrier, excipient and diluent refer to inactive ingredients in a pharmaceutical composition that do not cause significant irritation to organism and do not interfere with the biological activity of the compound administered. The carrier, excipient and diluent include water, lactose, glucose, fructose, sucrose, sorbitol, mannitol, polyethylene glycol, propylene glycol, starch, gel, alginate, calcium silicate, calcium phosphate, cellulose, aqueous syrup, methyl cellulose, polyvinyl pyrrolidone, alkyl p-hydroxybenzoate, talc, magnesium stearate, stearic acid, glycerin, and various oils including sesame oil, olive oil, soybean oil and the like. Further, an additive such as a bulking agent, a binder, a disintegrant, a pH modifier or a dissolving agent that are generally used can be blended in the above carrier, excipient or diluent as needed.

According to some embodiments of the invention, the pharmaceutical composition of the invention can be formulated into oral or parenteral dosage forms such as tablets, pills, capsules, granules, powders, solutions, emulsions, suspensions, ointments, creams, injections, or skin patches.

According to some embodiments of the invention, the pharmaceutical composition of the invention comprises the compound of the invention, a pharmaceutically acceptable salt, ester, solvate, isomer thereof, any crystalline form or racemate of the foregoing, a metabolite form of the foregoing, or a mixture of the foregoing, in an amount of 0.01 to 1000 mg, suitably 0.5 to 800 mg, preferably 1 to 400 mg, more preferably 5 to 200 mg, particularly preferably 10 to 100 mg, most preferably 15 to 50 mg, e.g., 20 mg, 25 mg or 30 mg. The pharmaceutical composition of the invention can be in the form of an unit dosage form, which can contain 0.01 to 1000 mg, suitably 0.5 to 800 mg, preferably 1 to 400 mg, more preferably 5 to 200 mg, particularly preferably 10 to 100 mg, most preferably 15 to 50 mg, e.g., 20 mg, 25 mg or 30 mg of the compound of the invention, a pharmaceutically acceptable salt, ester, solvate, isomer thereof, any crystalline form or racemate of the foregoing, a metabolite form of the foregoing, or a mixture of the foregoing.

According to some embodiments of the invention, the compound of the invention, a pharmaceutically acceptable salt, ester, solvate, isomer thereof, any crystalline form or racemate of the foregoing, a metabolite form of the foregoing, or a mixture of the foregoing can be combined with one or more additional active ingredients to treat, prevent, inhibit or ameliorate a disease or condition, wherein the combined use of the drugs offer more safety or effectiveness than the separate use of either drug.

Such an addition drug can be administered simultaneously or sequentially with the compound of the invention in a route and amount conventionally used for this purpose. When the compound of the invention, a pharmaceutically acceptable salt, ester, solvate, isomer thereof, any crystalline form or racemate of the foregoing, a metabolite form of the foregoing, or a mixture of the foregoing is used with one or more other drugs at the same time, a pharmaceutical composition comprising said other drug(s) and the compound of the invention in a unit dosage form is preferred, especially in combination with a pharmaceutically acceptable carrier. However, combined therapy can also contemplate administering the compound of the invention, a pharmaceutically acceptable salt, ester, solvate, isomer, any crystalline form or racemate of the foregoing, a metabolite form of the foregoing, or a mixture of the foregoing, and one or more other medications in different overlapping schedules. It is also contemplated that when used in combination with one or more additional active ingredients, the compound of the invention and the additional active ingredients can be used in lower doses than the doses when they are used individually. Thus, the pharmaceutical composition of the invention can also comprise one or more additional active ingredients in addition to the compound of the invention.

In some preferred embodiments, the additional active ingredients include, but are not limited to, interferons, ribavirin or analogues thereof, HCV NS3 protease inhibitors, α-glucosidase 1 inhibitors, hepatoprotective agents, non-nucleoside inhibitors of HCV NS5B polymerase, HCV NS5A inhibitors, TLR-7 agonists, cyclophilin inhibitors, HCV IRES inhibitors, pharmacokinetic enhancers, and other drugs or therapeutic agents for the treatment of HCV, or a combination thereof.

The interferon is selected from the group consisting of PEGylated rIFN-α2b (PEG-Intron®), PEGylated rIFN-α2a (Pegasys®), rIFN-α2b (Intron® A), rIFN-α2a (Roferon®-A), interferon α (MOR-22, OPC-18, Alfaferone, Alfanative, Multiferon, subalin), interferon alfacon-1 (Infergen®), interferon α-n1 (Wellferon), interferon α-n3 (Alferon®), interferon β (Avonex DL-8234), interferon-ω (ω DUROS®, Biomed510), albinterferonα-2b (Albuferon®), IFNα-2bXL, BLX-883 (Locteron®), DA-3021, glycosylated interferon α2b (AVI-005), PEG-Infergen, PEGylated interferon λ-1 (PEGylated IL-29) and Belerofon®.

The ribavirin and analogues thereof are selected from the group consisting of ribavirin (Rebetol®, Copegus®) and taribavirin (Viramidine®).

The HCV NS3 protease inhibitor is selected from the group consisting of boceprevir (SCH-503034, SCH-7), telaprevir (VX-950), TMC435350, BI-1335, BI-1230, MK-7009, VBY-376, VX-500, GS-9256, GS-9451, BMS-605339, PHX-1766, AS-101, YH-5258, YH5530, YH5531, ABT-450, ACH-1625, ITMN-191, MK5172, MK6325 and MK2748.

The α-glucosidase 1 inhibitor is selected from the group consisting of celgosivir (MX-3253), miglitol and UT-231B.

The hepatoprotective agent is selected from the group consisting of emericasna (IDN-6556), ME-3738, GS-9450 (LB-84451), silibilin and MitoQ.

The non-nucleoside inhibitor of HCV NS5B polymerase is selected from the group consisting of PF-868554, VCH-759, VCH-916, JTK-652, MK-3281, GS-9190, VBY-708, VCH-222, A848837, ANA-598, GL60667, GL59728, A-63890, A-48773, A-48547, BC-2329, VCH-796 (nesbuvir), GSK625433, BILN-1941, XTL-2125, ABT-072, ABT-333, GS-9669, PSI-7792 and GS-9190.

The HCV NS5A inhibitor is selected from the group consisting of ABT-267 (ombitasvir), AZD-2836 (A-831), BMS-790052, ACH-3102, ACH-2928, GS-5885, GS-5816, MK8325, MK4882, MK8742, PSI-461, IDX719 and A-689.

The TLR-7 agonist is selected from the group consisting of imiquimod, 852A, GS-9620, ANA-773, ANA-975, AZD-8848 (DSP-3025) and SM-360320.

The cyclophilin inhibitor is selected from the group consisting of DEBIO-025, SCY-635 and NIM811.

The HCV IRES inhibitor is selected from the group consisting of MCI-067.

The pharmacokinetic enhancer is selected from the group consisting of BAS-100, SPI-452, PF-4194477, TMC-41629, GS-9350, GS-9585 and roxithromycin.

The other drugs for the treatment of HCV are selected from the group consisting of thymosin a1 (Zadaxin), nitazoxanide (Alinea, NTZ), BIVN-401 (virostat), PYN-17 (altirex), KPE02003002, actilon (CPG-10101), GS-9525, KRN-7000, civacir, GI-5005, XTL-6865, BIT225, PTX-111, TX2865, TT-033i, ANA971, NOV-205, tarvacin, EHC-18, VGX-410C, EMZ-702, AVI4065, BMS-650032, BMS-791325, Bavituximab, MDX-1106 (ONO-4538), Oglufanide and VX-497 (merimepodib).

Method of Treatment and Use

The compound of the invention, a pharmaceutically acceptable salt, ester, solvate, isomer thereof, any crystalline form or racemate of the foregoing, a metabolite form of the foregoing, or a mixture of the foregoing can inhibit NS5B polymerase, DNA polymerase or reverse transcriptase. Thus, the compound of the invention, a pharmaceutically acceptable salt, ester, solvate, isomer thereof, any crystalline form or racemate of the foregoing, a metabolite form of the foregoing, or a mixture of the foregoing is useful as a NS5B polymerase inhibitor, a DNA polymerase inhibitor or a reverse transcriptase inhibitor.

Another object of the present invention is to provide use of the compound of the invention, a pharmaceutically acceptable salt, ester, solvate, isomer thereof, any crystalline form or racemate of the foregoing, a metabolite form of the foregoing, or a mixture of the foregoing, or a pharmaceutical composition of the invention in the manufacture of a medicament for the treatment of a NS5B polymerase mediated disease, a DNA polymerase mediated disease or a reverse transcriptase mediated disease.

Another object of the present invention is to provide use of the compound of the invention, a pharmaceutically acceptable salt, ester, solvate, isomer thereof, any crystalline form or racemate of the foregoing, a metabolite form of the foregoing, or a mixture of the foregoing, or the pharmaceutical composition of the invention in the manufacture of a medicament for the treatment of a viral disease or cancer.

Another object of the present invention is to provide the compound of the invention, a pharmaceutically acceptable salt, ester, solvate, isomer thereof, any crystalline form or racemate of the foregoing, a metabolite form of the foregoing, or a mixture of the foregoing, or the pharmaceutical composition of the invention for use in the treatment of a NS5B polymerase mediated disease, a DNA polymerase mediated disease or a reverse transcriptase mediated disease.

Another object of the present invention is to provide the compound of the invention, a pharmaceutically acceptable salt, ester, solvate, isomer thereof, any crystalline form or racemate of the foregoing, a metabolite form of the foregoing, or a mixture of the foregoing, or the pharmaceutical composition of the invention for use in the treatment of a viral disease or cancer.

Another object of the invention is to provide a method for treating a NS5B polymerase mediated disease, a DNA polymerase mediated disease or a reverse transcriptase mediated disease, comprising administering to a subject in need thereof an effective amount of the compound of the invention, a pharmaceutically acceptable salt, ester, solvate, isomer thereof, any crystalline form or racemate of the foregoing, a metabolite form of the foregoing, or a mixture of the foregoing, or the pharmaceutical composition of the invention.

Another object of the present invention is to provide a method for treating a viral disease or cancer, comprising administering to a subject in need thereof an effective amount of the compound of the invention, a pharmaceutically acceptable salt, ester, solvate, isomer thereof, any crystalline form or racemate of the foregoing, a metabolite form of the foregoing, or a mixture of the foregoing, or the pharmaceutical composition of the invention.

According to some embodiments of the invention, the viral diseases that can be prevented or treated using the compound of the invention include, but are not limited to, viral hepatitis type A, viral hepatitis type B, viral hepatitis type C, influenza, herpes, and acquired immunodeficiency syndrome (AIDS), and related symptoms or diseases caused by the above diseases (such as inflammation, liver fibrosis, liver cirrhosis and liver cancer).

Generally, for an adult patient, the compound of the invention can be administered orally or parenterally, in a total dose of 0.001 to 1500 mg per day, preferably 0.01 to 1000 mg per day, more preferably 0.1 to 800 mg per day, particularly preferably 1 to 600 mg per day, e.g., 250 mg per day, 400 mg per day, 500 mg per day or 600 mg per day, once or divided into several times per day. It is noted that the dose of the compound of the invention can be appropriately increased or reduced depending on the type of the disease to be treated, the age, body weight, symptoms of the patient, and the like.

Preparation Method

Another object of the present invention is to provide a method for preparing a compound of the above Formula (1), and the method can be carried according to Scheme 1:

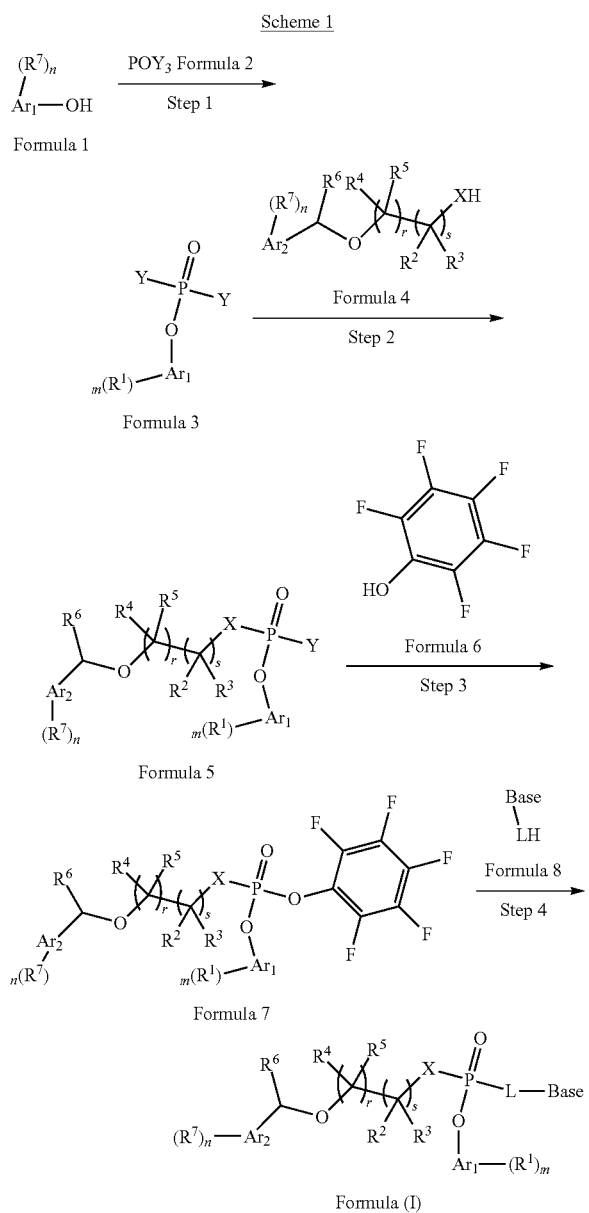

Scheme 1 wherein $R^1$, $R^2$, $R^3$, $R^4$, $R^5$, $R^6$, $R^7$, m, n, s, r, X, $Ar_1$, $Ar_2$, L-Base and Base are as defined above; and each Y is the same or different, and is each independently selected from halogen, preferably chloro.

Step 1: Reacting a Phosphorus Oxyhalide of Formula 2 with a Compound of Formula 1 to Obtain a Compound of Formula 3.

According to some embodiments of the invention, step 1 is carried out in the presence of an organic base.

According to some embodiments of the invention, step 1 comprises dissolving the phosphorus oxyhalide in an organic solvent, cooling to −80° C. to −20° C., and adding the compound of Formula 1 and an organic base. The reaction liquid is heated to 15° C. to 40° C., preferably 20° C. to 35° C., more preferably 25° C. to 30° C., and stirred for 1 to 8 h, preferably 2 to 6 h, to obtain a crude compound of Formula 3.

According to some embodiments of the invention, the molar ratio of the compound of Formula 1, phosphorus oxyhalide and the organic base is 1:(0.5 to 2):(0.5 to 2), preferably 1:(0.8 to 2):(0.8 to 2), and more preferably 1:(1 to 1.5):(1 to 1.5).

According to some embodiments of the invention, the weight to volume ratio (g/ml) of the compound of Formula 1 and the organic solvent is 1:5 to 30, preferably 1:10 to 25, and more preferably 1:15 to 20.

According to some embodiments of the invention, the weight to volume ratio (g/ml) of phosphorus oxyhalide and the organic solvent is 1:5 to 30, preferably 1:10 to 25, and more preferably 1:10 to 20.

According to some embodiments of the invention, the weight to volume ratio (g/ml) of the organic base and the organic solvent is 1:15 to 30, and preferably 1:20 to 25.

Step 2: Reacting the Compound of Formula 3 with a Compound of Formula 4 to Obtain a Compound of Formula 5.

According to some embodiments of the invention, step 2 comprises dissolving the compound of Formula 3 obtained in the first step in an organic solvent, cooling the reaction mixture to −80° C. to −20° C., and adding the compound of Formula 4 and an organic base. The temperature of the reaction mixture is raised to 15° C. to 40° C., preferably 20° C. to 35° C., and more preferably 25° C. to 30° C., and stirred for 1 to 8 h, and preferably 2 to 6 h. A crude compound of Formula 5 is obtained.

According to some embodiments of the invention, the molar ratio of the compound of Formula 3, the compound of Formula 4, and the organic base is 1:(0.5 to 1.5):(1.0 to 3.5), and preferably 1:(0.9 to 1.1):(1.4 to 3).

According to some embodiments of the invention, the weight to volume ratio (g/ml) of the compound of Formula 4 and the organic solvent is 1:(5 to 30), and preferably 1:(10 to 25).

According to some embodiments of the invention, the weight to volume ratio (g/ml) of the organic base and the organic solvent is 1:(3 to 25), and preferably 1:(5 to 20).

Step 3: Reacting the Compound of Formula 5 with Pentafluorophenol of Formula 6 to Obtain a Compound of Formula 7.

According to some embodiments of the invention, step 3 comprises dissolving the compound of Formula 5 obtained in step 2 in an organic solvent, cooling the reaction mixture to −80° C. to −20° C., and adding the compound of Formula 6 and an organic base sequentially thereto. The temperature of the reaction mixture is raised to 15° C. to 40° C., preferably 20° C. to 35° C., and more preferably 25° C. to 30° C., and stirred for 1 to 8 h, and preferably 2 to 6 h, to obtain the compound of Formula 7.

According to some embodiments of the invention, the molar ratio of the compound of Formula 5, the compound of Formula 6 and the organic base is 1:(0.5 to 2):(0.5 to 2.5), and preferably 1:(0.7 to 1.5):(1.0 to 2.0).

According to some embodiments of the invention, the weight to volume ratio (g/ml) of the compound of Formula 6 and the organic solvent is 1:(5 to 30), and preferably 1:(10 to 25).

According to some embodiments of the invention, the weight to volume ratio (g/ml) of the organic base and the organic solvent is 1:(10 to 30), and preferably 1:(15 to 25).

Step 4: Reacting the Compound of Formula 7 with a Compound of Formula 8 to Obtain a Compound of Formula (I).

According to some embodiments of the invention, step 4 comprises dissolving the compound of Formula 8 in an organic solvent, and adding a Grignard reagent to the reaction mixture at a temperature of 0° C. to 25° C. under the protection of an inert gas replacement. After stirring for 1 to 3 h, the temperature is lowered to −20° C. to −10° C., and the compound of Formula 7 obtained in step 3 is added. The temperature of the reaction mixture is raised to 1° C. to 40° C., and preferably 10° C. to 30° C., and stirred for 5 to 20 h, and preferably 10 to 15 h, to give the compound of Formula 1.

According to some embodiments of the invention, the molar ratio of the compound of Formula 7, the compound of Formula 8 and the Grignard reagent is 1:(0.8 to 2):(1.5 to 4), and preferably 1:(1 to 1.5):(2 to 3.5).

According to some embodiments of the invention, the weight to volume ratio (g/ml) of the compound of Formula 7 and the organic solvent is 1:(30 to 70).

According to some embodiments of the invention, the weight to volume ratio (g/ml) of the compound of Formula 8 and the organic solvent is 1:(90 to 120).

The organic bases used in the above steps 1, 2 and 3 include, but are not limited to, sodium t-butoxide, triethylamine, DIPEA, pyridine or DMAP.

The organic solvent used in the above steps 1, 2, 3 and 4 is a solvent commonly used in the art, such as, but not limited to, N,N-dimethylformamide, dimethyl sulfoxide, N-methylpyrrolidone, and saturated hydrocarbons (e.g., cyclohexane, hexane and the like), halogenated hydrocarbons (e.g., dichloromethane, chloroform, 1,2-dichloroethane and the like), ethers (e.g., tetrahydrofuran, diethyl ether, dioxane, 1,2-dimethoxyethane and the like), nitriles (e.g., acetonitrile and the like), a mixed solvent thereof, and the like.

Alternatively, the method can be carried out according to Scheme 2:

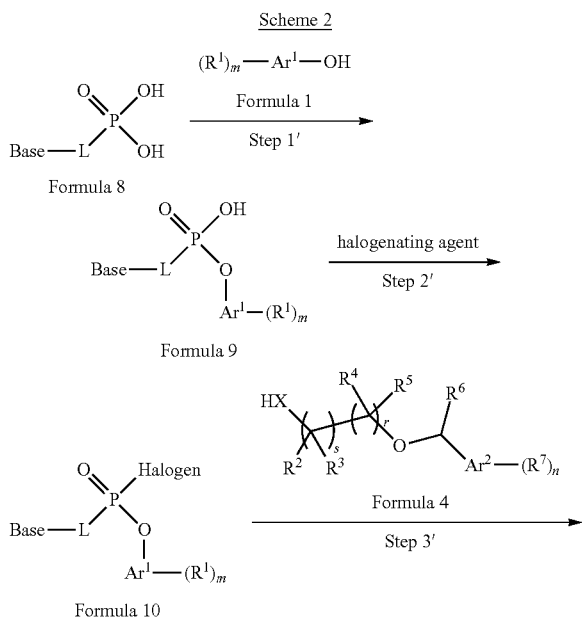

Scheme 2

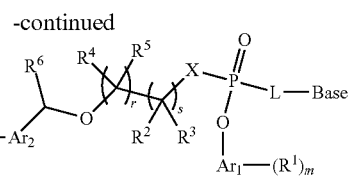

Formula (I)

wherein $R^1$, $R^2$, $R^3$, $R^4$, $R^5$, $R^6$, $R^7$, m, n, s, r, X, $Ar_1$, $Ar_2$, L and Base are as defined above.

Step 1':

According to some embodiments of the invention, step 1' is carried out in the presence of an organic or inorganic base and/or a condensation reagent. The organic base includes, but is not limited to, sodium t-butoxide, triethylamine, DIPEA, pyridine or DMAP. The inorganic base includes, but is not limited to, NaH, NaOH, $Na_2CO_3$ or $K_2CO_3$. The condensation reagent includes, but is not limited to, DCC, DIC, EDC, BOP, PyAOP and PyBOP.

According to some embodiments of the invention, the compound of Formula 1 is phenol or naphthol.

According to some embodiments of the invention, step 1' is carried out at a temperature of 60° C. to 150° C., preferably 70° C. to 130° C., and more preferably 80° C. to 110° C.

According to some embodiments of the invention, the molar ratio of the compound of Formula 8 and the compound of Formula 1 is 1:(0.5 to 2), preferably 1:(0.8 to 2), and more preferably 1:(1 to 1.5).

According to some embodiments of the invention, the molar ratio of the compound of Formula 8, the compound of Formula 1 and the organic or inorganic base is 1:(0.5 to 2):(0.5 to 2), preferably 1:(0.8 to 2):(0.8 to 2), and more preferably 1:(1 to 1.5):(1 to 1.5).

According to some embodiments of the invention, the molar ratio of the compound of Formula 8 and the condensation reagent is 1:(1.5 to 3), and preferably 1:(1.8 to 2.5).

Step 2':

According to some embodiments of the invention, the halogenating agent is a chlorinating or brominating agent, preferably a chlorinating agent, and more preferably $SOCl_2$.

According to some embodiments of the invention, step 2' is carried out at a temperature of −20° C. to 150° C., preferably 50° C. to 110° C., further preferably 50° C. to 90° C., and more preferably 60 to 80° C.

According to some embodiments of the invention, the molar ratio of the compound of Formula 9 and the halogenating agent is 1:(2 to 10), preferably 1:(3 to 10), and more preferably 1:(4 to 8).

Step 3':

According to some embodiments of the invention, step 3' is carried out in the presence of an organic or inorganic base. The organic base includes, but is not limited to, sodium t-butoxide, triethylamine, DIPEA, pyridine or DMAP. The inorganic base includes, but is not limited to, NaH, NaOH, $Na_2CO_3$ or $K_2CO_3$.

According to some embodiments of the invention, step 3' is carried out at a temperature of −78° C. to 25° C., preferably −40° C. to 0° C., and more preferably −30° C. to 10° C.

According to some embodiments of the invention, the molar ratio of the compound of Formula 10 and the compound of Formula 4 is 1:(1 to 10), preferably 1:(1 to 3), and more preferably 1:(1.5 to 2.5).

According to some embodiments of the invention, the molar ratio of the compound of Formula 10, the compound of Formula 4 and the organic or inorganic base is 1:(1 to 10):(5 to 20), preferably 1:(1 to 3):(5 to 20), and more preferably 1:(1.5 to 2.5):(8 to 15).

The above steps 1', 2' and 3' can be carried out in an organic solvent. The organic solvent can be a reaction solvent commonly used in the art, such as, but not limited to, N,N-dimethylformamide, dimethyl sulfoxide, N-methylpyrrolidone, and saturated hydrocarbons (e.g., cyclohexane, hexane and the like), halogenated hydrocarbons (e.g., dichloromethane, chloroform, 1,2-dichloroethane and the like), ethers (e.g., tetrahydrofuran, diethyl ether, dioxane, 1,2-dimethoxyethane and the like), nitriles (e.g., acetonitrile and the like), a mixed solvent thereof, and the like.

The present invention also provides a method for synthesizing a chirally pure phosphorus compound of Formula (I″), which can be carried out according to Scheme 3:

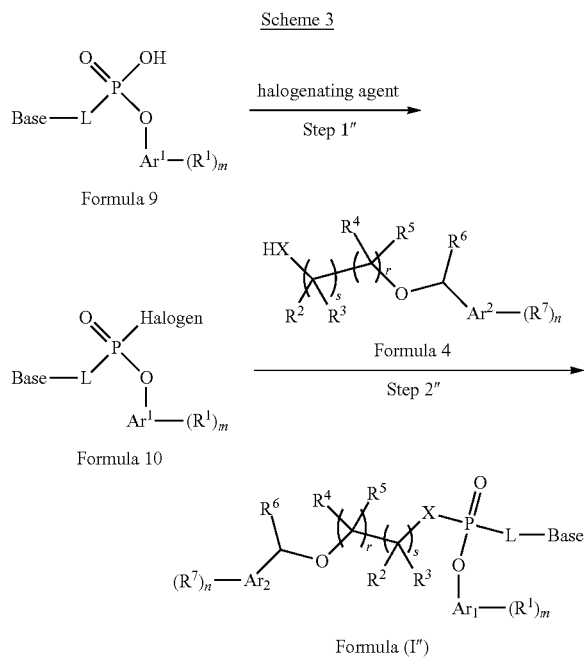

wherein
 represents either a solid wedge ( ) or dashed wedge ( ) chemical bond; and
$R^1$, $R^2$, $R^3$, $R^4$, $R^5$, $R^6$, $R^7$, m, n, s, r, X, $Ar_1$, $Ar_2$, L and Base are as defined above.

Step 1″: Halogenating a Compound of Formula 9 to Produce a Compound of Formula 11.

According to some embodiments of the invention, the halogenating agent is thionyl chloride, oxalyl chloride, phosphorus trichloride, triphenylphosphonium chloride, thionyl bromide, oxalyl bromide, phosphorus tribromide or triphenylphosphonium bromide, and preferably thionyl chloride.

According to some embodiments of the invention, step 1″ is carried out at a temperature of −20° C. to 150° C., preferably 25° C. to 120° C., and more preferably 50 to 110° C.

According to some embodiments of the invention, the reaction time of step 1″ is 12 h to 96 h, and preferably 36 h to 72 h.

According to some embodiments of the invention, the molar ratio of the compound of Formula 9 to the halogenating agent is 1:(2 to 10), and preferably 1:(3 to 6).

Step 2″: Reacting a Compound of Formula 11 with a Compound of Formula 4 to Produce a Compound of Formula (F′).

According to some embodiments of the invention, step 2″ is carried out at a temperature of −78° C. to 25° C., and preferably −40° C. to 0° C.

According to some embodiments of the invention, the molar ratio of the compound of Formula 12 to the compound of Formula 4 is 1:(1 to 10), and preferably 1:(1 to 5).

The above steps 1″ and 2″ can be carried out in an organic solvent. The organic solvent can be a reaction solvent commonly used in the art, such as, but not limited to, N,N-dimethylformamide, dimethyl sulfoxide, N-methylpyrrolidone, esters (e.g., methyl acetate, ethyl acetate, propyl acetate and the like), saturated hydrocarbons (e.g., cyclohexane, hexane and the like), halogenated hydrocarbons (e.g., dichloromethane, chloroform, 1,2-dichloroethane and the like), ethers (e.g., tetrahydrofuran, diethyl ether, diisopropyl ether, dioxane, 1,2-dimethoxyethane and the like), benzenes (e.g., toluene, xylene and the like), nitriles (e.g., acetonitrile and the like), a mixed solvent thereof, and the like.

The compound of Formula (I) as obtained above can be isolated by preparative high performance liquid chromatography to afford an isomer. The resulting isomers can be in the form of enantiomers, diastereomers and the like.

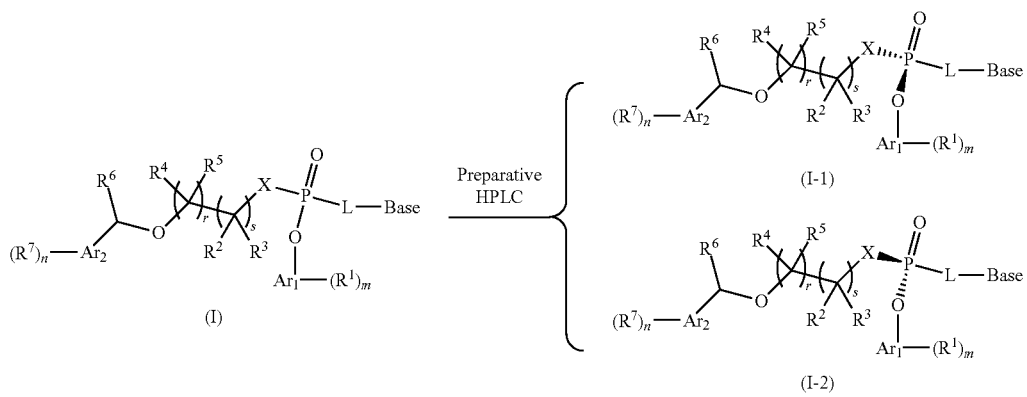

EXAMPLES

For illuminating the objects and technical solutions of the invention, the invention will be further illustrated with specific examples. It is to be understood that these examples are only illustrative but not intended to limit the scope of the invention. Further, the specific experimental methods not mentioned in the following examples were carried out in accordance with conventional ways. Both the starting materials and the reagents for the synthesis in the present invention are commercially available.

The abbreviations herein have the following meanings:

TABLE 1

Meanings of English abbreviations

| Abbreviation | Meaning |
| --- | --- |
| DMAP | 4-dimethylaminopyridine |
| DIPEA | N,N-diisopropylethylamine |
| DCC | dicyclohexylcarbodiimide |
| DIC | N,N-diisopropylcarbodiimide |
| EDC | 1-(3-dimethylaminopropyl)-3-ethylcarbodiimide |
| BOP | benzotriazol-1-yloxytris(dimethylamino)phosphonium hexafluorophosphate |
| PyAOP | (3H-1,2,3-triazolo[4,5-b]pyridine-3-oxy)tri-1-pyrrolidinylphosphonium hexafluorophosphate |
| PyBOP | 1H-benzotriazol-1-yl-oxytripyrrolidinylphosphonium hexafluorophosphate |
| CD$_3$OD | deuterated methanol |
| CDCl$_3$ | deuterated chloroform |
| DMSO-d$_6$ | dimethyl sulfoxide-d$_6$ |
| TMS | tetramethylsilane |
| NMR | nuclear magnetic resonance |
| MS | mass spectrometry |
| IPA | isopropanol |
| TEA | triethylamine |
| s | singlet |
| s | singlet |
| d | doublet |
| t | triplet |
| q | quartet |
| dd | double doublet |

TABLE 1-continued

Meanings of English abbreviations

| Abbreviation | Meaning |
| --- | --- |
| qd | quartet doublet |
| ddd | double double doublet |
| ddt | double double triplet |
| dddd | double double double doublet |
| m | multiplet |
| br | broad |
| J | coupling constant |
| Hz | Hertz |
| Rt | retention time in liquid chromatography |
| MC | dichloromethane |
| LC-MS | liquid chromatography-mass spectrometry |

The structure of the compound described in the following examples was determined by $^1$H NMR or MS. $^1$H NMR was determined using JEOL Eclipse 400 NMR Spectrometer; the solvent was CD$_3$OD, CDCl$_3$ or DMSO-d$_6$; and the internal standard was TMS. All δ values are expressed in ppm. MS was determined using Agilent (ESI) mass spectrometer, model Agilent 6120B.

The mixture of diastereomers prepared in the examples can be separated by preparative high performance liquid chromatography to obtain pure isomers. The separation by preparative high performance liquid chromatography can be carried out according to methods known in the art, e.g., under the following separation conditions: filler—octadecyl bonded silica, column temperature—30 to 50° C., flow rate—5.0 to 20.0 mL/min, detection wavelength—200 to 400 nm, linear gradient elution with mobile phase A (e.g., water) and mobile phase B (e.g., methanol or acetonitrile).

Example 1

((2R,3R,4R,5R)-5-(2,4-dioxo-3,4-dihydropyrimidin-1(2H)-yl)-4-fluoro-3-hydroxy-4-methyltetrahydrofuran-2-yl)methyl-phenyl-((S)-1-(2-methylbenzyloxy)propan-2-yl)phosphoramidate (Compound 2-1)

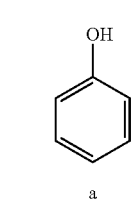

a

POCl$_3$

Step 1

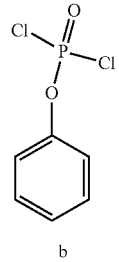

b

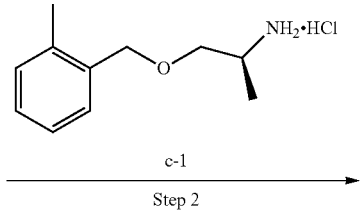

c-1

Step 2

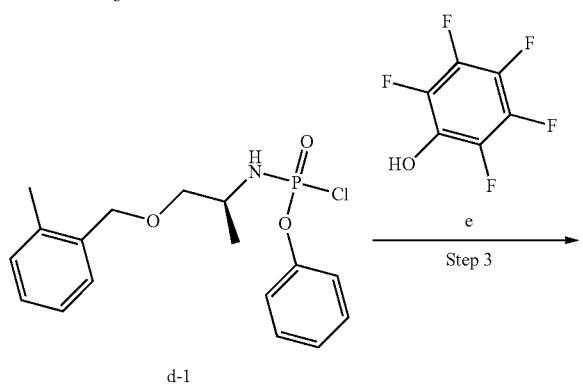

d-1

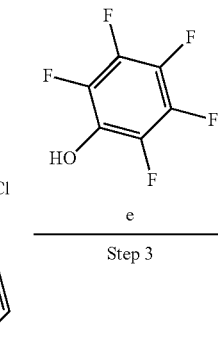

e

Step 3

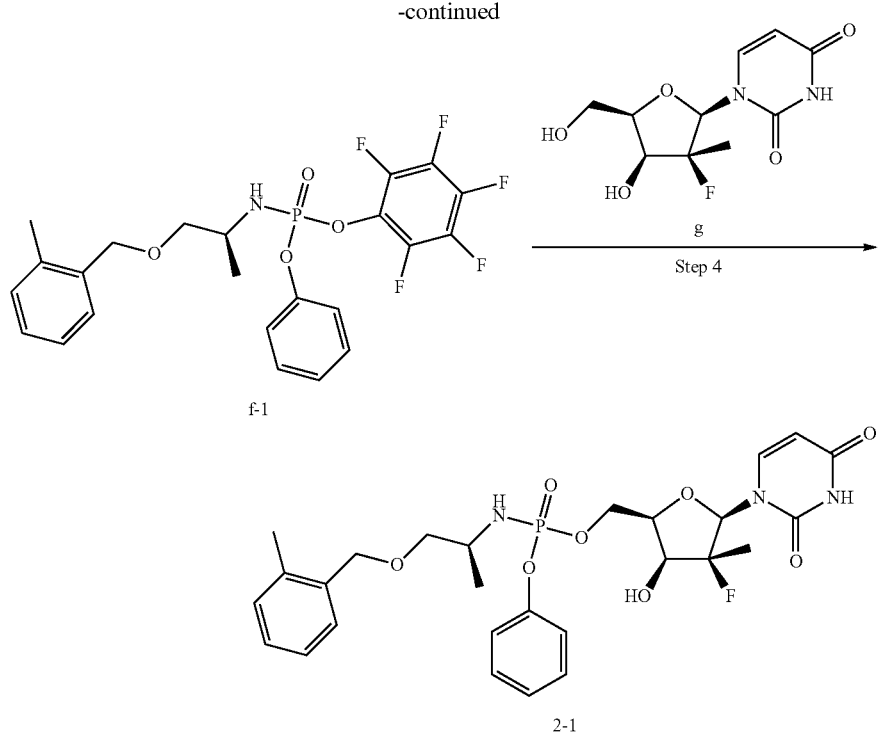

Step 1 to Step 3: (S)-pentafluorophenyl-phenyl-(1-(2-methylbenzyloxy)propan-2-yl)phosphoramidate (Compound f-1)

Phosphorus oxychloride (1.53 g, 10 mmol) was dissolved in dichloromethane (10 mL), and was cooled to −70° C. A solution of phenol (Compound a, 0.94 g, 10 mmol) and triethylamine (1.01 g, 10 mmol) in dichloromethane (10 mL) was added dropwise. After the completion of the dropwise addition, the cooling bath was removed, and the temperature was allowed to reach room temperature. After stirring for 2 hours (h), a standby reaction mixture was obtained. To (S)-1-(2-methylbenzyloxy)propan-2-ylamine hydrochloride (Compound c-1, 2.16 g, 10 mmol) was added dichloromethane (40 mL), and the temperature was lowered to −70° C. under nitrogen protection. A solution of triethylamine (1.01 g, 10 mmol) in dichloromethane (10 mL) was added dropwise to the reaction system. After the completion of the dropwise addition, the above standby reaction mixture was added dropwise to the reaction system. After completion of the dropwise addition, the mixture was stirred at −70° C. for 90 minutes. The cooling bath was removed, and the temperature was allowed to reach 20° C. The mixture was stirred for 3 h. The reaction system was further cooled to −70° C., and a solution of pentafluorophenol (Compound e, 1.66 g, 9 mmol) in dichloromethane (10 mL) was added dropwise, and then a solution of triethylamine (1.52 g, 15 mmol) in dichloromethane (10 mL) was added dropwise. After completion of the dropwise addition, the cooling bath was removed, and the temperature was allowed to reach 25° C. The mixture was stirred overnight. After the reaction was completed, the reaction system was poured into ice water, and extracted with dichloromethane. The organic phases were combined, washed with a saturated NaCl aqueous solution, dried, filtered, and concentrated to afford (S)-pentafluorophenyl-phenyl-(1-(2-methylbenzyloxy)propan-2-yl)phosphoramidate (Compound f-1).

Step 4: ((2R,3R,4R,5R)-5-(2,4-dioxo-3,4-dihydropyrimidin-1(2H)-yl)-4-fluoro-3-hydroxy-4-methyltetrahydrofuran-2-yl)methyl-phenyl-((S)-1-(2-methylbenzyloxy)propan-2-yl)phosphoramidate 1-((2R,3R,4R,5R)-3-fluoro-4-hydroxy-5-hydroxymethyl-3-methyltetrahydrofuran-2-yl)pyrimidine-2,4-(1H,3H)-dione (Compound g, 260 mg, 1 mmol) was dissolved in anhydrous tetrahydrofuran (20 mL) under argon protection. A solution of tert-butyl magnesium chloride (1.0 mol/L, 2.5 mL, 2.5 mmol) was added dropwise at 0° C. The temperature was allowed to reach 30° C., and the reaction was carried out for 1 hour. The temperature was lowered to 0° C., and a solution of Compound f-1 (502 mg, 1 mmol) in anhydrous tetrahydrofuran (10 mL) was added dropwise. After the completion of the dropwise addition, the temperature was allowed to reach 25° C., and the reaction was carried out for 10 h. The temperature of the reaction system was lowered to −5° C., adjusted to pH 4-5 with 2 M hydrochloric acid, and poured into ice water. The reaction system was extracted with EtOAc, and the organic phases were combined, washed respectively with a saturated NaHCO$_3$ aqueous solution and a saturated NaCl aqueous solution, dried, filtered, and concentrated to afford the title compound 2-1 (440 mg, yield 76%).

Structural Characterization:

$^1$H NMR (CDCl$_3$, 400 MHz) δ 9.06 (s, 1H), 7.42-7.12 (m, 10H), 6.15 (d, J=18.8 Hz, 1H), 5.52 (dd, J=8.3, 3.3 Hz, 1H), 4.58-4.29 (m, 4H), 4.04 (d, J=9.4 Hz, 1H), 3.53-3.47 (m, 2H), 3.45-3.35 (m, 2H), 2.31 (s, 3H), 1.38 (d, J=3.6 Hz, 3H), 1.29-1.10 (d, J=3.2 Hz, 3H).

$^{31}$P NMR (CDCl$_3$, 162 MHz) δ 4.36.

ESI-MS: m/z 578.2 [M+H]$^+$.

Example 2
(((2R,3R,4R,5R)-5-(2,4-dioxo-3,4-dihydropyrimidin-1(2H)-yl)-4-fluoro-3-hydroxy-4-methyl tetrahydrofuran-2-yl)methyl-phenyl-((R)-1-(2-methylbenzyloxy)propan-2-yl)phosphoramidate (Compound 2-2)
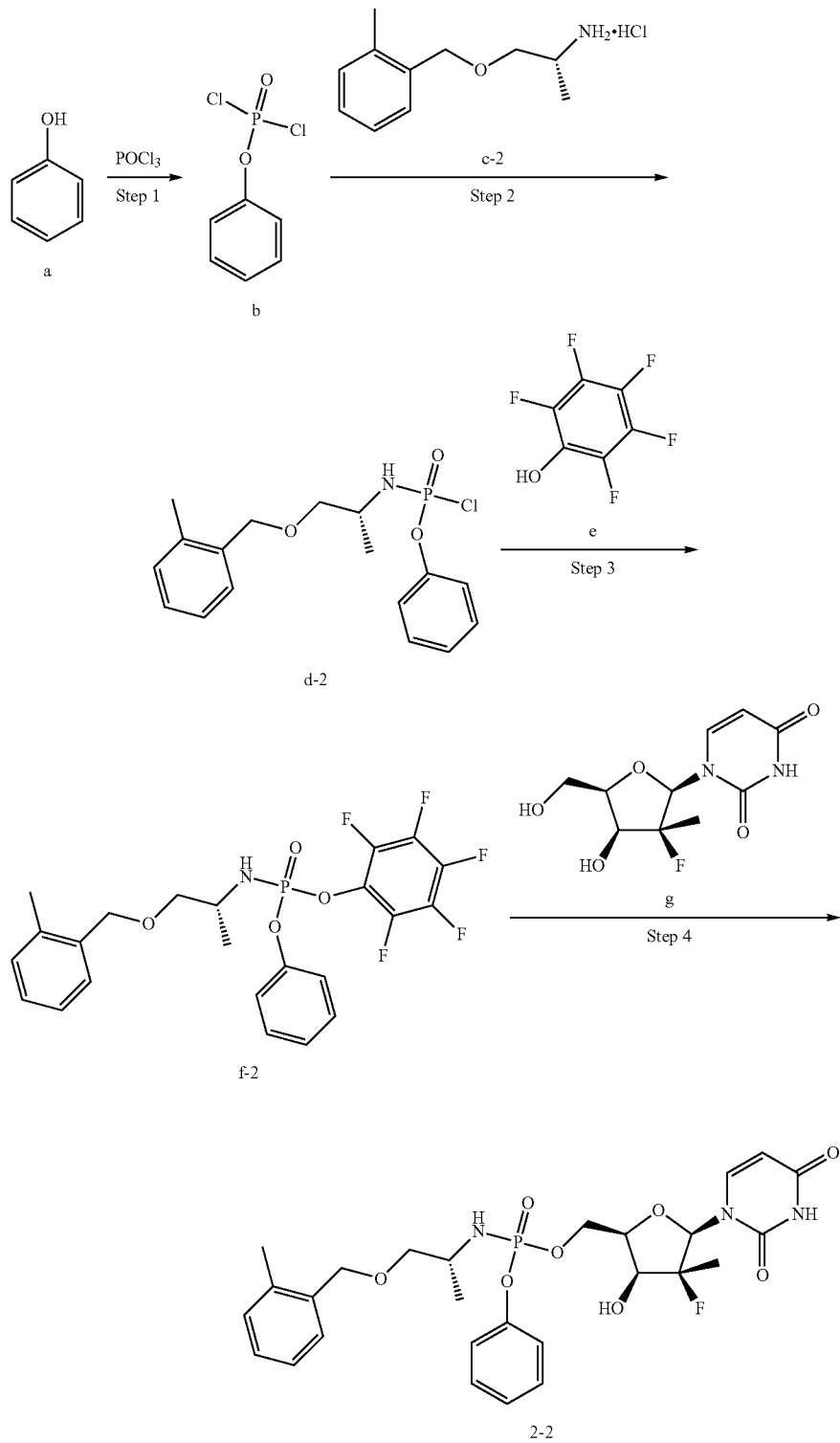

Step 1 to Step 3: (R)-pentafluorophenyl-phenyl-(1-(2-methylbenzyloxy)propan-2-yl)phosphoramidate (Compound f-2)

Phosphorus oxychloride (475 mg, 3.1 mmol) was added to dichloromethane (10 mL), and the temperature was lowered to −70° C. under nitrogen protection. A solution of phenol (Compound a, 292 mg, 3.1 mmol) and triethylamine (314 mg, 3.1 mmol) in dichloromethane was added dropwise. After completion of the dropwise addition, the reaction was carried out at −70° C. for 5 minutes, and then the temperature was allowed to reach room temperature. After stirring for 2 h, a standby reaction mixture was obtained. Methylene chloride (20 mL) was added to (R)-1-(2-methylbenzyloxy)propan-2-ylamine hydrochloride (Compound c-2, 500 mg, 2.79 mmol), and the temperature was lowered to −70° C. under nitrogen protection. A solution of triethylamine (314 mg, 3.1 mmol) in dichloromethane (3 mL) was added dropwise to the reaction system. After the completion of the dropwise addition, the mixture was stirred for 5 minutes to afford a reaction system. The above standby reaction mixture was added dropwise to the reaction system. After completion of the dropwise addition, the mixture was stirred at −70° C. for 90 minutes. The temperature was then allowed to reach 0° C. The mixture was stirred for 2 h, and finally the temperature of the reaction system was lowered to −70° C. A solution of pentafluorophenol (Compound e, 514 mg, 2.79 mmol) in dichloromethane (5 mL) was added dropwise to the reaction system, and after completion of the dropwise addition, the mixture was stirred for 5 minutes. A solution of triethylamine (374 mg, 3.7 mmol) in dichloromethane (5 mL) was added dropwise, and after completion of the dropwise addition, the mixture was stirred for 5 min. The temperature was allowed to reach room temperature, and the mixture was stirred overnight. Water (30 mL) was added to the reaction mixture, and the layers were separated. The aqueous phase was extracted with dichloromethane. The organic phases were combined, washed twice with a saturated NaCl solution, dried, filtered, and concentrated to afford (R)-pentafluorophenyl-phenyl-(1-(2-methylbenzyloxy)propan-2-yl)phosphoramidate (Compound f-2).

Step 4: ((2R,3R,4R,5R)-5-(2,4-dioxo-3,4-dihydro-pyrimidin-1(2H)-yl)-4-fluoro-3-hydroxy-4-methyl-tetrahydrofuran-2-yl)methyl-phenyl-((R)-1-(2-methylbenzyloxy)propan-2-yl)phosphoramidate 1-((2R,3R,4R,5R)-3-fluoro-4-hydroxy-5-hydroxymethyl-3-methyltetrahydrofuran-2-yl)pyrimidine-2,4-(1H,3H)-diketone (Compound g, 605 mg, 2.3 mmol) was dissolved in tetrahydrofuran (30 mL), and the temperature was lowered to −20° C. under nitrogen protection. A solution of tert-butyl magnesium chloride (4.9 mL, 4.9 mmol) was added dropwise at −20° C. After the completion of the dropwise addition, the mixture was stirred at −20° C. for 30 minutes. The cooling bath was removed, and the reaction system was allowed to warm to room temperature. The mixture was stirred for 2 h and then the temperature was lowered to −5° C. A solution of Compound f-2 (671 mg, 3.1 mmol) in tetrahydrofuran (10 mL) was added dropwise to the reaction system. After completion of the dropwise, the mixture was stirred at −5° C. for 1 h. The cooling bath was removed, and the temperature was allowed to reach room temperature. The mixture was stirred overnight. The temperature of the reaction system was lowered to −5° C., adjusted to pH 4-5 with 2 M hydrochloric acid, and poured into ice water. Ethyl acetate was added, and the mixture was stirred and subjected to liquid separation. The aqueous phase was extracted with EtOAc, and the organic phases were combined, washed respectively with a saturated NaHCO$_3$ aqueous solution and a saturated NaCl aqueous solution, dried, filtered, concentrated, and purified to afford the title compound 2-2 (460 mg, yield 28.5%).

Structural Characterization:

$^1$H NMR (400 MHz, Chloroform-d) δ 8.63 (s, 1H), 7.54-7.29 (m, 3H), 7.24-7.11 (m, 6H), 6.13 (d, J=18.77 Hz, 1H), 5.59 (d, J=8.10 Hz, 1H), 4.45 (dd, J=16.62, 10.12 Hz, 4H), 4.18-3.17 (m, 6H), 2.31 (d, J=10.07 Hz, 3H), 1.52-1.09 (m, 6H).

ESI-MS (m/z): 578.2 [M+H]$^+$.

Example 3

((2R,3R,4R,5R)-5-(2,4-dioxo-3,4-dihydropyrimidin-1(2H)-yl)-4-fluoro-3-hydroxy-4-methyl tetrahydrofuran-2-yl)methyl-phenyl-(2-methyl-1-(2-methylbenzyloxy)propan-2-yl)phosphoramidate (Compound 3)

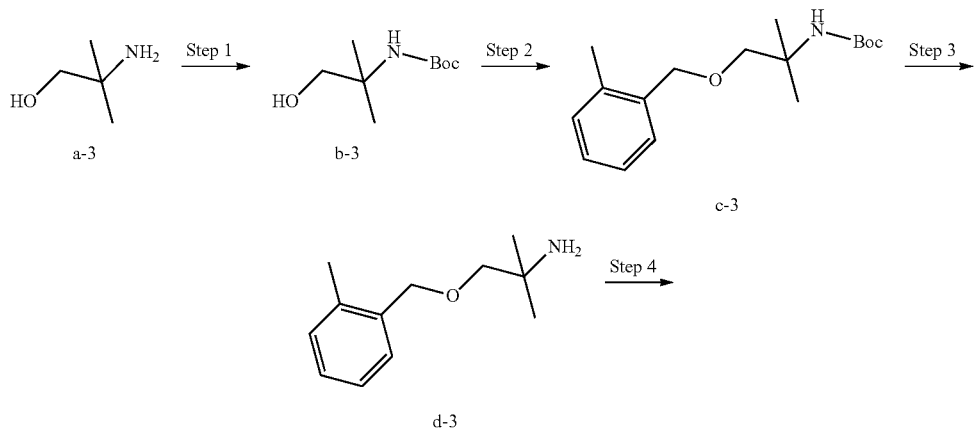

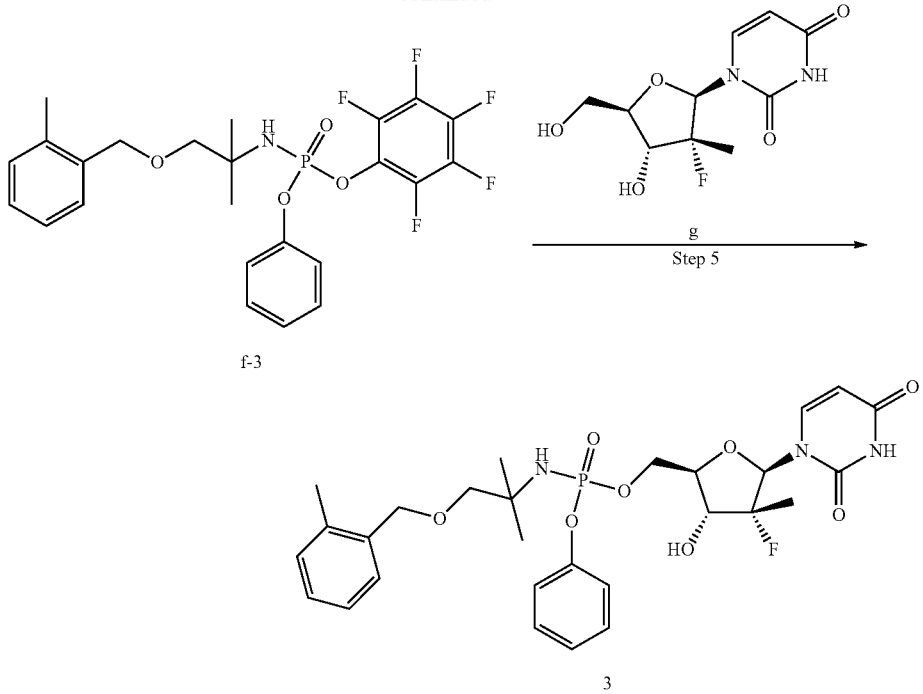

Step 1: Synthesis of N-Boc-2-amino-2-methyl-1-propanol (Compound b-3)

Potassium carbonate (31.5 g, 225 mmol) was added to water (150 mL), and dissolved upon stirring, to give a reaction mixture. 2-amino-2-methyl-1-propanol (Compound a-3, 13.35 g, 150 mmol) was dissolved in tetrahydrofuran (50 mL), and the resulting solution was added to the above reaction mixture. Then, a solution of di-tert-butyl dicarbonate (32.7 g, 150 mmol) in tetrahydrofuran was added dropwise and stirred at room temperature overnight. Ethyl acetate (50 mL) was added, and the layers were separated. The aqueous phase was extracted with ethyl acetate twice. The organic phases were combined, washed with a saturated NaCl solution, dried, and concentrated to afford Compound b-3 (28 g, yield 99%).

Step 2: Synthesis of N-Boc-(2-methyl-1-((2-methylbenzyloxy)propan-2-yl))amine (Compound c-3)

Compound b-3 (5.67 g, 30 mmol) was dissolved in N,N-dimethylformamide (60 mL), and the temperature was lowered to 5° C. under nitrogen protection. Sodium hydride (1.8 g, 45 mmol) was added. The mixture was stirred at 5° C. for 30 min. O-methylbenzyl bromide (5.83 g, 31.5 mmol) was added dropwise to the reaction system while keeping the temperature at 5° C. After completion of the dropwise addition, the mixture was stirred at 5° C. for 30 minutes. The cooling bath was removed, and the temperature was allowed to slowly reach room temperature. The mixture was stirred overnight. The reaction system was poured into ice water, and extracted twice with methyl t-butyl ether. The organic phase was washed with a saturated NaCl aqueous solution, dried, concentrated, and purified to afford Compound c-3 (2 g, yield 23%).

Step 3: Synthesis of 2-methyl-1-(2-methylbenzyloxy)propan-2-ylamine (Compound d-3)

Compound c-3 (2 g, 6.8 mmol) was added to a three-necked flask. Dichloromethane (30 mL) was added, and the temperature was lowered to 0° C. Trifluoroacetic acid (4.9 g, 34 mmol) was added dropwise, and the temperature was allowed to reach room temperature. The mixture was stirred overnight. The reaction was quenched, and the reaction mixture was poured into a saturated $NaHCO_3$ solution. NaCl solid was added for saturation, and the layers were separated and extracted with DCM, dried, and concentrated to afford Compound d-3 (1.2 g, yield 76%).

Step 4: Synthesis of pentafluorophenyl-phenyl-(2-methyl-1-(2-methylbenzyloxy)propan-2-yl)phosphoramidate (Compound f-3)

Phosphorus oxychloride (459 mg) was added to dichloromethane (10 mL), and the temperature was lowered to −70° C. under nitrogen protection. A solution of phenol (282 mg, 3 mmol) and triethylamine (303 mg, 3 mmol) in dichloromethane (3 mL) was added dropwise. After completion of the dropwise addition, the reaction was carried out at −70° C. for 5 min. Then, the temperature was allowed to reach room temperature. After stirring for 2 h, a standby reaction mixture was obtained. Dichloromethane (20 mL) was added to 2-methyl-1-(2-methylbenzyloxy)propan-2-ylamine (Compound d-3, 588 mg, 3.03 mmol), and the temperature was lowered to −70° C. under nitrogen protection. A solution of triethylamine (318 mg, 3.15 mmol) in dichloromethane (3 mL) was added dropwise, and after completion of the dropwise addition, a reaction system was obtained after stirring for 5 min. The above standby reaction mixture was added dropwise to the reaction system. After completion of the dropwise addition, the mixture was stirred at −70° C. for 90 minutes. Then the temperature was allowed to reach 0° C., and the mixture was stirred for 2 h. Finally, the temperature of the reaction system was lowered to −70° C., and a solution of pentafluorophenol (496 mg, 2.7 mmol) in dichloromethane (5 mL) was added dropwise to the reaction system at −70° C. After completion of the dropwise addition, the mixture was stirred for 5 min. A solution of triethylamine (363 mg, 3.6 mmol) in dichloromethane (5 mL) was added dropwise. After the completion of the dropwise addition, the mixture was stirred for 5 minutes, and the temperature was allowed to reach room temperature. The mixture was stirred overnight. Water (30 mL) was added to the reaction mixture, and the layers were separated. The aqueous phase was extracted with dichloromethane, and the organic phases were combined, washed with a saturated NaCl solution, dried, and concentrated to afford Compound f-3, which was directly used in the subsequent reaction.

Step 5: Synthesis of (2R,3R,4R,5R)-5-(2,4-dioxo-3,4-dihydropyrimidin-1(2H)-yl)-4-fluoro-3-hydroxy-4-methyltetrahydrofuran-2-yl)methyl-phenyl-(2-methyl-1-(2-methylbenzyloxy) propan-2-yl) phosphoramidate 1-((2R,3R,4R,5R)-3-fluoro-4-hydroxy-5-hydroxymethyl-3-methyltetrahydrofuran-2-yl)pyrimidine-2,4(1H,3H)-dione (Compound g, 650 mg, 2.5 mmol) was dissolved in tetrahydrofuran (30 mL), and the temperature was lowered to −20° C. under nitrogen protection. Teat-butyl magnesium chloride (5.25 mL, 5.25 mmol) was added dropwise at −20° C. After completion of the dropwise addition, the mixture was stirred at −20° C. for 30 minutes. The cooling bath was removed, and the temperature of the reaction system was allowed to reach room temperature. The mixture was stirred for 2 h, and then the temperature was lowered to −5° C. A solution of Compound f-3 (1.5 g, 3.0 mmol) in tetrahydrofuran (20 mL) was slowly added dropwise to the reaction system, and the mixture was stirred at −5° C. for 1 h. The cooling bath was removed, and the temperature was allowed to slowly reach room temperature. The mixture was stirred overnight. The temperature of the reaction system was lowered to −5° C., and pH was adjusted to pH 4-5 with 2 M hydrochloric acid. Then the mixture was poured into ice water. Ethyl acetate was added, and the mixture was stirred for 5 min. The layers were separated, and the aqueous phase was extracted with ethyl acetate. The organic phases were combined, washed successively with a saturated NaHCO$_3$ aqueous solution and a saturated NaCl aqueous solution, dried, concentrated, and purified to afford title compound 3 (100 mg, yield 5.5%)

The structure was characterized as follows:

$^1$H NMR (400 MHz, Chloroform-d) δ 8.80 (s, 1H), 7.44 (d, J=8.2 Hz, 1H), 7.32 (dd, J=8.6, 7.2 Hz, 2H), 7.20 (m, 7H), 6.15 (d, J=18.8 Hz, 1H), 5.59 (dd, J=8.1, 1.9 Hz, 1H), 4.60-4.35 (m, 4H), 4.07 (d, J=9.3 Hz, 1H), 3.90 (dd, J=23.1, 9.4 Hz, 1H), 3.65 (d, J=9.4 Hz, 1H), 3.32-3.18 (m, 2H), 2.31 (s, 3H), 1.43-1.24 (m, 9H).

ESI-MS (m/z): 592.2 [M+H]$^+$.

With reference to the synthesis method of Examples 1-3, the following compounds were obtained:

| Ex. | Structure | Compound name | M/Z |
| --- | --- | --- | --- |
| Ex. 4 (Compound 1) | 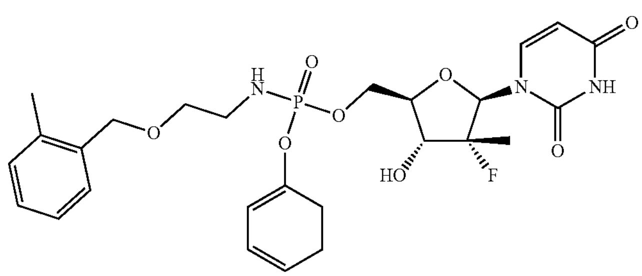 [SMILES: Cc1ccccc1COCCNP(=O)(OC[C@H]1O[C@@H](n2ccc(=O)[nH]c2=O)[C@](C)(F)[C@@H]1O)OC1=CC=CCC1] | ((2R,3R,4R,5R)-5-(2,4-dioxo-3,4-dihydropyrimidin-1(2H)-yl)-4-fluoro-3-hydroxy-4-methyltetrahydrofran-2-yl)methyl-phenyl-((2-methylbenzyloxy)ethyl) phosphoramidate | 564.2 [M + 1]$^+$ |
| Ex. 5 (Compound 4) | 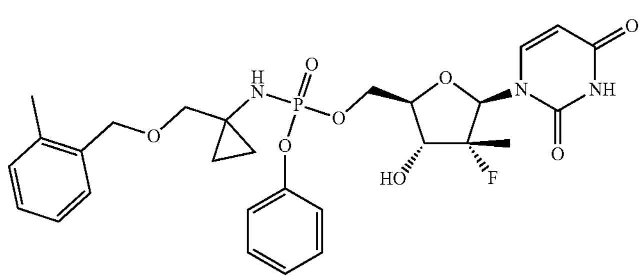 [SMILES: Cc1ccccc1COCC1(NP(=O)(OC[C@H]2O[C@@H](n3ccc(=O)[nH]c3=O)[C@](C)(F)[C@@H]2O)Oc2ccccc2)CC1] | (2R,3R,4R,5R)-5-(2,4-dioxo-3,4-dihydropyrimidin-1(2H)-yl)-4-fluoro-3-hydroxy-4-methyltetrahydrofuran-2-yl)methyl-phenyl-(1-((2-methylbenzyloxy)methyl)cycloprop-1-yl)phosphoramidate | 590.2 [M + 1]$^+$ |

-continued

| Ex. | Structure | Compound name | M/Z |
|---|---|---|---|
| Ex. 6 (Compound 5) | 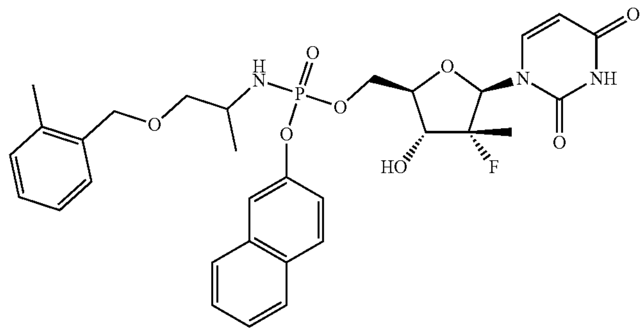 [SMILES: Cc1ccccc1COCC(C)NP(=O)(OC[C@H]1O[C@@H](n2ccc(=O)[nH]c2=O)[C@](C)(F)[C@@H]1O)Oc1ccc2ccccc2c1] | ((2R,3R,4R,5R)-5-(2,4-dioxo-3,4-dihydropyrimidin-1(2H)-yl)-4-fluoro-3-hydroxy-4-methyltetrahydrofuran-2-yl)methyl-naphth-2-yl-(1-(2-methylbenzyloxy)propan-2-yl)phosphoramidate | 628.2 [M + 1]+ |
| Ex. 7 (Compound 6) | 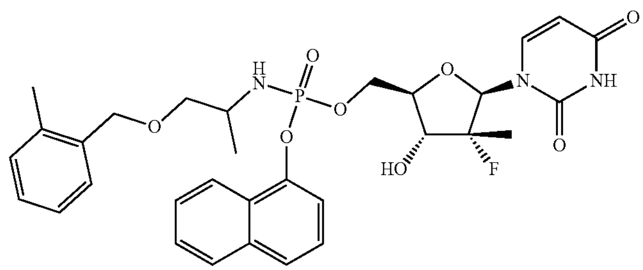 [SMILES: Cc1ccccc1COCC(C)NP(=O)(OC[C@H]1O[C@@H](n2ccc(=O)[nH]c2=O)[C@](C)(F)[C@@H]1O)Oc1cccc2ccccc12] | ((2R,3R,4R,5R)-5-(2,4-dioxo-3,4-dihydropyrimidin-1(2H)-yl)-4-fluoro-3-hydroxy-4-methyltetrahydrofuran-2-yl)methyl-naphth-1-yl-(1-(2-methylbenzyloxy)propan-2-yl)phosphoramidate | 628.2 [M + 1]+ |
| Ex. 8 (Compound 7) | 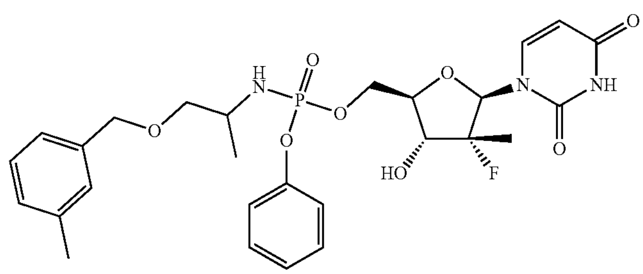 [SMILES: Cc1cccc(COCC(C)NP(=O)(OC[C@H]2O[C@@H](n3ccc(=O)[nH]c3=O)[C@](C)(F)[C@@H]2O)Oc2ccccc2)c1] | ((2R,3R,4R,5R)-5-(2,4-dioxo-3,4-dihydropyrimidin-1(2H)-yl)-4-fluoro-3-hydroxy-4-methyltetrahydrofuran-2-yl)methyl-phenyl-(1-(3-methylbenzyloxy)propan-2-yl)phosphoramidate | 578.2 [M + 1]+ |
| Ex. 9 (Compound 8) | 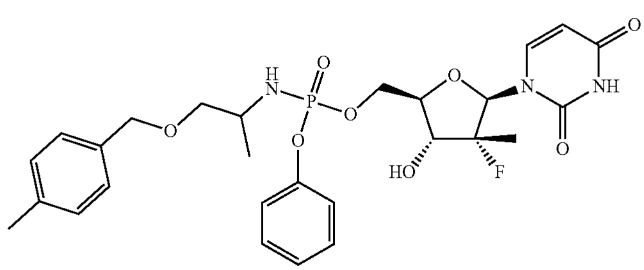 [SMILES: Cc1ccc(COCC(C)NP(=O)(OC[C@H]2O[C@@H](n3ccc(=O)[nH]c3=O)[C@](C)(F)[C@@H]2O)Oc2ccccc2)cc1] | ((2R,3R,4R,5R)-5-(2,4-dioxo-3,4-dihydropyrimidin-1(2H)-yl)-4-fluoro-3-hydroxy-4-methyltetrahydrofuran-2-yl)methyl-phenyl-(1-(4-methylbenzyloxy)propan-2-yl)phosphoramidate | 578.2 [M + 1]+ |
| Ex. 10 (Compound 9) | 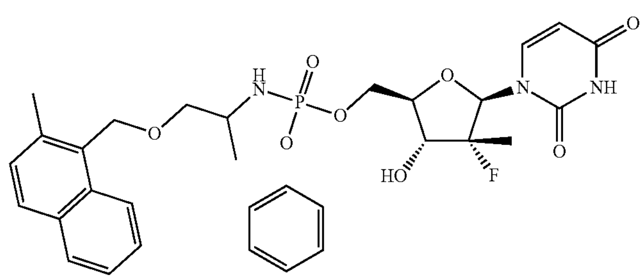 | ((2R,3R,4R,5R)-5-(2,4-dioxo-3,4-dihydropyrimidin-1(2H)-yl)-4-fluoro-3-hydroxy-4-methyltetrahydrofuran-2-yl)methyl-phenyl-(1-(2-methylnaphth-1-ylmethoxy)propan-2-yl)phosphoramidate | 628.2 [M + 1]+ |

Example 11

Preparation of (2S)-(((((1R)-2-(6-amino-9H-purin-9-yl)-1-methylethoxy)methyl-phenoxy-phosphoryl)amino)-3-(2-methylbenzyloxy)-propane (Compound 10)

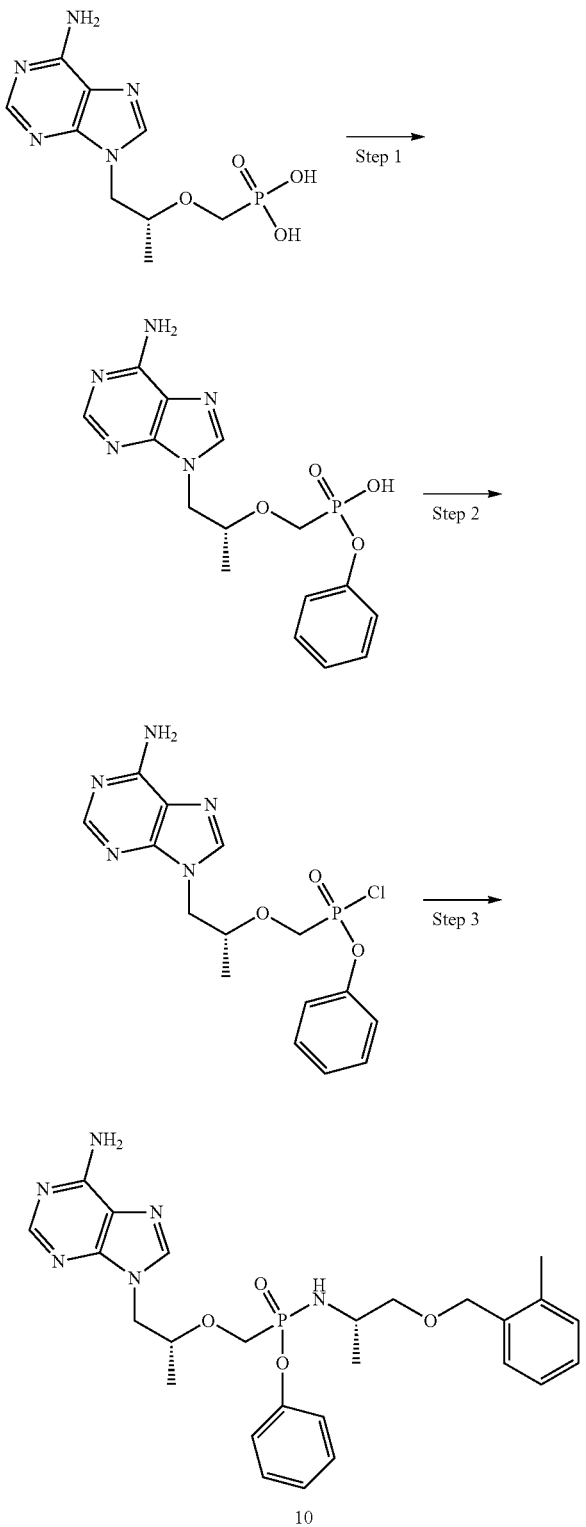

Step 1: Preparation of (((1R)-2-(6-amino-9H-purin-9-yl)-1-methyl-ethoxy)methyl)phosphoric acid monophenyl ester

[(1R)-2-(6-amino-9H-purin-9-yl)-1-methyl-ethoxy]methylphosphoric acid (PMPA, 3.1 g, 10.8 mmol) and phenol (1.0 g, 10.8 mmol) were dissolved in N-methylpyrrolidone (20 mL) at room temperature, and the temperature was raised to 85° C. Triethylamine (1.1 g, 10.8 mmol) was added dropwise such that the white turbid reaction mixture become clear. After completion of the dropwise addition, the temperature was further raised to 100° C., and a solution of DCC (4.8 g, 23.1 mmol) in N-methylpyrrolidone (10 mL) was added dropwise. After the completion of the dropwise addition, the reaction was kept at 100° C. overnight. The temperature of the reaction mixture was lowered to room temperature, and the mixture was allowed to stand for 2 h. After filtration, the filtrate was concentrated and dissolved in dichloromethane. A small amount of white insoluble material was observed. After further filtration, the filtrate was concentrated, and the residue was purified by preparative liquid chromatography to afford the title compound (1.0 g).

ESI-MS (m/z): 364.2 $[M+H]^+$.

Step 2: Preparation of ((((R)-1-(6-amino-9H-purin-9-yl)-1-methyl-ethoxy)methyl) phenoxyphosphoryl chloride (((1R)-2-(6-amino-9H-purin-9-yl)-1-methyl-ethoxy)methyl)phosphoric acid monophenyl ester (100 mg, 0.28 mmol) was dissolved in acetonitrile (0.5 mL) at room temperature, and thionyl chloride (1.0 mL) was added. After the completion of the dropwise addition, the temperature of the reaction mixture was raised to 70° C. After reaction for 3 h, the reaction mixture was concentrated to afford the title compound (110 mg), which was directly used in the subsequent reaction without purification.

ESI-MS (m/z): 378.1 $[M+H]^+$.

Step 3: Preparation of (2S)-(((((1R)-2-(6-amino-9H-purin-9-yl)-1-methyl-ethoxy)methyl-phenoxy-phosphoryl)amino-3-(2-methylbenzyloxy)-propane ((((R)-1-(6-amino-9H-purin-9-yl)-1-methyl-ethoxy)methyl)phenoxyphosphoryl chloride (110 mg, 0.28 mmol) was dissolved in dry dichloromethane (2 mL) at room temperature. The temperature of the reaction mixture was lowered to −20° C. (S)-1-((2-methylphenyl)oxy)-2-aminopropane (99 mg, 0.55 mmol) was added, and triethylamine (0.5 mL) was added dropwise. After the completion of the dropwise addition, the reaction was carried out at −20° C. for 1 hour, and the reaction mixture was poured into water to quench the reaction. The mixture was extracted with dichloromethane, and the organic phases were combined, washed with water, dried, and concentrated to afford a crude compound, which was purified by preparative high performance liquid chromatography to afford the title compound (39 mg).

The structure was characterized as follows:

$^1$H NMR (400 MHz, DMSO-$d_6$) δ 8.20-8.04 (m, 2H), 7.38-7.00 (m, 11H), 5.08-4.81 (m, 1H), 4.44-4.31 (m, 2H), 4.24 (dt, J=14.4, 4.0 Hz, 1H), 4.13 (dt, J=14.1, 6.8 Hz, 1H), 3.97-3.77 (m, 2H), 3.70 (ddd, J=13.3, 9.3, 6.8 Hz, 1H), 3.43-3.37 (m, 1H), 3.29-3.08 (m, 2H), 2.23 (d, J=5.8 Hz, 3H), 1.03 (dd, J=22.8, 6.2 Hz, 3H), 0.95 (t, J=6.8 Hz, 3H).

ESI-MS (m/z): 525.2 $[M+H]^+$.

Example 12

Preparation of (2R)-((((1R)-2-(6-amino-9H-purin-9-yl)-1-methyl-ethoxy)methyl-phenoxy-phosphoryl)amino)-3-(2-methylbenzyloxy)-propane (Compound 11)

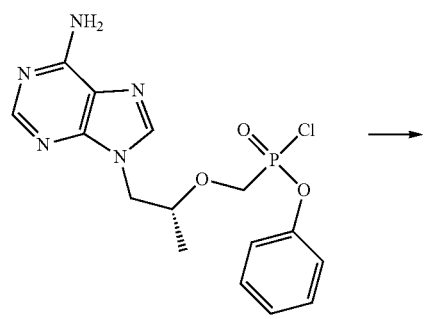

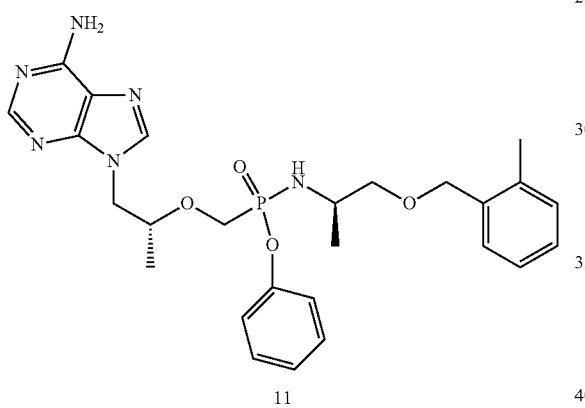

11

((((R)-1-(6-amino-9H-purin-9-yl)-1-methyl-ethoxy)methyl)phenoxyphosphoryl chloride (110 mg, 0.28 mmol) was dissolved in dry dichloromethane (2 mL) at room temperature. The temperature of the reaction mixture was lowered to −20° C., and (R)-1-((2-methylbenzyloxy)-2-amino-propane (99 mg, 0.55 mmol) was added. Triethylamine (0.5 mL) was added dropwise, and after completion of the dropwise addition, the reaction was carried out at −20° C. for 1 h. Then the reaction mixture was poured into water to quench the reaction. The mixture was extracted with dichloromethane, and the organic phases were combined, washed with water, dried, and concentrated to afford a crude compound, which was purified by preparative liquid chromatography to afford the title compound (56 mg).

The structure was characterized as follows:

$^1$H NMR (400 MHz, DMSO-d$_6$) δ 8.11 (dd, J=16.3, 1.3 Hz, 2H), 7.35-7.22 (m, 3H), 7.22-7.09 (m, 7H), 7.09-6.99 (m, 1H), 4.99 (td, J=11.9, 11.3, 6.3 Hz, 1H), 4.38 (d, J=13.0 Hz, 2H), 4.31-4.09 (m, 2H), 3.93-3.89 (m, 1H), 3.85-3.69 (m, 2H), 3.42-3.39 (m, 1H), 3.23 (dd, J=9.2, 5.5 Hz, 1H), 3.11 (ddd, J=30.2, 9.2, 6.8 Hz, 1H), 2.23 (d, J=2.4 Hz, 3H), 1.03 (t, J=6.8 Hz, 3H), 0.95 (dd, J=10.4, 6.6 Hz, 3H).

ESI-MS (m/z): 525.2[M+H]$^+$.

Example 13

Preparation of 1-((((1R)-2-(6-amino-9H-purin-9-yl)-1-methyl-ethoxy)methyl-phenoxy-phosphoryl)amino)-2-(2-methylbenzyloxy)-ethane (Compound 12)

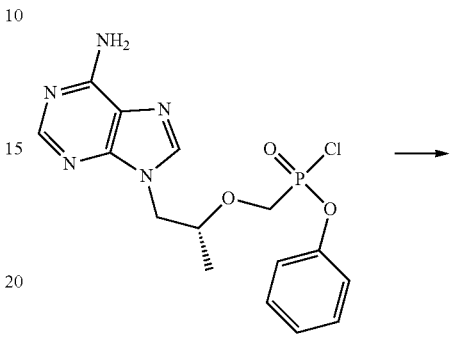

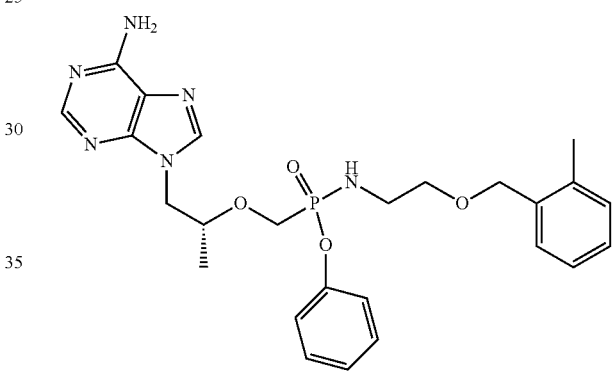

12

((((R)-1-(6-amino-9H-purin-9-yl)-1-methyl-ethoxy)methyl)phenoxyphosphoryl chloride (110 mg, 0.28 mmol) was dissolved in dry dichloromethane (2 mL) at room temperature. The temperature of the reaction mixture was lowered to −20° C., and 1-(2-methylbenzyloxy)-2-ethylamine (100 mg, 0.56 mmol) was added. Triethylamine (0.5 mL) was added dropwise, and after completion of the dropwise addition, the reaction was carried out at −20° C. for 1 hour. Then the reaction mixture was poured into water to quench the reaction. The mixture was extracted with dichloromethane, and the organic phases were combined, washed with water, dried and concentrated to afford a crude compound, which was purified by preparative liquid chromatography to afford the title compound (34 mg).

The structure was characterized as follows:

$^1$H NMR (400 MHz, DMSO-d$_6$) 8.14 (s, 1H), 8.10 (d, J=5.0 Hz, 1H), 7.37-7.24 (m, 3H), 7.20 (s, 2H), 7.18-7.09 (m, 5H), 7.05 (d, J=8.0 Hz, 1H), 5.22-5.06 (m, 1H), 4.45-4.33 (m, 2H), 4.25 (dd, J=14.4, 3.8 Hz, 1H), 4.15 (ddd, J=14.5, 8.5, 6.4 Hz, 1H), 3.97-3.69 (m, 3H), 3.32-3.23 (m, 2H), 3.01 (dd, J=11.2, 6.1 Hz, 2H), 2.23 (d, J=3.1 Hz, 3H), 1.04 (dd, J=13.7, 6.2 Hz, 3H).

ESI-MS (m/z): 511.2 [M+H]$^+$.

Example 14

Preparation of 2-Methyl-2-((((1R)-2-(6-amino-9H-purin-9-yl)-1-methyl-ethoxy)methyl-phenoxy-phosphoryl)amino)-3-(2-methylbenzyloxy)-propane (Compound 13)

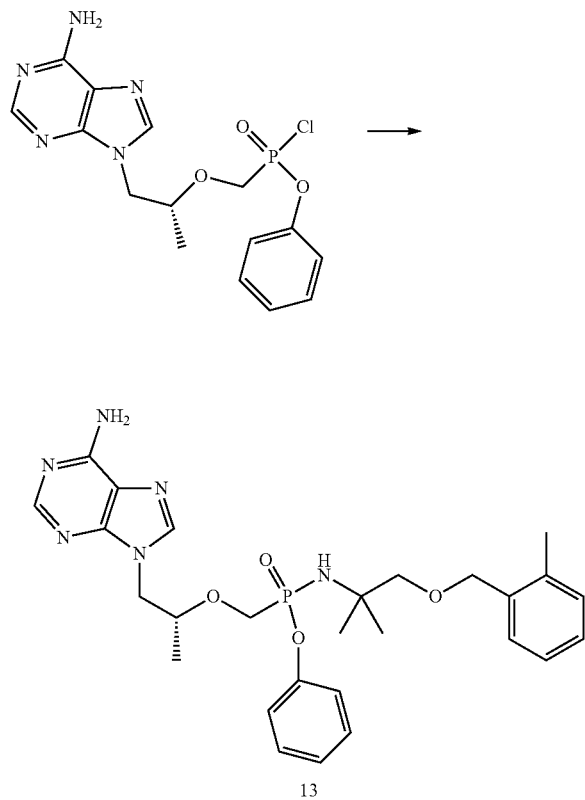

13

((((R)-1-(6-amino-9H-purin-9-yl)-1-methyl-ethoxy)methyl)phenoxyphosphoryl chloride (110 mg, 0.28 mmol) was dissolved in dry dichloromethane (2 mL) at room temperature. The temperature of the reaction mixture was lowered to −20° C., and 1-(2-methylbenzyloxy)-2,2-dimethylethylamine (108 mg, 0.56 mmol) was added. Triethylamine (0.5 mL) was added dropwise, and after completion of the dropwise addition, the reaction was carried out at −20° C. for 1 hour. Then the reaction mixture was poured into water to quench the reaction. The mixture was extracted with dichloromethane, and the organic phases were combined, washed with water, dried and concentrated to afford a crude compound, which was purified by preparative liquid chromatography to afford the title compound (18 mg).

The structure was characterized as follows:

$^1$H NMR (400 MHz, DMSO-$d_6$) δ 8.19-8.01 (m, 2H), 7.37-7.24 (m, 3H), 7.24-7.02 (m, 8H), 4.74 (dd, J=16.2, 9.7 Hz, 1H), 4.42 (d, J=8.3 Hz, 2H), 4.23 (dd, J=14.4, 4.0 Hz, 1H), 4.14 (dd, J=14.4, 6.2 Hz, 1H), 3.95-3.89 (m, 1H), 3.85-3.63 (m, 2H), 3.31-3.19 (m, 2H), 2.24 (d, J=3.4 Hz, 3H), 1.16 (d, J=10.2 Hz, 6H), 1.03 (t, J=6.0 Hz, 3H).

ESI-MS (m/z): 539.3 [M+H]$^+$.

Example 15

Preparation of ((((R)-1-(6-amino-9H-purin-9-yl)propan-2-yl)oxy)methyl)-phenoxy-N-(2-(benzyloxy)ethyl)phosphoramide (Compound 22)

The preparation was conducted according to the synthesis method of Example 12, except that (R)-1-((2-methylbenzyloxy)-2-amino-propane was replaced by 2-(benzyloxy)ethylamine, and by purification using preparative high performance liquid chromatograph, the title compound (1.4 g) was obtained as a white solid.

The structure was characterized as follows:

$^1$H NMR (400 MHz, DMSO-$d_6$) δ 8.15-8.12 (m, 2H), 7.34-7.26 (m, 8H), 7.14-7.03 (m, 3H), 5.22-5.12 (m, 1H), 4.39-4.24 (m, 3H), 3.95-3.68 (m, 3H), 3.36-3.28 (m, 1H), 3.05-2.95 (m, 1H), 1.29-1.16 (m, 2H), 1.05-0.95 (m, 3H).

ESI-MS (m/z): 497.2 [M+H]$^+$.

Example 16

Preparation of Compound 22—Isomer A and Compound 22—Isomer B

Method I for preparing Compound 22—Isomer A and Compound 22—Isomer B:

The compound of Example 15 (400 mg) was separated by chiral chromatography, and the separation conditions were as follows: separation column CHIRALPAKOD-H 0.46 cm I.D.×15 cm L, mobile phase: hexane/IPA/TEA=70/30/0.1 (V/V/V), flow rate 1.0 ml/min, wavelength UV 254 nm, temperature 35° C. The two title stereoisomeric compounds were isolated.

Compound 22—Isomer A: $R_t$=5.846 min, 198 mg, ee %=98.5%, and the structure was characterized as follows:

$^1$H NMR (400 MHz, DMSO-$d_6$) δ 8.14 (s, 1H), 8.10 (s, 1H), 7.37-7.18 (m, 9H), 7.17-7.10 (m, 1H), 7.05 (dt, J=8.5, 1.2 Hz, 2H), 5.16 (dt, J=11.9, 6.9 Hz, 1H), 4.40 (s, 2H), 4.26 (dd, J=14.4, 3.7 Hz, 1H), 4.14 (dd, J=14.4, 6.6 Hz, 1H), 4.02-3.81 (m, 2H), 3.75 (dd, J=13.5, 9.2 Hz, 1H), 3.28 (d, J=5.7 Hz, 2H), 3.05-2.93 (m, 2H), 1.06 (d, J=6.2 Hz, 3H).

ESI-MS (m/z): 497.2 [M+H]$^+$.

Compound 22—Isomer B: $R_t$=7.345 min, 166 mg, ee %=98.3%, and the structure was characterized as follows:

$^1$H NMR (400 MHz, DMSO-$d_6$) δ 8.14 (s, 1H), 8.10 (s, 1H), 7.35-7.21 (m, 9H), 7.13 (t, J=7.3 Hz, 1H), 7.05 (dt, J=8.5, 1.2 Hz, 2H), 5.16 (dt, J=11.8, 6.9 Hz, 1H), 4.40 (s, 2H), 4.26 (dd, J=14.4, 3.7 Hz, 1H), 4.14 (dd, J=14.4, 6.6 Hz, 1H), 3.97-3.81 (m, 2H), 3.75 (dd, J=13.5, 9.2 Hz, 1H), 3.30 (d, J=11.1 Hz, 2H), 3.00 (dq, J=12.5, 6.2 Hz, 2H), 1.06 (d, J=6.2 Hz, 3H).

ESI-MS (m/z): 497.2 [M+H]$^+$.

Method II for preparing Compound 22—Isomer A, wherein ∼ represents either a solid wedge (◼︎) or dashed wedge (┅) chemical bond:

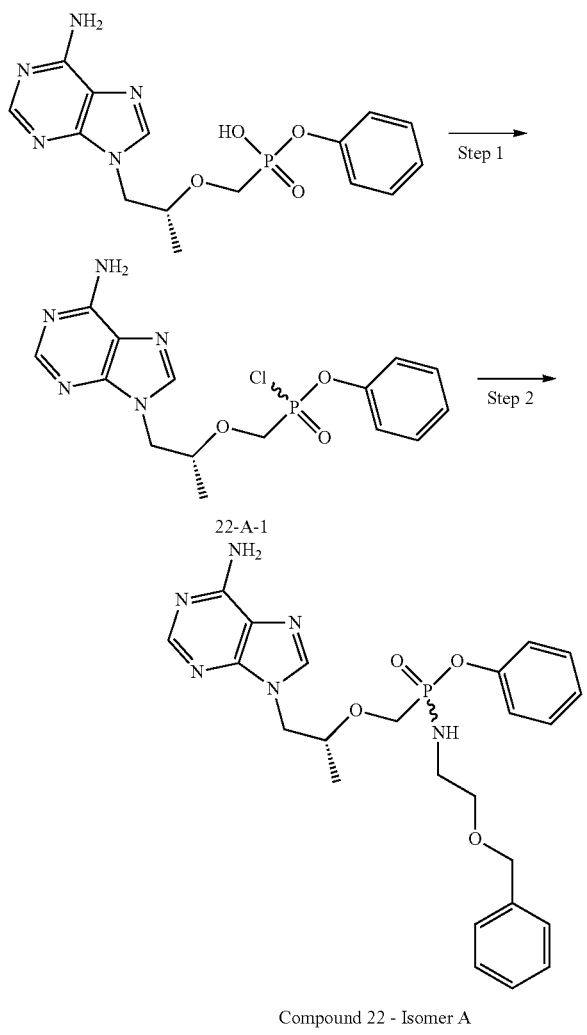

Compound 22 - Isomer A

Step 1: Synthesis of Intermediate 22-A-1

((((1R)-2-(6-amino-9H-purin-9-yl)-1-methylethoxy)methyl)phosphoric acid monophenyl ester (25 g, 68.81 mmol) was dissolved in toluene (250 mL) at room temperature, and thionyl chloride (28.65 g, 240.84 mmol) was added. After completion of the addition, the temperature of the reaction mixture was raised to 95° C., and the reaction was carried out for 48 h. The reaction mixture was evaporated under reduced pressure to afford the title compound (30 g), which was used in the subsequent reaction without further purification.

Step 2: Synthesis of Compound 22—Isomer A 2-(benzyloxy)ethylamine (46.82 g, 309.65 mmol) was dissolved in dry dichloromethane (200 mL) at room temperature, and the temperature was lowered to −35° C. under nitrogen protection. A solution of 22-A-1 (30 g, crude) in toluene (200 mL) was added, and the temperature was controlled to be lower than −10° C. After completion of the addition, the temperature was kept at −10° C., and the reaction was carried out for 1 hour. A 15% potassium hydrogen phosphate aqueous solution (400 mL) was added, and the mixture was stirred well, allowed to stand, and layered. The organic phase was washed successively with 15% potassium hydrogen phosphate (200 mL×2), deionized water (200 mL×2), and dried. The insoluble material was filtered out, and the filtrate was concentrated to afford the title compound (30 g). The retention time ($R_t$) of the resulting product from chiral HPLC detection was consistent with that of Compound 22—Isomer A obtained in Method I of this Example, and the diastereomer purity was 94.6%.

Example 17

Preparation of ((((R)-1-(6-amino-9H-purin-9-yl)propan-2-yl)oxy)methyl)-phenoxy-N-(2-(4-methylbenzyloxy)ethyl)-phosphoramide (Compound 23)

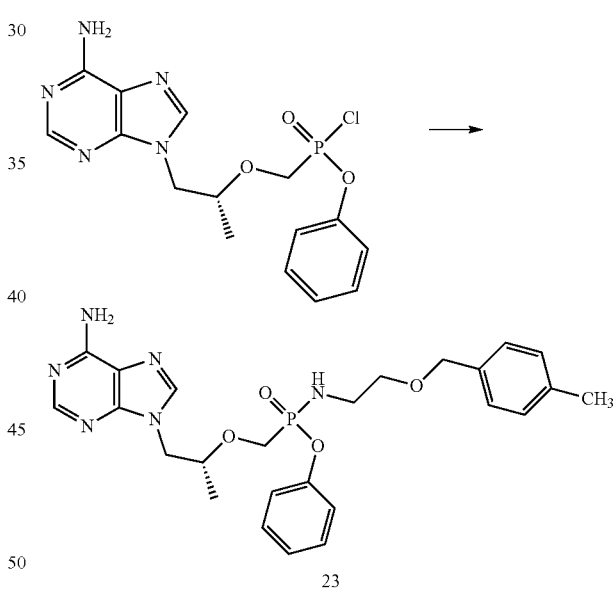

23

The preparation was conducted according to the synthesis method of Example 12, except that (R)-1-((2-methylbenzyloxy)-2-amino-propane was replaced by 2-(4-methylbenzyloxy)ethylamine, and by purification using preparative high performance liquid chromatography, the title compound (65 mg) was obtained.

The structure was characterized as follows:

$^1$H NMR (400 MHz, DMSO-$d_6$) δ 8.14 (s, 1H), 8.10 (d, J=5.0 Hz, 1H), 7.37-7.24 (m, 2H), 7.20-7.11 (m, 8H), 7.03 (d, J=8.0 Hz, 1H), 5.17-5.08 (m, 1H), 4.45-4.33 (m, 2H), 4.34 (s, 1H), 4.32 (s, 1H), 4.27-4.22 (m, 1H), 4.18-4.11 (m, 1H), 3.93-3.71 (m, 3H), 3.33-3.24 (m, 2H), 3.02-2.91 (m, 2H), 2.24 (d, J=3.1 Hz, 3H), 1.04 (dd, J=13.7, 6.2 Hz, 3H).

ESI-MS (m/z): 511.2 [M+H]$^+$.

Example 18

Preparation of ((((R)-1-(6-amino-9H-purin-9-yl)propan-2-yl)oxy)methyl)-phenoxy-N-(2-(2,4-dimethylbenzyloxy)ethyl)-phosphoramide (Compound 26)

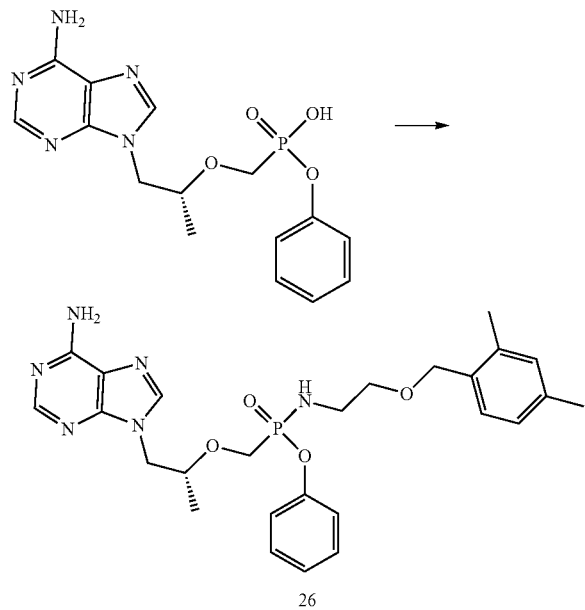

26

The preparation was conducted according to the synthesis method of Example 12, except that (R)-1-((2-methylbenzyloxy)-2-amino-propane was replaced by 2-(2,4-dimethylbenzyloxy)ethylamine, and by purification using preparative liquid chromatograph, the title compound (58 mg) was obtained.

The structure was characterized as follows:

$^1$H NMR (400 MHz, DMSO-$d_6$) δ 8.14 (s, 1H), 8.09 (d, J=8.0 Hz, 1H), 7.34-7.28 (m, 2H), 7.22 (s, 2H), 7.15-7.03 (m, 4H), 6.95-6.93 (m, 2H), 5.26-5.13 (m, 1H), 4.31-4.11 (m, 5H), 3.88-3.75 (m, 3H), 2.92-2.76 (m, 2H), 2.22 (s, 3H), 2.19 (s, 3H), 1.56-1.53 (m, 2H), 1.04 (dd, J=13.7, 6.2 Hz, 3H).

ESI-MS (m/z): 525.2 [M+H]$^+$.

Example 19

Preparation of ((((R)-1-(6-amino-9H-purin-9-yl)propan-2-yl)oxy)methyl)-phenoxy-N-methyl-N-(2-(2-methylbenzyloxy)ethyl)-phosphoramide (Compound 30)

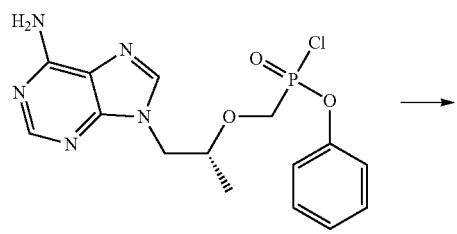

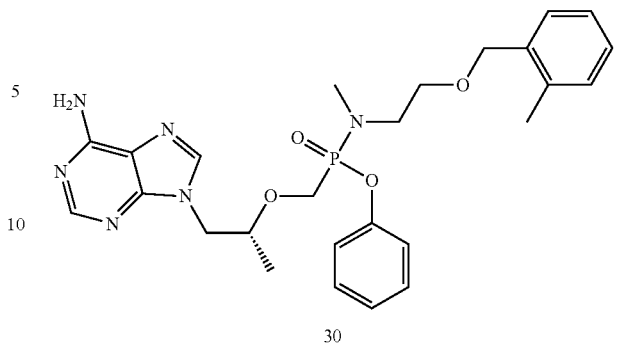

30

The preparation was conducted according to the synthesis method of Example 12, except that (R)-1-((2-methylbenzyloxy)-2-amino-propane was replaced by N-methyl-2-(2-methylbenzyloxy)ethylamine and by purification using preparative high performance liquid chromatograph, the title compound (7 mg) was obtained.

The structure was characterized as follows:

$^1$H NMR (400 MHz, DMSO-$d_6$) δ 8.14 (s, 1H), 8.06 (s, 1H), 7.32-7.10 (m, 10H), 7.04-7.02 (m, 1H), 4.38-4.36 (m, 2H), 4.25-4.15 (m, 2H), 3.95-3.68 (m, 3H), 3.39-3.34 (m, 2H), 3.15-3.00 (m, 2H), 2.54-2.48 (m, 3H), 2.22 (s, 3H), 1.08-1.01 (m, 3H).

ESI-MS (m/z): 525.2 [M+H]$^+$.

Example 20

Preparation of Example 20—Isomer A and Example 20—Isomer B

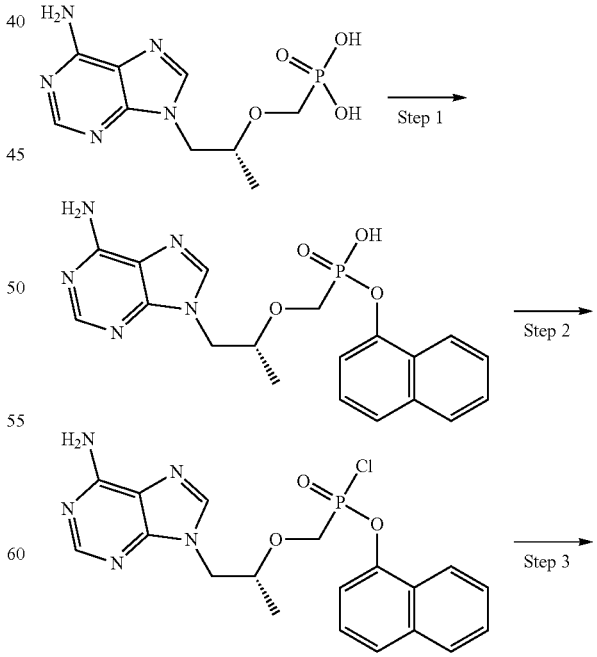

Example 20 - Isomer A + Example 20 - Isomer B

Step 1: Synthesis of ((R)-1-(6-amino-9H-purin-9-yl)
propan-2-yl)oxy)methyl)phosphoric acid mono-1-
naphthyl ester The preparation was conducted according to the synthesis method of Example 11, step 1, except that phenol was replaced by 1-naphthol, and by purification using preparative liquid chromatograph, the title compound (1.2 g) was obtained. ESI-MS (m/z): 414.1 [M+H]$^+$.

Step 2: Synthesis of (((R)-1-(6-amino-9H-purin-9-
yl)propan-2-yl)oxy)methyl)-1-naphthyloxy-phospho-
ryl chloride The preparation was conducted according to the synthesis method of Example 11, step 2, except that (((1R))-2-(6-amino-9H-purin-9-yl)-1-methyl-ethoxy)methyl)phosphoric acid monophenyl ester was replaced by (((R)-1-(6-amino-9H-purin-9-yl)propan-2-yl)oxy)methyl)phosphoric acid mono-1-naphthyl ester, to afford the title compound (200 mg)), which was used directly in the subsequent reaction. ESI-MS (m/z): 432.0 [M+H]$^+$.

Step 3: Synthesis of (R)-((((R)-1-(6-amino-9H-pu-
rin-9-yl)propan-2-yl)oxy)methyl)-naphtha-1-yloxy-
N-(2-(2-methylbenzyloxy)ethyl)-phosphoramide (((R)-1-(6-amino-9H-purin-9-yl)propan-2-yl)oxy) methyl)-1-naphthyloxy-phosphoryl chloride (200 mg, 0.46 mmol) was dissolved in dry dichloromethane (2 mL). The temperature of the reaction mixture was lowered to −20° C. under nitrogen protection. 2-(2-methylbenzyloxy)ethylamine (153 mg, 0.92 mmol) was added, and triethylamine (1.0 mL) was added dropwise. The reaction was carried out at −20° C. for 1 h. The reaction mixture was poured into water (20 mL) to quench, and was extracted with dichloromethane (30 mL×3). The organic phases were combined, washed with water, dried, and concentrated to afford a crude compound, which was purified by preparative high performance liquid chromatography to afford the two title stereoisomeric compounds.

Example 20—Isomer A: R$_f$=2.549 min, 9 mg, and the structure was characterized as follows:

$^1$H NMR (400 MHz, DMSO-d$_6$) δ 8.13-8.10 (m, 3H), 7.95-7.92 (m, 1H), 7.73-7.71 (m, 1H), 7.54-7.52 (m, 2H), 7.43-7.38 (m, 2H), 7.20-7.13 (m, 6H), 5.30-5.27 (m, 1H), 4.31-4.16 (m, 4H), 4.05-3.91 (m, 3H), 3.33-3.25 (m, 2H), 3.05-2.95 (m, 2H), 2.19 (s, 3H), 1.0-0.98 (m, 3H).

ESI-MS (m/z): 561.2 [M+H]$^+$.

Example 20—Isomer B, R, =2.486 min, 35 mg, and the structure was characterized as follows:

$^1$H NMR (400 MHz, DMSO-d$^6$) δ 8.22-8.14 (m, 3H), 8.06-8.04 (m, 1H), 7.73-7.71 (m, 1H), 7.54-7.52 (m, 2H), 7.40-7.36 (m, 2H), 7.19-7.13 (m, 6H), 5.33-5.27 (m, 1H), 4.31-4.18 (m, 4H), 4.05-3.91 (m, 3H), 3.33-3.25 (m, 2H), 3.05-2.95 (m, 2H), 2.19 (s, 3H), 1.00-0.98 (m, 3H).

ESI-MS (m/z): 561.2 [M+H]$^+$.

Example 21

Preparation of ((((R)-1-(6-amino-9H-purin-9-yl)
propan-2-yl)oxy)methyl)-naphtha-2-yloxy-N-(2-(2-
methylbenzyloxy)ethyl)-phosphoramide (Compound
31)

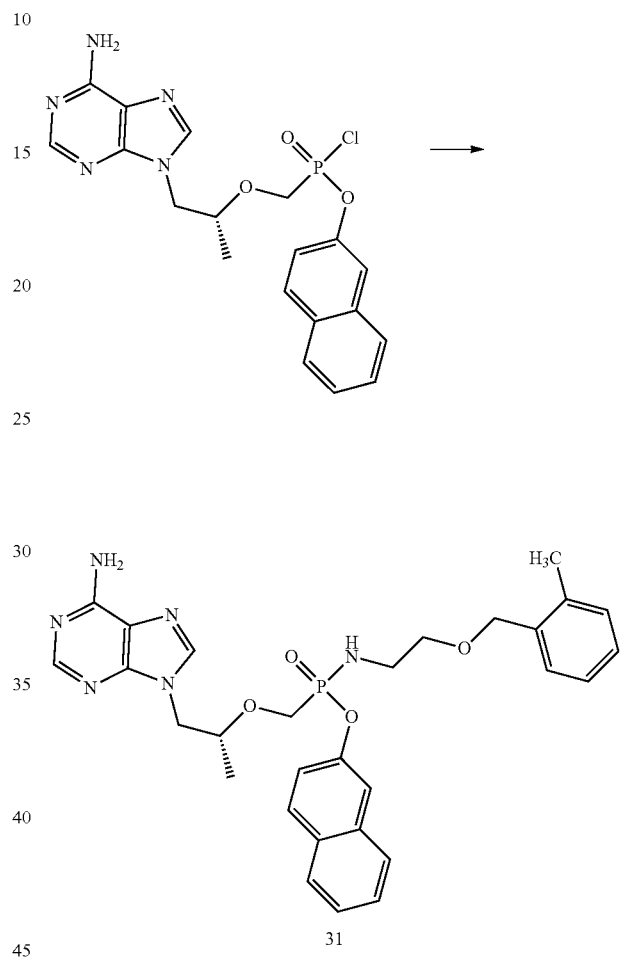

31

The preparation was conducted according to the synthesis method of Example 20, except that 1-naphthol was replaced by 2-naphthol, and by purification using preparative high performance liquid chromatograph, the title compound (58 mg) was obtained.

The structure was characterized as follows:

$^1$H NMR (400 MHz, DMSO-d$_6$) δ 8.17 (s, 1H), 7.92-7.84 (m, 2H), 7.83-7.76 (m, 1H), 7.61 (d, J=15.8 Hz, 1H), 7.49-7.45 (m, 2H), 7.33 (d, J=2.2 Hz, 1H), 7.31-7.22 (m, 3H), 7.18-7.07 (m, 3H), 5.26-5.18 (m, 1H), 4.33 (t, J=3.2 Hz, 1H), 4.29-4.20 (m, 1H), 4.18-3.13 (m, 1H), 3.96-3.77 (m, 3H), 3.33-3.25 (m, 2H), 3.07-2.98 (m, 2H), 2.19 (s, 3H), 1.13-1.02 (m, 3H).

ESI-MS (m/z): 561.2 [M+H]$^+$.

Example 22

Preparation of (((R)-1-(6-amino-9H-purin-9-yl)propan-2-yl)oxy)methyl)-phenoxy-N-((R)-1-(benzyloxy)propan-2-yl)-phosphoramide (Compound 37)

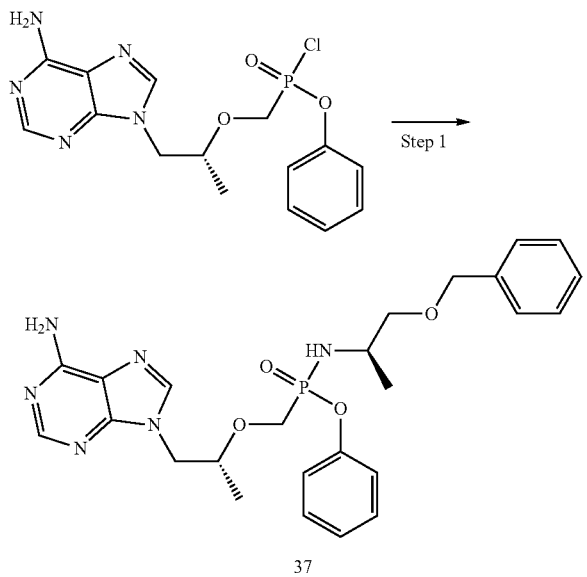

37

The preparation was conducted according to the synthesis method of Example 12, except that (R)-1-((2-methylbenzyloxy)-2-amino-propane was replaced by (R)-1-(benzyloxy)-2-propylamine, and by purification using preparative high performance liquid chromatograph, the title compound (370 mg) was obtained.

The structure was characterized as follows:

¹H NMR (400 MHz, DMSO-d₆) δ 8.14 (s, 1H), 8.10 (s, 1H), 7.33-7.20 (m, 9H), 7.13 (t, J=7.4 Hz, 1H), 7.05 (dt, J=8.3, 1.3 Hz, 2H), 4.99 (dd, J=12.4, 10.2 Hz, 1H), 4.41 (s, 2H), 4.24 (dd, J=14.4, 3.8 Hz, 1H), 4.14 (dd, J=14.4, 6.4 Hz, 1H), 3.91 (td, J=6.3, 3.8 Hz, 1H), 3.86-3.67 (m, 2H), 3.21 (dd, J=9.3, 5.8 Hz, 1H), 3.13 (dd, J=9.3, 6.7 Hz, 1H), 1.04 (d, J=6.2 Hz, 3H), 0.96 (d, J=6.6 Hz, 3H).

ESI-MS (m/z): 511.2 [M+H]⁺.

Example 23

Preparation of Example 23—Isomer a and Example 23—Isomer B

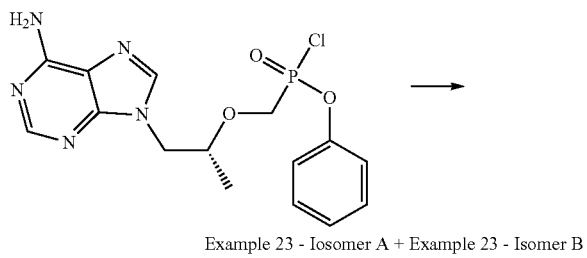

Example 23 - Iosomer A + Example 23 - Isomer B

The preparation was conducted according to the synthesis method of Example 12, except that (R)-1-((2-methylbenzyloxy)-2-amino-propane was replaced by (S)-1-(benzyloxy)-2-propylamine, and by purification using preparative high performance liquid chromatograph, the two title isomers were obtained.

Example 23—Isomer A: R_t=2.486 min, 106 mg, and the structure was characterized as follows:

¹H NMR (400 MHz, DMSO-d6) δ 8.13 (d, J=2.6 Hz, 1H), 8.04 (s, 1H), 7.38-7.16 (m, 10H), 7.14-7.08 (m, 1H), 7.08-7.01 (m, 1H), 4.46 (d, J=12.9 Hz, 2H), 4.30-4.11 (m, 4H), 4.11-4.01 (m, 1H), 4.01-3.89 (m, 2H), 3.57 (ddd, J=19.5, 6.0, 3.3 Hz, 2H), 1.07 (t, J=6.6 Hz, 3H).

ESI-MS (m/z): 511.2 [M+H]⁺.

Example 23—Isomer B: R_t=2.536 min, 75 mg, and the structure was characterized as follows:

¹H NMR (400 MHz, DMSO-d₆) δ 8.14 (s, 1H), 8.12 (s, 1H), 7.36-7.22 (m, 9H), 7.17-7.10 (m, 3H), 4.84 (dd, J=12.4, 10.2 Hz, 1H), 4.36 (d, J=4.3 Hz, 2H), 4.29-4.09 (m, 2H), 3.91-3.77 (m, 2H), 3.70 (dd, J=13.3, 9.4 Hz, 1H), 3.19-3.07 (m, 2H), 1.00 (d, J=6.2 Hz, 3H), 0.94 (d, J=6.6 Hz, 3H).

ESI-MS (m/z): 511.2 [M+H]⁺.

Example 24

Preparation of ((((R)-1-(6-amino-9H-purin-9-yl)propan-2-yl)oxy)methyl)-phenoxy-N-((S)-2-(benzyloxy)propyl)-phosphoramide (Compound 40)

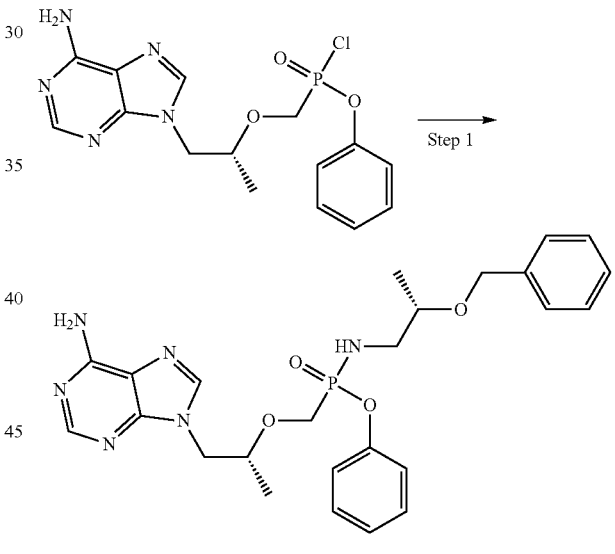

40

The preparation was conducted according to the synthesis method of Example 12, except that (R)-1-((2-methylbenzyloxy)-2-amino-propane was replaced by (S)-2-(benzyloxy)-1-propylamine, and by purification using preparative high performance liquid chromatography, the title compound (205 mg) was obtained.

The structure was characterized as follows:

¹H NMR (400 MHz, DMSO-d6) δ 8.13 (s, 1H), 8.09 (s, 1H), 7.35-7.19 (m, 9H), 7.12 (t, J=7.4 Hz, 1H), 7.05 (dd, J=7.5, 1.3 Hz, 2H), 5.06 (dd, J=11.8, 10.1 Hz, 1H), 4.39 (s, 2H), 4.25 (dd, J=14.4, 3.7 Hz, 1H), 4.13 (dd, J=14.4, 6.6 Hz, 1H), 3.96-3.79 (m, 2H), 3.71 (dd, J=13.5, 9.2 Hz, 1H), 3.26 (dd, J=9.1, 5.2 Hz, 1H), 3.09 (dd, J=9.1, 7.0 Hz, 1H), 1.05 (d, J=6.2 Hz, 3H), 0.96 (d, J=6.6 Hz, 3H).

ESI-MS (m/z): 511.2 [M+H]⁺.

Example 25

Preparation of (((R)-1-(6-amino-9H-purin-9-yl)propan-2-yl)oxy)methyl)-phenoxy-N-((R)-2-(benzyloxy)propyl)-phosphoramide (Compound 41)

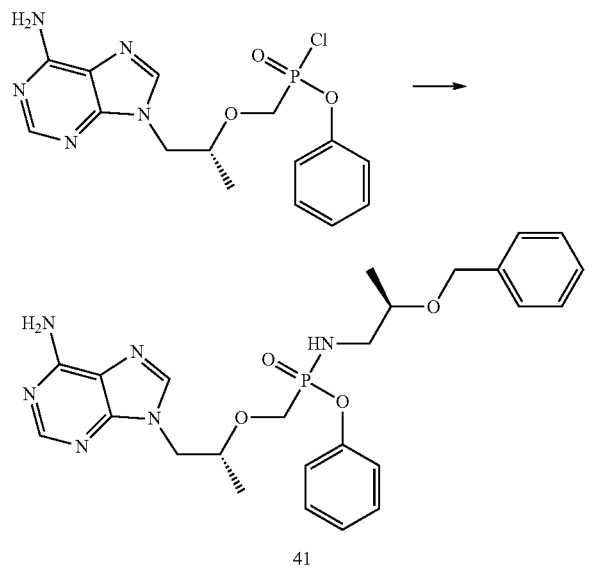

41

The preparation was conducted according to the synthesis method of Example 12, except that (R)-1-((2-methylbenzyloxy)-2-amino-propane was replaced by (R)-2-(benzyloxy)-1-propylamine, and by purification using preparative high performance liquid chromatography, the title compound (260 mg) was obtained.

The structure was characterized as follows:

$^1$H NMR (400 MHz, DMSO-d$_6$) δ 8.14 (s, 1H), 8.10 (s, 1H), 7.36-7.21 (m, 9H), 7.12 (t, J=7.3 Hz, 1H), 7.06 (dt, J=8.4, 1.2 Hz, 2H), 5.08 (dt, J=11.8, 7.1 Hz, 1H), 4.44 (d, J=12.0 Hz, 1H), 4.36 (d, J=11.9 Hz, 1H), 4.25 (dd, J=14.4, 3.7 Hz, 1H), 4.15 (dd, J=14.4, 6.5 Hz, 1H), 3.92-3.72 (m, 3H), 3.33 (d, J=5.9 Hz, 1H), 2.90-2.76 (m, 2H), 1.05 (d, J=6.2 Hz, 3H), 1.02 (d, J=6.2 Hz, 3H).

ESI-MS (m/z): 511.2 [M+H]$^+$.

Example 26

Preparation of ((((R)-1-(6-amino-9H-purin-9-yl)propan-2-yl)oxy)methyl)-phenoxy-N-(1-(benzyloxy)-2-methylpropan-2-yl)-phosphoramide (Compound 42)

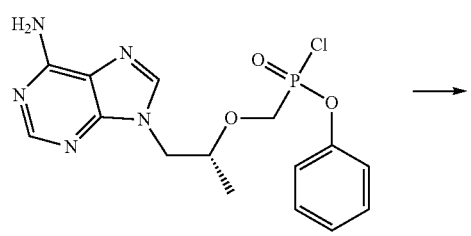

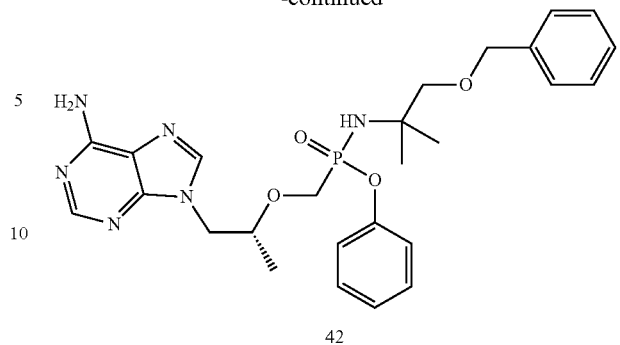

42

The preparation was conducted according to the synthesis method of Example 12, except that (R)-1-((2-methylbenzyloxy)-2-amino-propane was replaced by 1-(benzyloxy)-2-methyl-2-propylamine, and by purification using preparative high performance liquid chromatography, the title compound (30 mg) was obtained.

The structure was characterized as follows:

$^1$H NMR (400 MHz, DMSO-d$_6$) δ 8.13 (s, 1H), 8.10 (s, 1H), 7.31-7.22 (m, 9H), 7.14-7.11 (m, 1H), 7.06-7.04 (m, 2H), 5.11-5.05 (m, 1H), 4.46-4.43 (m, 2H), 4.37-4.34 (m, 1H), 4.28-4.23 (m, 1H), 3.93-3.90 (m, 1H), 3.75-3.65 (m, 2H), 3.39-3.35 (m, 1H), 1.17-1.15 (m, 6H), 1.05-1.02 (m, 3H).

ESI-MS (m/z): 525.2 [M+H]$^+$.

Example 27

Preparation of (((((R)-1-(6-amino-9H-purin-9-yl)propan-2-yl)oxy)methyl)-4-fluorophenoxy-N-(2-(benzyloxy)ethyl)phosphoramide (Compound 43)

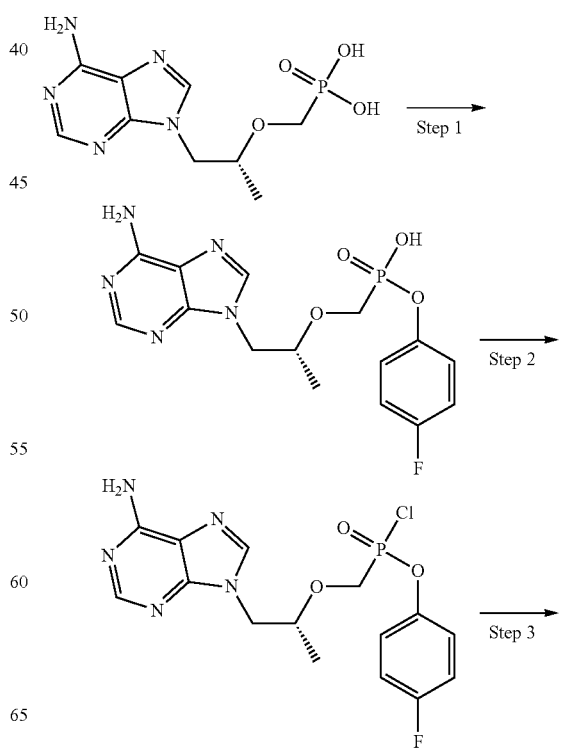

81

-continued

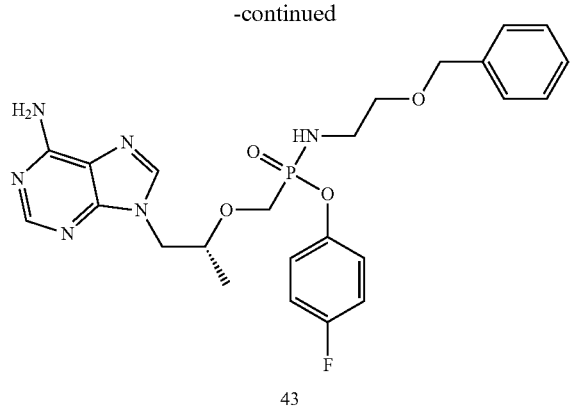

43

Step 1: Synthesis of ((((R)-1-(6-amino-9H-purin-9-yl)propan-2-yl)oxy)methyl)phosphoric acid mono-p-fluorophenyl ester The preparation was conducted according to the synthesis method of Example 11, step 1, except that phenol was replaced by 4-fluorophenol, and by purification using preparative liquid chromatograph, the title compound (400 mg) was obtained. ESI-MS (m/z): 382.1 [M+H]$^+$.

Step 2: Synthesis of 4-fluorophenoxy-((((R)-1-(6-amino-9H-purin-9-yl)propan-2-yl)oxy)methyl)phosphoryl chloride The preparation was conducted according to the synthesis method of Example 11, step 2, except that (((1R)-2-(6-amino-9H-purin-9-yl)-1-methyl-ethoxy)methyl)phosphoric acid monophenyl ester was replaced by 4-fluorophenyl-((((R)-1-(6-amino-9H-purin-9-yl)propan-2-yl)oxy)methyl) phosphate, and the title compound (500 mg) was obtained and was used directly in the subsequent reaction. ESI-MS (m/z): 396.1 [M+H]$^+$.

Step 3: Synthesis of ((((R)-1-(6-amino-9H-purin-9-yl)propan-2-yl)oxy)methyl)-4-fluorophenoxy-N-(2-(benzyloxy)ethyl)-phosphoramide The preparation was conducted according to the synthesis method of Example 11, step 3, except that (S)-1-((2-methylphenyl)oxy)-2-amino-propane was replaced by 2-(benzyloxy)ethylamine, and by purification using preparative high performance liquid chromatograph, the title compound (206 mg) was obtained.

The structure was characterized as follows:

$^1$H NMR (400 MHz, DMSO-d$^6$) δ 8.14 (s, 1H), 8.11 (d, J=4.9 Hz, 1H), 7.39-7.19 (m, 8H), 7.13 (d, J=6.7 Hz, 3H), 5.16 (dt, J=12.9, 6.9 Hz, 1H), 4.38 (d, J=1.5 Hz, 2H), 4.25 (dd, J=14.4, 3.9 Hz, 1H), 4.16 (dd, J=14.4, 6.2 Hz, 1H), 3.99-3.70 (m, 3H), 3.29-3.18 (m, 2H), 2.98 (tq, J=12.6, 6.8 Hz, 2H), 1.03 (d, J=6.2 Hz, 3H).

ESI-MS (m/z): 515.2 [M+H]$^+$.

82

Example 28

Preparation of 2-(benzyloxy)ethyl-phenyl-((((R)-1-(6-amino-9H-purin-9-yl)propan-2-yl)oxy)methyl) phosphate (Compound 44)

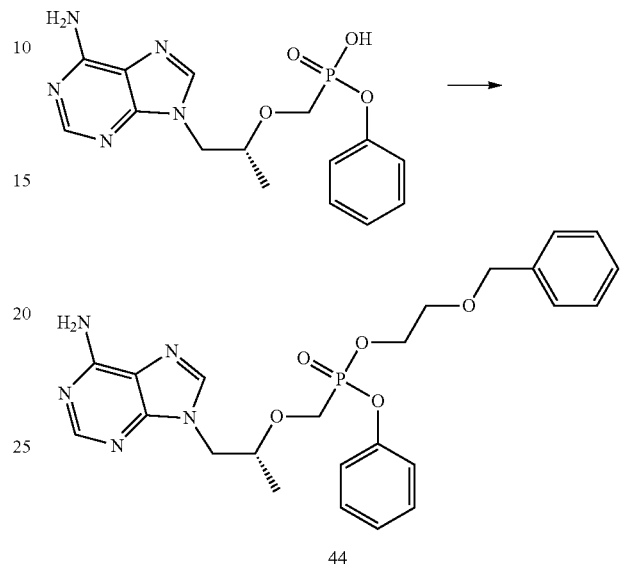

44

((((R)-1-(6-amino-9H-purin-9-yl)propan-2-yl)oxy) methyl)phosphoric acid monophenyl ester (200 mg, 0.55 mmol) and 2-(benzyloxy)ethanol (167 mg, 1.1 mmol) were dissolved in dry N,N-dimethylformamide (2 mL). The temperature of the reaction mixture was lowered to 0° C., and PyBOP (573 mg) was added. N,N-diisopropylethylamine (285 mg) was added dropwise, and after completion of the addition, the temperature was allowed to reach room temperature. The reaction was carried out overnight. By purification using preparative high performance liquid chromatography, the title compound (245 mg) was obtained.

The structure was characterized as follows:

$^1$H NMR (400 MHz, DMSO-d$_6$) δ 8.13 (d, J=2.6 Hz, 1H), 8.04 (s, 1H), 7.38-7.16 (m, 10H), 7.14-7.08 (m, 1H), 7.08-7.01 (m, 1H), 4.46 (d, J=12.9 Hz, 2H), 4.30-4.11 (m, 4H), 4.11-4.01 (m, 1H), 4.01-3.89 (m, 2H), 3.57 (ddd, J=19.5, 6.0, 3.3 Hz, 2H), 1.07 (t, J=6.6 Hz, 3H).

ESI-MS (m/z): 498.2 [M+H]$^+$.

Example 29

Preparation of 3-(benzyloxy)propyl-phenyl-((((R)-1-(6-amino-9H-purin-9-yl)propan-2-yl)oxy)methyl) phosphorate (Compound 45)

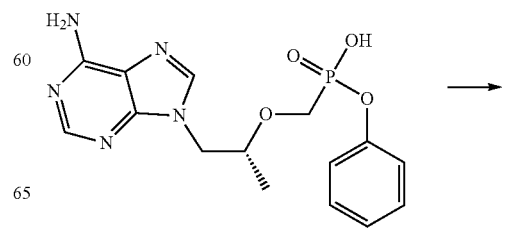

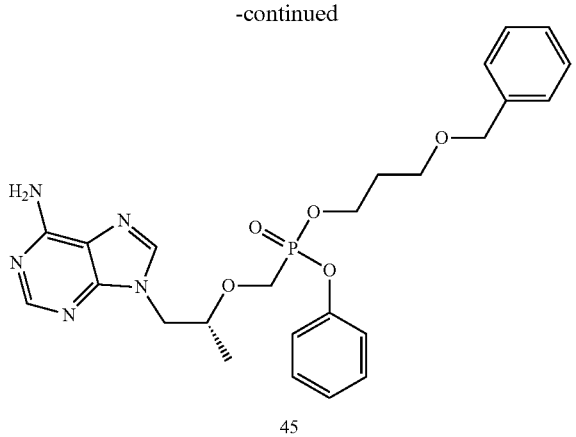

45

The preparation was conducted according to the synthesis method of Example 28, except that 2-(benzyloxy)ethanol was replaced by 3-(benzyloxy)-1-propanol, and by purification using preparative high performance liquid chromatography, the title compound (160 mg) was obtained.
Structural Characterization:
$^1$H NMR (400 MHz, DMSO-$d_6$) δ 8.13 (d, J=1.9 Hz, 1H), 8.03 (d, J=1.9 Hz, 1H), 7.37-7.16 (m, 10H), 7.10 (dt, J=8.5, 1.3 Hz, 1H), 7.04 (dt, J=8.4, 1.3 Hz, 1H), 4.41 (d, J=6.5 Hz, 2H), 4.31-3.89 (m, 8H), 3.42 (dt, J=14.4, 6.2 Hz, 2H), 1.88-1.72 (m, 2H), 1.09 (t, J=6.2 Hz, 3H).
ESI-MS (m/z): 512.2 [M+H]$^+$.

Example 30

Preparation of ((((R)-1-(6-amino-9H-purin-9-yl)propan-2-yl)oxy)methyl)-phenoxy-N-(3-(benzyloxy)propanyl phosphoramide (Compound 46)

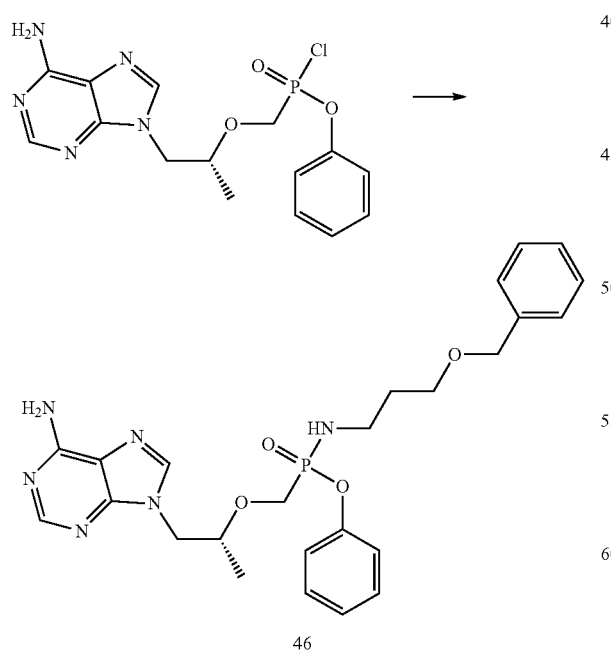

46

The preparation was conducted according to the synthesis method of Example 12, except that (R)-1-((2-methylbenzyloxy)-2-amino-propane was replaced by (S)-2-(benzyloxy)-1-propylamine, and by purification using preparative high performance liquid chromatography, the title compound (173 mg) was obtained.

The structure was characterized as follows:
$^1$H NMR (400 MHz, DMSO-$d_6$) δ 8.14 (s, 1H), 8.10 (d, J=6.1 Hz, 1H), 7.36-7.20 (m, 9H), 7.17-7.09 (m, 2H), 5.06 (td, J=11.4, 5.9 Hz, 1H), 4.37 (d, J=2.2 Hz, 2H), 4.32-4.11 (m, 2H), 4.00-3.70 (m, 3H), 3.36 (dd, J=6.3, 2.3 Hz, 2H), 2.87 (ddd, J=10.4, 6.3, 2.6 Hz, 2H), 1.55 (p, J=6.7 Hz, 2H), 1.07 (dd, J=16.9, 6.2 Hz, 3H).
ESI-MS (m/z): 511.2 [M+H]$^+$.

Example 31

Preparation of (((R)-1-(6-amino-9H-purin-9-yl)propan-2-yl)oxy)methyl)-phenoxy-N-(2-(naphtha-1-ylmethoxy)ethyl)-phosphoramide (Compound 47)

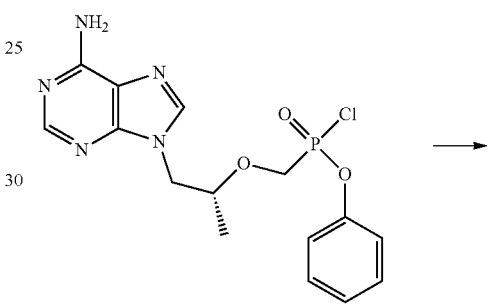

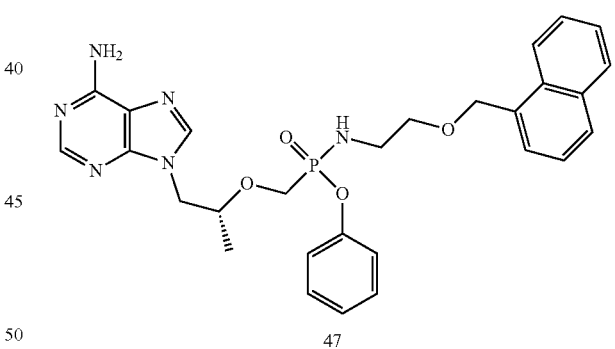

47

The preparation was conducted according to the synthesis method of Example 12, except that (R)-1-((2-methylbenzyloxy)-2-amino-propane was replaced by 2-(1-naphthylmethoxy)ethylamine, and by purification using preparative liquid chromatography, the title compound (33 mg) was obtained.

The structure was characterized as follows:
$^1$H NMR (400 MHz, DMSO-$d_6$) δ 8.19 (s, 1H), 8.18-8.05 (m, 2H), 7.85-7.79 (m, 2H), 7.49-7.39 (m, 4H), 7.27-7.22 (m, 2H), 7.09-7.06 (m, 2H), 6.96 (d, J=8.0 Hz, 1H), 4.87-4.85 (m, 1H), 4.22-4.20 (m, 1H), 4.10-4.02 (m, 1H), 3.82-3.53 (m, 3H), 3.46-3.43 (m, 2H), 3.22-3.03 (m, 2H), 1.03 (dd, J=16.0, 8.0 Hz, 3H).
ESI-MS (m/z): 547.2 [M+H]$^+$.

Example 32

Preparation of ((((R)-1-(6-amino-9H-purin-9-yl)propan-2-yl)oxy)methyl)-phenoxy-N-(2-(2,6-dimethylbenzyloxy)ethyl)-phosphoramide (Compound 48)

Example 33

Preparation of ((((R)-1-(6-amino-9H-purin-9-yl)propan-2-yl)oxy)methyl)-phenoxy-N-(3-(2,4-dimethylbenzyloxy)propyl)-phosphoramide (Compound 49)

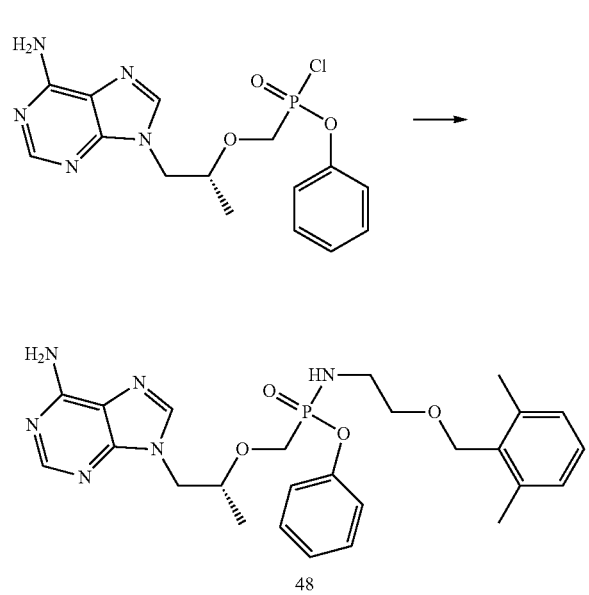

48

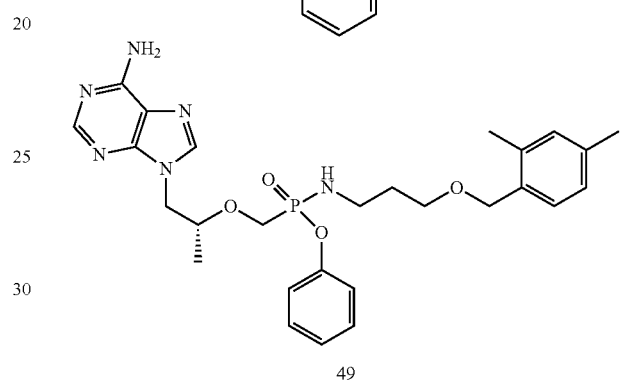

49

The preparation was conducted according to the synthesis method of Example 12, except that (R)-1-((2-methylbenzyloxy)-2-amino-propane was replaced by 2-(2,6-dimethylbenzyloxy)ethylamine, and by purification using preparative high performance liquid chromatography, the title compound (21 mg) was obtained.

The structure was characterized as follows:
$^1$H NMR (400 MHz, DMSO-$d_6$) δ 8.14 (s, 1H), 8.08 (s, 1H), 7.32-6.97 (m, 10H), 5.19-5.13 (m, 1H), 4.40 (s, 2H), 4.28-4.23 (m, 1H), 4.17-4.12 (m, 1H), 3.94-3.83 (m, 2H), 3.78-3.72 (m, 1H), 3.31-2.96 (m, 2H), 3.04-2.96 (m, 2H), 2.28 (s, 6H), 1.06-1.01 (m, 3H).
ESI-MS (m/z): 497.2 [M+H]$^+$.

The preparation was conducted according to the synthesis method of Example 12, except that (R)-1-((2-methylbenzyloxy)-2-amino-propane was replaced by 3-(2,4-dimethylbenzyloxy)-1-propylamine, and by purification using preparative liquid chromatography, the title compound (53 mg) was obtained.

The structure was characterized as follows:
$^1$H NMR (400 MHz, DMSO-$d_6$) δ 8.13 (s, 1H), 8.09 (d, J=8.0 Hz, 1H), 7.32-7.26 (m, 2H), 7.21 (s, 2H), 7.15-7.11 (m, 3H), 7.05-6.91 (m, 3H), 5.26-5.13 (m, 1H), 4.34-4.32 (m, 2H), 4.24-4.15 (m, 2H), 3.87-3.63 (m, 3H), 3.31-3.19 (m, 2H), 3.08-2.95 (m, 2H), 2.22 (s, 3H), 2.19 (s, 3H), 1.06 (dd, J=16.0, 8.0 Hz, 3H).
ESI-MS (m/z): 539.3 [M+H]$^+$.

With reference to the synthesis method of Examples 11-33, the following compounds were obtained:

| Ex. | Structure | Compound | M/Z |
| --- | --- | --- | --- |
| Ex. 34 Compound 50) | ![structure] | ((((R)-1-(6-amino-9H-purin-9-yl)propan-2-yl)oxy)methyl)-phenoxy-N-(2-(3-chlorobenzyloxy)ethyl)-phosphoramide | 531.2 [M + 1]$^+$ |

| Ex. | Structure | Compound | M/Z |
|---|---|---|---|
| Ex. 35 Compound 51) | 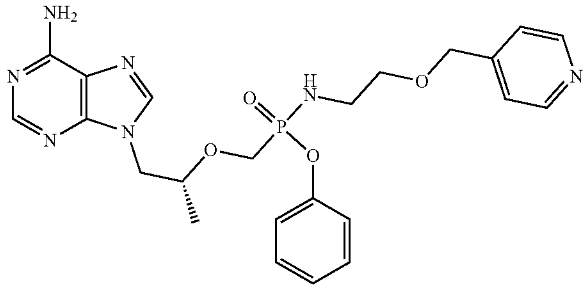 [SMILES: C[C@H](Cn1cnc2c(N)ncnc21)OCP(=O)(NCCOCc1ccncc1)Oc1ccccc1] | ((((R)-1-(6-amino-9H-purin-9-yl)propan-2-yl)oxy)methyl)-phenoxy-N-(2-(pyridin-4-methoxy)ethyl)-phosphoramide | 498.2 [M + 1]+ |
| Ex. 36 Compound 52) | 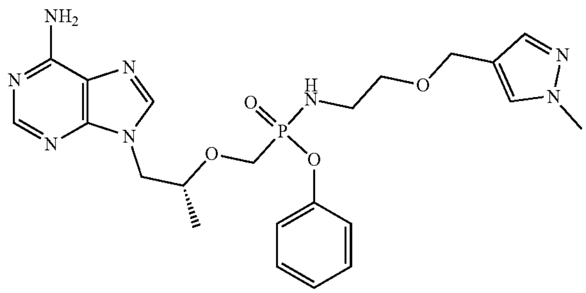 [SMILES: C[C@H](Cn1cnc2c(N)ncnc21)OCP(=O)(NCCOCc1cnn(C)c1)Oc1ccccc1] | ((((R)-1-(6-amino-9H-purin-9-yl)propan-2-yl)oxy)methyl)-phenoxy-N-(2-((1-methyl-1H-pyrazol-4-yl)methoxy)ethyl)-phosphoramide | 501.2 [M + 1]+ |
| Ex. 37 Compound 53) | 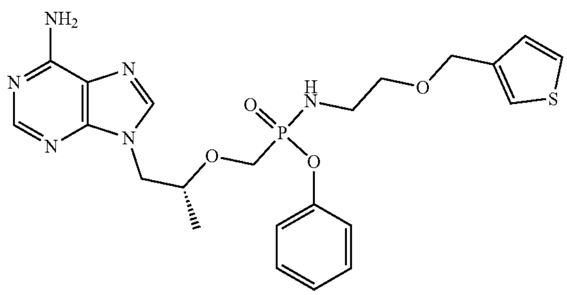 [SMILES: C[C@H](Cn1cnc2c(N)ncnc21)OCP(=O)(NCCOCc1ccsc1)Oc1ccccc1] | ((((R)-1-(6-amino-9H-purin-9-yl)propan-2-yl)oxy)methyl)-phenoxy-N-(2-(thien-3-methoxy)ethyl)-phosphoramide | 503.2 [M + 1]+ |

Biological Activity Tests

1. In Vitro Screen and Evaluation of Nucleosides for Nucleoside Triphosphate Metabolites (3P) Production in Human Primary Hepatocytes 1.1. Test System Human primary hepatocytes (batch No. MMN, 10 donors, mixed-gender) were purchased from Bioreclamation IVT, an in vitro technology company.

1.2. Test Method

A suspension of human primary hepatocytes in a concentration of $6\times10^5$ cells/mL and a solution of the test compound in a concentration of 50 μM were prepared. 250 μL of the suspension of human primary hepatocytes and 250 μL of the solution of the test compound were mixed and added to a 24-well plate so that the final concentration of the test compound was 25 μM, After incubating for 6 h in a water bath at 37° C., the sample was transferred to a test tube and the medium was removed. After washing the cells with a phosphate buffer, the supernatant was removed. 180 μL of 70% methanol was added, and the mixture was vortexed and allowed to stand at −20° C. overnight. After centrifugation at 15000 rpm and 4° C. for 10 min, 150 μL of the supernatant was transferred to a loading tube, and the production amount of 3P products was detected by LC-MS/MS to calculate the 3P production rate.

3P production rate=(3P production amount*150 μL)/($6\times10^5$ cells/mL*250 μL*6 h).

1.3. Test Results

The production amount and production rate of 3P compound for the test compounds are shown in the table below.

TABLE 2

The production amount and production rate of 3P compound for the test compounds

| Ex. | 3P production amount nM | 3P production rate (pmol/$10^6$/min) |
|---|---|---|
| Ex. 1 | 1273 | 3.5 |
| Ex. 2 | 4170 | 11.5 |
| Ex. 3 | 4370 | 12.1 |
| Ex. 14 | 637 | 1.77 |
| Ex. 16 - Compound 22 - Isomer A | 1487 | 4.13 |
| Ex. 16 - Compound 22 - Isomer B | 1157 | 3.21 |
| Ex. 17 | 314 | 0.87 |
| Ex. 20 - Isomer A | 364 | 1.01 |
| Ex. 20 - Isomer B | 625 | 1.73 |
| Ex. 21 | 443 | 1.23 |

It can be seen that the compound of the invention can be well metabolized in hepatocytes to produce the active nucleoside triphosphate metabolite, and nucleoside triphosphate metabolite is produced in a large amount and a high rate. Therefore, the compound of the invention has a good inhibitory effect on hepatitis C, hepatitis B and human immunodeficiency syndrome and the like.

2. CYP Inhibition Test 2.1. Test Method 2.1.1. Preparation of Stock Solution and Working Solution of the Test Compound The compound was dissolved in DMSO to prepare a 10 mM stock solution. The stock solution was further diluted into a series of working solutions of 5, 1.5, 0.5, 0.15, 0.05, 0.015 and 0.005 mM with a mixed solvent of DMSO:methanol=1:1.

2.1.2. Substrate and Preparation Thereof

The substrates were each dissolved in DMSO to prepare stock solutions of the corresponding concentrations. The specific concentrations are shown in the table below:

TABLE 3

Concentrations of substrates in stock solutions and incubation systems of different groups in CYP inhibition tests

| Substrate | Concentration in stock solutions (mM) | Concentration in incubation systems ($\lambda$M) |
|---|---|---|
| Phenacetin (1A2) | 20 | 10 |
| Diclofenac (2C9) | 10 | 5 |
| Methoin (2C19) | 20 | 30 |
| Dextromethorphan (2D6) | 20 | 5 |
| Midazolam (3A4) | 10 | 2 |
| Testosterone (3A4) | 40 | 50 |
| Amodiaquine (2C8) | 10 | 10 |
| Bupropion (286) | 80 | 80 |

2.1.3. Preparation of Solutions of Positive Controls

The positive controls were each dissolved in DMSO to prepare stock solutions of the corresponding concentrations. They were then diluted with methanol to the corresponding concentrations of working solutions. The specific concentrations of stock solutions are shown in the table below:

TABLE 4

Concentrations of positive controls in stock solutions and working solutions of different groups in CYP inhibition tests

| Inhibitors | Concentrations in stock solutions (mM) | Concentrations in working solutions ($\lambda$M) |
|---|---|---|
| Naphthoflavone (1A2) | 3 | 300 |
| Sulfaphenazolum (2C9) | 10 | 300 |
| Phenylcyclopropylamine (2C19) | 10 | 300 |
| Quinidine (2D6) | 3 | 300 |
| Ketoconazole (3A4) | 3 | 300 |
| Quercetin (2C8) | 3 | 300 |
| Ticlopidine (2B6) | 3 | 300 |

2.1.4. Liver Microsome Incubation

The protein concentration of liver microsomes in the reaction system was 0.2 mg/mL, and the coenzyme NADPH was 1.0 mM. The incubation was carried out in a water bath at 37° C. The reaction was quenched and subjected to conventional procedures for LC-MS/MS analysis.

2.2. Test Results

TABLE 5

CYP inhibition test results

| Test Compound | $IC_{50}$ ($\mu$L) | | | | | | | |
|---|---|---|---|---|---|---|---|---|
| | CYP1A2 | CYP2B6 | CYP2C8 | CYP2C9 | CYP2C19 | CYP2D6 | CYP3A4-M | CYP3A4-T |
| Ex. 15 | >50 | >50 | >50 | >50 | >50 | >50 | 11.6 | 13.3 |

It is generally considered that $IC_{50}$>10 $\mu$L indicates that the drug has little or no inhibitory effect on CYP450 enzyme. From the above data, it can be seen that the compound of Example 15 of the present invention has no inhibitory effect on all the eight CYP450 enzymes. The risk of drug interaction is little, and thus higher safety exists. Other compounds of the invention all have similar safety.

3. In Vitro Pharmacological Test

The inhibitory effect of the compounds of the invention on hepatitis B virus (HBV) was tested. The cytotoxicity of the compounds of the invention and the effect thereof on viral (HBV) nucleic acid (DNA) replication levels were tested at cellular level.

3.1. Test Method

HepG2.2.15 cells in logarithmic growth phase were seeded in a 96-well plate at a cell concentration of 40 cells/$\mu$L, and were incubate for 3 days at 37° C. in a 5% $CO_2$ incubator. The medium was replaced with new medium (200 $\mu$L/well) before adding the compound. The concentration of each compound of the examples in the stock solutions was 200 $\mu$M. The highest concentration was 200 $\mu$M, and dilution with DMSO lead to a number of different concentrations. 1 $\mu$L of the test compound was placed in the corresponding medium well, and the final test concentrations of the compounds were 0.06, 0.24, 0.98, 3.9, 15.6, 62.5, 250, 1000 nM (for calculating the medium effective concentration ($EC_{50}$)).

3.2. Test Results

As can be seen from Table 6, the tested compound has strong inhibitory activity against hepatitis B virus (HBV).

TABLE 6

| Compound | EC$_{50}$ (nM) |
|---|---|
| Ex. 15 | 54.7 ± 26.4 |

4. In Vivo Pharmacokinetics (PK) Study in Mice

Nucleoside analogues are phosphorylated by thymidine kinase produced by virus, metabolized into a potent monophosphate, and then metabolized into active forms of diphosphate and triphosphate to achieve the antiviral effect. Therefore, the production of active monophosphate metabolites is fundamental to the efficacy of nucleoside analogues.

The following structure is Metabolite 1 of Compound 22—Isomer B of Example 16:

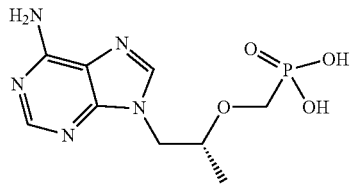

Metabolite 1 of Compound 22 - Isomer B of Example 16

Test method: Compound 22—Isomer B of Example 16 was administered to male ICR mice by intragastric administration. The blood drug level and liver drug level of Compound 22—Isomer B of Example 16 and the metabolite (Metabolite 1 of Compound 22—Isomer B of Example 16) were determined in vivo in the mice to investigate the pharmacokinetic properties of the compounds. The dose for intragastric administration was 10 mg/kg, and the solvent system was 0.5% MC. Blood and liver tissue were collected at different time points after intragastric administration for PK studies. Plasma samples and liver tissue homogenates were subjected to protein precipitation treatment, and analyzed by LC-MS/MS.

LC-MS/MS: Mass spectrometer was API 5500, and the liquid phase was Shimadzu LC-30AD system. The column for the test was Hypersil GOLD C18, 3 μm particle size, 100×4.6 mm, Thermo Company, USA; mobile phase: Phase A was 5 mA ammonium formate+0.5% formic acid, Phase B was methanol; flow rate was 0.8 mL/min; Column temperature was 40° C. The ion source was used in ESI source positive ion mode, and the scanning mode was multiple reaction monitoring (MRM).

TABLE 7

In vivo PK test results in mice

| Administration route/gender/dose | Sampling time (h) | Plasma concentration of Compound 22 - Isomer B of Example 16 (ng/ml) | Liver concentration of Compound 22 - Isomer B of Example 16 (ng/g) | Plasma concentration of Metabolite 1 of Compound 22 - Isomer B of Example 16 (ng/ml) | Liver concentration of Metabolite 1 of Compound 22 - Isomer B of Example 16 (ng/g) |
|---|---|---|---|---|---|
| Oral/Male/10 mg/kg | 0 | 0.00 | 0.00 | 0.00 | 0.00 |
| | 0.5 | 42.1 | 105 | 318 | 6813 |
| | 1 | 22.0 | 48.5 | 95.2 | 5793 |

As seen from the above data, Compound 22—Isomer B of Example 16 of the present invention can be rapidly metabolized in plasma and liver to produce Metabolite 1 of Compound 22—Isomer B of Example 16. The concentration of Metabolite 1 in liver was 21 times the plasma concentration, i.e., Compound 22—Isomer B of Example 16 was obviously liver-targeting.

5. In Vivo Pharmacological Test in Mice

5.1. Test Method

The day on which animals were subjected to hydrodynamic injection of HBV plasmid DNA via tail vein was day 0, and the next day was day 1, and so on. On day 0, all mice were injected with plasmid DNA solution in an amount of 8% by weight of the mice (injection volume (ml)=mouse body weight (g)×8%) from the tail vein (HDI) within 5 seconds, and the mass of the injected plasmid to each mouse was 10 μg.

Test compound: Isomer B of Example 16; Dosage: 10 mg/kg, 30 mg/kg; administration mode: intragastric; administration frequency: once daily; total duration: day 1 to day 7.

5.2. Test Results

The results of determination of HBV DNA contents in plasma and liver of mice are shown in Table 8 and Table 9 below.

TABLE 8

Determination of HBV DNA content in mouse plasma

| Group | Dosage (mg/kg) | Post-HDI Time (day) | Log (HBV DNA content (copies/λl)) |
|---|---|---|---|
| Control | 0 | 1 | 2.43 ± 0.07 |
| | | 3 | 4.69 ± 0.08 |
| | | 5 | 5.35 ± 0.08 |
| | | 7 | 4.84 ± 0.05 |
| Compound 22 - Isomer B of Example 16 | 10 | 1 | 2.44 ± 0.09 |
| | | 3 | 3.21 ± 0.18 |
| | | 5 | 3.00 ± 0.13 |
| | | 7 | 2.26 ± 0.09 |
| Compound 22 - Isomer B of Example 16 | 30 | 1 | 2.33 ± 0.07 |
| | | 3 | 1.96 ± 0.16 |
| | | 5 | 1.53 ± 0.04 |
| | | 7 | 0.94 ± 0.06 |

TABLE 9

Determination of HEW DNA content in mouse plasma (day 7)

| Group | Dosage (mg/kg) | Log(HBV DNA content (copies/λl)) |
|---|---|---|
| Control | 0 | 6.02 ± 0.08 |
| Compound 22 - Isomer B of Example 16 | 10 | 4.45 ± 0.06 |
|  | 30 | 3.58 ± 0.09 |

As can be seen from the above data. Compound 22—Isomer B of Example 16 of the present invention has a significant inhibitory effect on mouse plasma and liver HBV DNA in a dose-dependent manner. It is expected that Compound 22—Isomer B of Example 16 would have a significant therapeutic effect on hepatitis B. Therefore, the compound of the invention can be used as an effective hepatitis B virus reverse transcriptase inhibitor.

INDUSTRIAL APPLICABILITY

The compound of the invention is a hepatitis C virus (HCV) NS5B polymerase inhibitor, a hepatitis B virus DNA polymerase inhibitor, and a retroviral reverse transcriptase inhibitor, and can be efficiently metabolized in vivo, converted to a nucleoside triphosphate metabolite in high amounts. Thus, the compound of the invention has superior virus inhibitory activity.

What is claimed is:

1. A compound represented by Formula (I), a pharmaceutically acceptable salt, ester, solvate, isomer thereof, any crystalline form or racemate of the foregoing, a metabolite form of the foregoing, or a mixture of the foregoing,

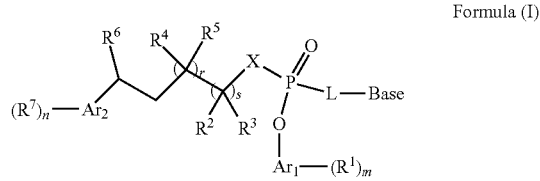

Formula (I)

wherein

L is selected from the group consisting of substituted or unsubstituted $C_{1-12}$ alkylene, $C_{2-12}$ alkenylene, $C_{2-12}$ alkynylene, and the alkylene, alkenylene or alkynylene is optionally interrupted by one or more —O—, —$NR^8$— or —S—; or L represents a group of Formula (c), Formula (d) or Formula (e), wherein ===== represents a single bond or a double bond, position 1 is attached to the Base, and position 2 is attached to the phosphorus atom (P):

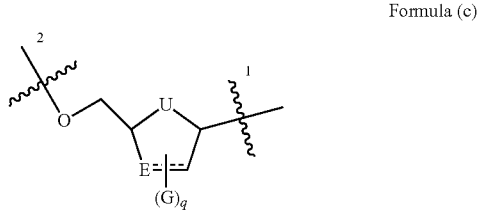

Formula (c)

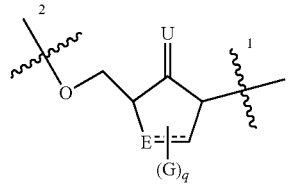

Formula (d)

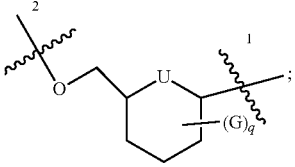

Formula (e)

Base represents a group of Formula (a) or Formula (b):

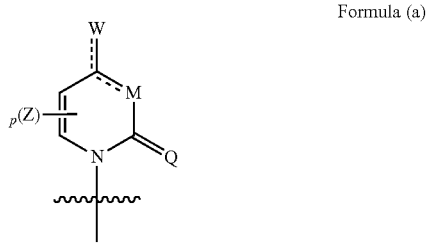

Formula (a)

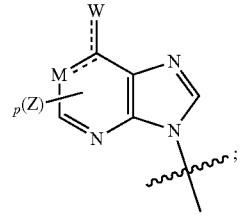

Formula (b)

===== represents a single bond or a double bond;

M represents N or $NR^8$;

W represents H, $NR^8R^9$, $NR^8$, $CH_2$, O or S;

Q represents O, S, $NR^8$ or $CH_2$;

each Z, at each occurrence, independently represents hydrogen, halogen, hydroxy, cyano, nitro, azido, $NR^8R^9$, substituted or unsubstituted $C_{1-6}$ alkyl, substituted or unsubstituted $C_{1-6}$ alkoxy, or substituted or unsubstituted $C_{3-8}$ cycloalkyl, and if there are multiple Z groups, they each may be the same or different;

p represents 0, 1, 2, 3, 4 or 5;

provided that when M is attached by a double bond, W is attached by a single bond; and when M is attached by a single bond, W is attached by a double bond;

U represents O, S, $NR^8$ or $CR^{10}R^{11}$;

E represents $CR^{10}$, $CR^{10}R^{11}$ or S, provided that when E is attached by a double bond, it is $CR^{10}$;

each G, at each occurrence, independently represents hydrogen, halogen, hydroxyl, cyano, nitro, azido, $NR^8R^9$, substituted or unsubstituted $C_{1-6}$ alkyl, substituted or unsubstituted $C_{1-6}$ alkoxy, or substituted or unsubstituted $C_{3-8}$ cycloalkyl, and if there are multiple G groups, they each may be the same or different;

q represents an integer of from 0 to 5;

$Ar_1$ represents $C_{6-14}$ aryl or 5- to 14-membered heteroaryl;

each $R^1$, at each occurrence, represents hydrogen, halogen, —OH, —CN, —$NO_2$, —$NR^8R^9$, substituted or unsubstituted $C_{1-6}$ alkyl, substituted or unsubstituted $C_{1-6}$ alkoxy, substituted or unsubstituted $C_{1-6}$ haloalkyl, substituted or unsubstituted $C_{1-6}$ alkylthio, substituted or unsubstituted $C_{3-8}$ cycloalkyl, substituted or unsubstituted 3- to 10-membered heterocycloalkyl, substituted or unsubstituted $C_{2-10}$ alkenyl, or substituted or unsubstituted $C_{2-10}$ alkynyl, and if there are multiple $R^1$ groups, they each may be the same or different;

m represents an integer of from 0 to 7;

X represents $CH_2$, —S—, —O— or —$NR^8$—;

$R^2$ and $R^3$, at each occurrence, each independently represent hydrogen, substituted or unsubstituted $C_{1-6}$ alkyl, substituted or unsubstituted $C_{1-6}$ alkoxy, substituted or unsubstituted $C_{6-14}$ aryl, substituted or unsubstituted $C_{7-20}$ aralkyl, or substituted or unsubstituted $C_{3-8}$ cycloalkyl; or $R^2$ and $R^3$ together with the carbon atom to which they are attached, form substituted or unsubstituted $C_{3-8}$ cycloalkyl, or substituted or unsubstituted 3- to 10-membered heterocycloalkyl;

$R^4$ and $R^5$, at each occurrence, each independently represent hydrogen, substituted or unsubstituted $C_{1-6}$ alkyl, substituted or unsubstituted $C_{1-6}$ alkoxy, substituted or unsubstituted $C_{6-14}$ aryl, substituted or unsubstituted $C_{7-20}$ aralkyl, or substituted or unsubstituted $C_{3-8}$ cycloalkyl group; or $R^4$ and $R^5$ together with the carbon atom to which they are attached, form substituted or unsubstituted $C_{3-8}$ cycloalkyl, or substituted or unsubstituted 3- to 10-membered heterocycloalkyl; or $R^3$ and $R^4$ are linked to each other, together with the carbon atoms to which they each are attached, form substituted or unsubstituted $C_{3-8}$ cycloalkyl, or substituted or unsubstituted 3- to 10-membered heterocycloalkyl;

$R^6$ represents hydrogen, substituted or unsubstituted $C_{1-6}$ alkyl, substituted or unsubstituted $C_{3-8}$ cycloalkyl, substituted or unsubstituted $C_{6-14}$ aryl group, substituted or unsubstituted $C_{7-20}$ aralkyl, or substituted or unsubstituted $C_{1-6}$ alkoxy;

each $R^7$, at each occurrence, independently represents hydrogen, halogen, —OH, —CN, —$NO_2$, —$NR^8R^9$, substituted or unsubstituted $C_{1-6}$ alkyl, substituted or unsubstituted $C_{1-6}$ haloalkyl, substituted or unsubstituted $C_{1-6}$ alkylthio, substituted or unsubstituted $C_{3-8}$ cycloalkyl, substituted or unsubstituted 3- to 10-membered heterocycloalkyl, substituted or unsubstituted $C_{2-10}$ alkynyl, or substituted or unsubstituted $C_{1-6}$ alkoxy, and if there are multiple $R^7$ groups, they each may be the same or different; or $R^6$ and $R^7$ are linked to each other, together with the carbon atoms therebetween, form substituted or unsubstituted $C_{3-8}$ carbocyclyl or 3- to 10-membered heterocyclyl;

n represents an integer of from 0 to 7;

$Ar_2$ represents $C_{6-14}$ aryl or 5- to 14-membered heteroaryl;

r and s each independently represent 1, 2 or 3;

$R^8$ and $R^9$, at each occurrence, each independently represent hydrogen, substituted or unsubstituted $C_{1-6}$ alkyl, or substituted or unsubstituted $C_{3-8}$ cycloalkyl, if there are multiple $R^8$ and $R^9$ groups, they each may be the same or different, and preferably, $R^8$ represents hydrogen, $C_{1-6}$ alkyl or $C_{3-8}$ cycloalkyl, and $R^9$ represents hydrogen; and $R^{10}$ and $R^{11}$, at each occurrence, each independently represent hydrogen, substituted or unsubstituted $C_{1-6}$ alkyl, or substituted or unsubstituted $C_{3-8}$ cycloalkyl, or $R^{10}$ and $R^{11}$ together form $C_{1-6}$ alkylene, and if there are multiple $R^{10}$ and $R^{11}$ groups, they each may be the same or different.

2. The compound of claim 1, a pharmaceutically acceptable salt, ester, solvate, isomer thereof, any crystalline form or racemate of the foregoing, a metabolite form of the foregoing, or a mixture of the foregoing, wherein the compound is a compound of Formula (Ia)

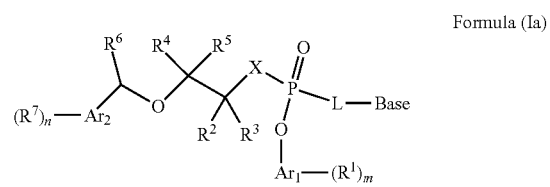

Formula (Ia)

wherein

L-Base represents a group of Formula (f) or Formula (g):

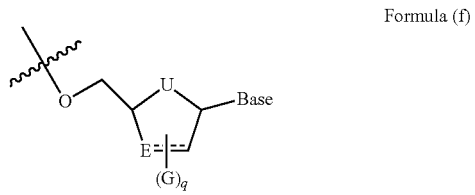

Formula (f)

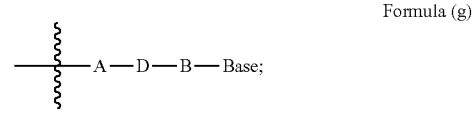

Formula (g)

Base represents a group of Formula (a) or Formula (b):

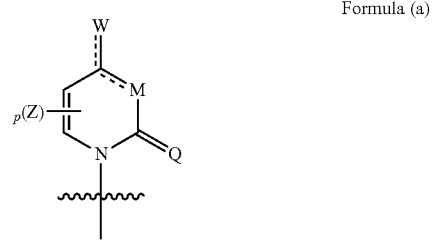

Formula (a)

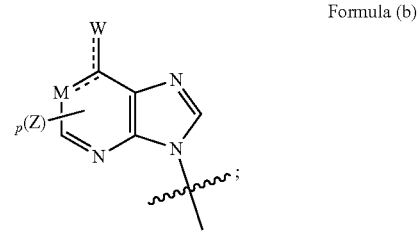

Formula (b)

wherein

===== represents a single bond or a double bond;

M represents N or NW;

W represents $NR^8R^9$ or O;

Q represents O or S;

each Z, at each occurrence, independently represents hydrogen, halogen, NR$^8$R$^9$, substituted or unsubstituted C$_{1-6}$ alkyl, substituted or unsubstituted C$_{1-6}$ alkoxy, or substituted or unsubstituted C$_{3-8}$ cycloalkyl, and if there are multiple Z groups, they each may be the same or different;

p represents an integer of from 0 to 2;

provided that when M is attached by a double bond, W is attached by a single bond, M represents N, and W represents NR$^8$R$^9$; and when M is attached by a single bond, W is attached by a double bond, M represents NR$^8$, and W represents O;

U represents O, S or CR$^{10}$R$^{11}$;

E represents CR$^{10}$, CR$^{10}$R$^{11}$ or S, provided that when E is attached by a double bond, it is CR$^{10}$;

each G, at each occurrence, independently represents hydrogen, halogen, hydroxy, azido, substituted or unsubstituted C$_{1-6}$ alkyl, substituted or unsubstituted C$_{1-6}$ alkoxy, or substituted or unsubstituted C$_{3-8}$ cycloalkyl, and if there are multiple G groups, they each may be the same or different;

q represents an integer of from 0 to 4;

A represents substituted or unsubstituted C$_{1-6}$ alkylene;

B represents substituted or unsubstituted C$_{1-6}$ alkylene;

D represents O, S or NR$^8$;

Ar$_1$ represents C$_{6-10}$ aryl or C$_{3-10}$ heteroaryl;

each R$^1$, at each occurrence, independently represents hydrogen, halogen, substituted or unsubstituted C$_{1-6}$ alkyl, substituted or unsubstituted C$_{1-6}$ alkoxy, substituted or unsubstituted C$_{3-8}$ cycloalkyl, substituted or unsubstituted C$_{3-8}$ heterocycloalkyl, substituted or unsubstituted C$_{2-10}$ alkenyl group, or substituted or unsubstituted C$_{2-10}$ alkynyl, and if there are multiple R$^1$ groups, they each may be the same or different;

m represents an integer of from 0 to 7;

X represents —O— or —NR$^8$—;

R$^2$ and R$^3$ each independently represent hydrogen, substituted or unsubstituted C$_{1-6}$ alkyl, substituted or unsubstituted C$_{3-8}$ cycloalkyl; or R$^2$ and R$^3$ together with the carbon atom to which they are attached, form substituted or unsubstituted C$_{3-8}$ cycloalkyl, or substituted or unsubstituted C$_{3-8}$ heterocycloalkyl;

R$^4$ and R$^5$ each independently represent hydrogen, substituted or unsubstituted C$_{1-6}$ alkyl, substituted or unsubstituted C$_{3-8}$ cycloalkyl; or R$^4$ and R$^5$ together with the carbon atom to which they are attached, form substituted or unsubstituted C$_{3-8}$ cycloalkyl, or substituted or unsubstituted C$_{3-8}$ heterocycloalkyl; or R$^3$ and R$^4$ are linked to each other, together with the carbon atoms to which they each are attached, form substituted or unsubstituted C$_{4-8}$ cycloalkyl, or substituted or unsubstituted C$_{4-8}$ heterocycloalkyl;

R$^6$ represents hydrogen, substituted or unsubstituted C$_{1-6}$ alkyl, substituted or unsubstituted C$_{3-8}$ cycloalkyl, or substituted or unsubstituted C$_{1-6}$ alkoxy;

each R$^7$, at each occurrence, independently represents hydrogen, halogen, substituted or unsubstituted C$_{1-6}$ alkyl, substituted or unsubstituted C$_{3-8}$ cycloalkyl, or substituted or unsubstituted C$_{1-6}$ alkoxy, and if there are multiple R$^7$ groups, they each may be the same or different; or R$^6$ and R$^7$ are linked to each other, together with the carbon atoms therebetween, form substituted or unsubstituted C$_{4-8}$ carbocyclyl or C$_{4-8}$ heterocyclyl;

n represents an integer of from 0 to 7;

Are represents C$_{6-10}$ aryl or C$_{3-10}$ heteroaryl;

R$^8$ and R$^9$, at each occurrence, each independently represent hydrogen, substituted or unsubstituted C$_{1-6}$ alkyl, or substituted or unsubstituted C$_{3-8}$ cycloalkyl, and if there are multiple R$^8$ and R$^9$ groups, they each may be the same or different, and R$^{10}$ and R$^{11}$, at each occurrence, each independently represent hydrogen, substituted or unsubstituted C$_{1-6}$ alkyl, or substituted or unsubstituted C$_{3-8}$ cycloalkyl, or R$^{10}$ and R$^{11}$ together form C$_{1-6}$ alkylene, and if there are multiple R$^{10}$ and R$^{11}$ groups, they each may be the same or different.

3. The compound of claim 1, a pharmaceutically acceptable salt, ester, solvate, isomer thereof, any crystalline form or racemate of the foregoing, a metabolite form of the foregoing, or a mixture of the foregoing, wherein r and s are both 1;

Base is selected from the group consisting of:

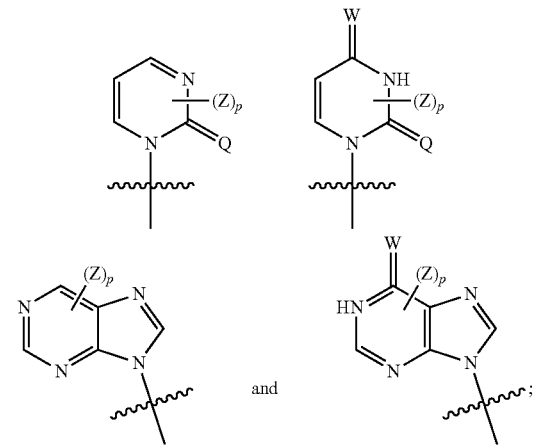

L is selected from the group consisting of C$_{1-6}$ alkylene, C$_{2-6}$ alkenylene and C$_{2-6}$ alkynylene, which are optionally substituted by one or more G groups, and the alkylene, alkenylene or alkynylene is optionally interrupted by one or more —O—, —NR$^8$— or —S—; or L is selected from the group consisting of:

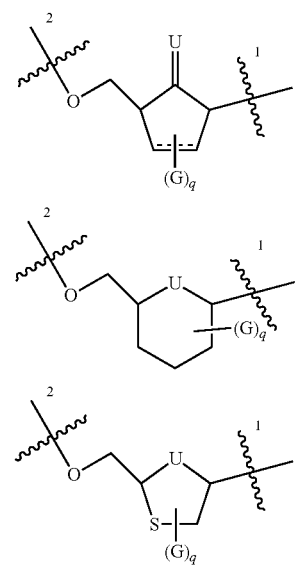

-continued

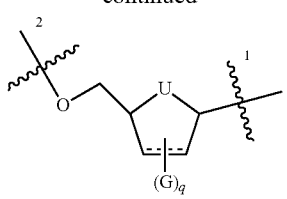

wherein

⚌ represents a single bond or a double bond, position 1 is attached to the Base, and position 2 is attached to the phosphorus atom (P);

X, U, W and Q, at each occurrence, are each independently selected from the group consisting of $CH_2$, O, S and $NR^8$;

G and Z, at each occurrence, are each independently selected from the group consisting of halogen, —OH, —CN, —$NO_2$, —$NR^8R^9$, —$N_3$, $C_{1-6}$ alkyl and $C_{3-6}$ cycloalkyl;

p and q, at each occurrence, are each independently 0, 1, 2, 3, 4 or 5, provided that p is not greater than the number of substitutable positions on the corresponding group and q is not greater than the number of substitutable positions on the corresponding group; when p is greater than 1, each Z may be the same or different; and when q is greater than 1, each G may be the same or different;

$Ar_1$ and $Ar_2$ are each independently selected from the group consisting of $C_{6-14}$ aryl and 5- to 14-membered heteroaryl;

m and n are each independently selected from the group consisting of 1, 2, 3, 4 or 5;

$R^1$ and $R^7$ are each independently selected from the group consisting of hydrogen, halogen, —OH, —CN, —$NO_2$, —$NR^8R^9$, $C_{1-6}$ alkyl, $C_{1-6}$ haloalkyl, $C_{1-6}$ alkoxy, $C_{1-6}$ alkylthio, $C_{3-6}$ cycloalkyl, 3- to 10-membered heterocycloalkyl and $C_{2-6}$ alkynyl;

$R^8$ and $R^9$, at each occurrence, each independently represent hydrogen, $C_{1-6}$ alkyl and $C_{3-6}$ cycloalkyl;

$R^2$ and $R^3$ are each independently selected from the group consisting of hydrogen, $C_{1-6}$ alkyl, $C_{3-6}$ cycloalkyl, $C_{1-6}$ alkoxy, $C_{6-14}$ aryl and $C_{7-20}$ aralkyl, the alkyl, cycloalkyl, alkoxy, aryl and aralkyl are each optionally substituted by one or more substituents selected from the group consisting of halogen, —OH, —CN and —$NO_2$; or $R^2$ and $R^3$ together with the carbon atom to which they are attached, form $C_{3-6}$ cycloalkyl or 3- to 10-membered heterocycloalkyl;

$R^4$ and $R^5$ are each independently selected from the group consisting of hydrogen, $C_{1-6}$ alkyl, $C_{3-6}$ cycloalkyl, $C_{1-6}$ alkoxy, $C_{6-14}$ aryl and $C_{7-20}$ aralkyl, and the alkyl, cycloalkyl, alkoxy, aryl and aralkyl are each optionally substituted by one or more substituents selected from the group consisting of halogen, —OH, —CN and —$NO_2$; or $R^4$ and $R^5$ together with the carbon atom to which they are attached, form $C_{3-6}$ cycloalkyl or 3- to 10-membered heterocycloalkyl; or $R^3$ and $R^4$ together with the carbon atoms to which they are attached, form $C_{3-6}$ cycloalkyl or 3- to 10-membered heterocycloalkyl; and $R^6$ is selected from the group consisting of hydrogen, $C_{1-6}$ alkyl, $C_{3-6}$ cycloalkyl, $C_{1-6}$ alkoxy, $C_{6-14}$ aryl and $C_{7-20}$ aralkyl, the alkyl, cycloalkyl, alkoxy, aryl and aralkyl are each optionally substituted by one or more substituents selected from the group consisting of halogen, —OH, —CN and —$NO_2$; or $R^6$ and $R^7$ together with the carbon atom to which they are attached, form $C_{3-6}$ cycloalkyl or 3- to 10-membered heterocycloalkyl fused to $Ar_2$.

4. The compound of claim 1, a pharmaceutically acceptable salt, ester, solvate, isomer thereof, any crystalline form or racemate of the foregoing, a metabolite form of the foregoing, or a mixture of the foregoing, wherein Base is a member selected from the group consisting of the formula

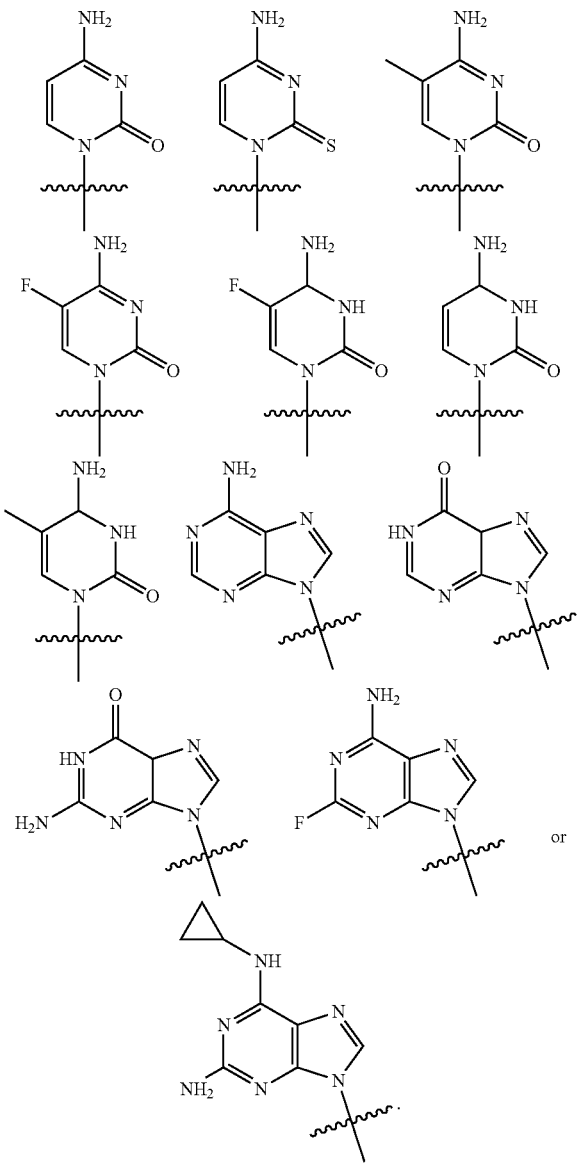

5. The compound of claim 1, a pharmaceutically acceptable salt, ester, solvate, isomer thereof, any crystalline form or racemate of the foregoing, a metabolite form of the foregoing, or a mixture of the foregoing, wherein L-Base is a member selected from the group consisting of the formula

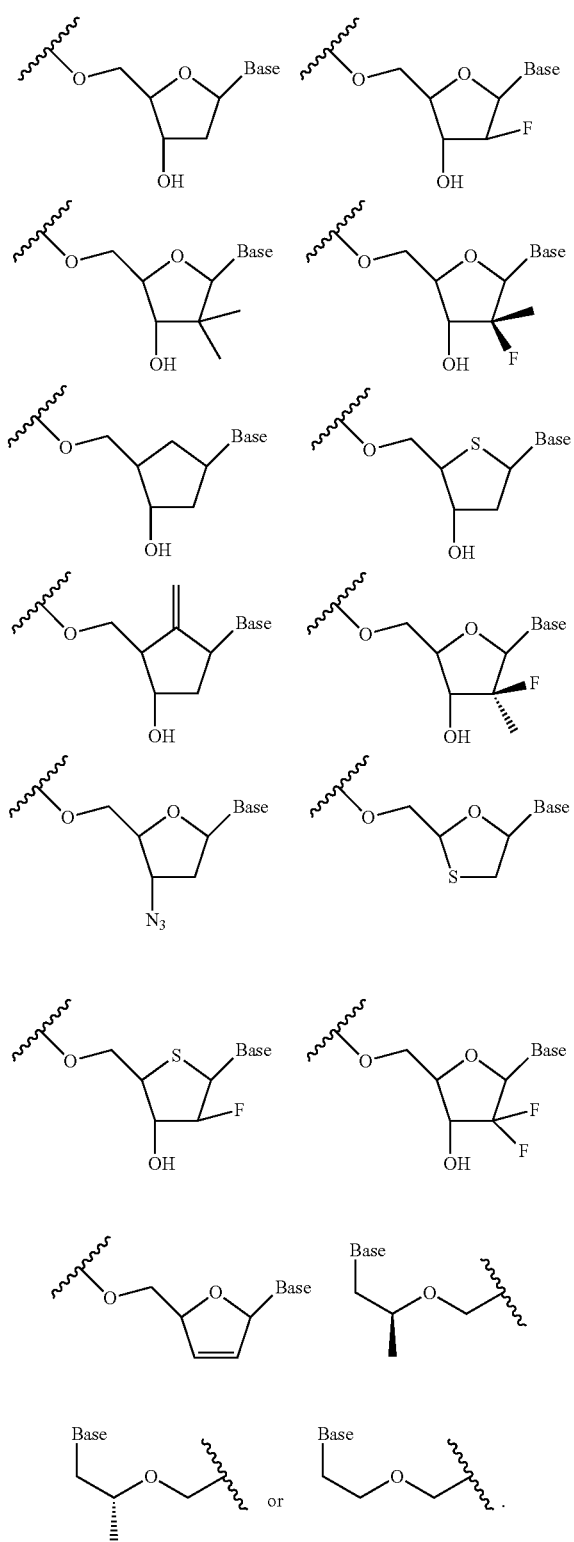

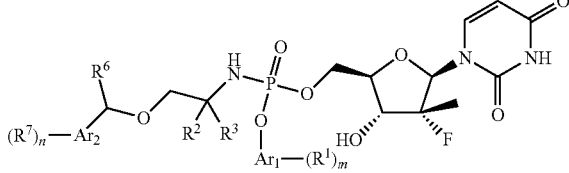

wherein $R^1$, $R^2$, $R^3$, $R^6$, $R^7$, m, n, An and Ara are as defined in claim 1;
the compound is a compound of Formula (IIa)

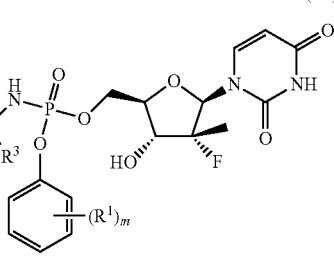

wherein $R^1$, $R^2$, $R^3$, $R^6$, $R^7$, m and n are as defined in claim 1; and
the compound is a compound of Formula (IIb)

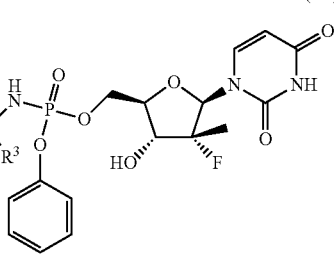

wherein $R^2$, $R^3$, $R^7$ and n are as defined in claim 1.

7. The compound of claim 1, a pharmaceutically acceptable salt, ester, solvate, isomer thereof, any crystalline form or racemate of the foregoing, a metabolite form of the foregoing, or a mixture of the foregoing, wherein the compound is a member selected from the group consisting of Formula (III), Formula (IIIa), Formula (IIIb), Formula (IIIc-1) and Formula (IIIc-2):

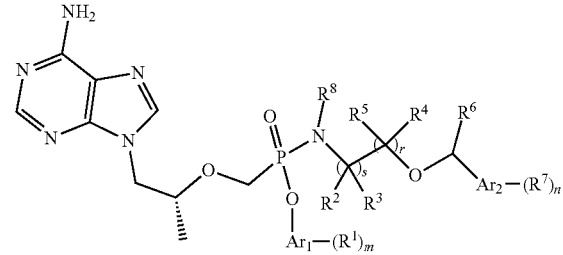

6. The compound of claim 1, a pharmaceutically acceptable salt, ester, solvate, isomer thereof, any crystalline form or racemate of the foregoing, a metabolite form of the foregoing, or a mixture of the foregoing, wherein the compound is a member selected from the group consisting of Formula (II), Formula (IIa) and Formula (IIb):

wherein $R^1$, $R^2$, $R^3$, $R^4$, $R^5$, $R^6$, $R^7$, $R^8$, m, n, s, r, $Ar_1$ and $Ar_2$ are as defined in claim 1;

the compound is a compound of Formula (IIIa)

Formula (IIIa)

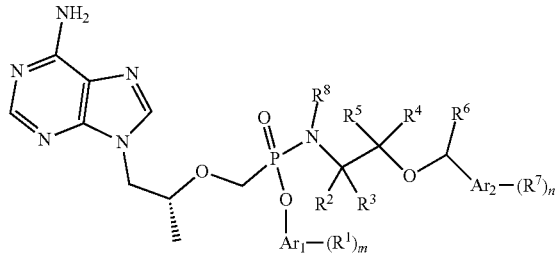

wherein $R^1$, $R^2$, $R^3$, $R^4$, $R^5$, $R^6$, $R^7$, $R^8$, m, n, $Ar_1$ and $Ar_2$ are as defined in claim 1;

the compound is a compound of Formula (IIIb)

Formula (IIIb)

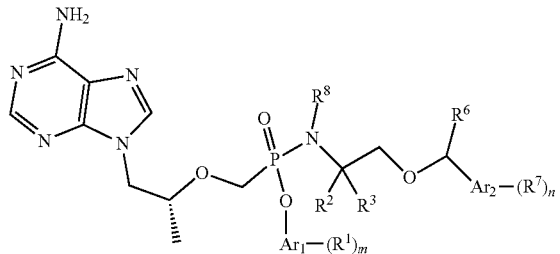

wherein $R^1$, $R^2$, $R^3$, $R^6$, $R^7$, $R^8$, m, n, $Ar_1$ and $Ar_2$ are as defined in claim 1; and the compound is a compound of Formula (IIIc-1) or Formula (IIIc-2), Formula (IIIc-1)

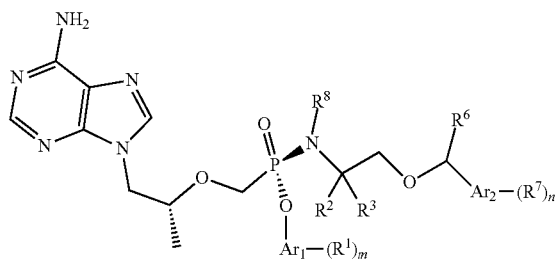

Formula (IIIc-2)

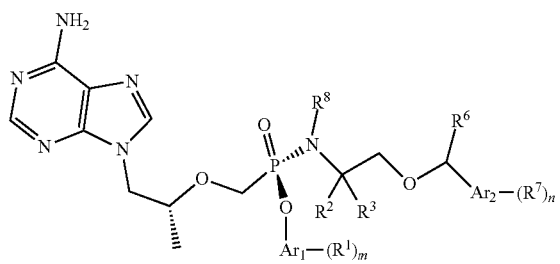

wherein $R^1$, $R^2$, $R^3$, $R^6$, $R^7$, $R^8$, m, n, $Ar_1$ and $Ar_2$ are as defined in claim 1.

8. The compound of claim 1, a pharmaceutically acceptable salt, ester, solvate, isomer thereof, any crystalline form or racemate of the foregoing, a metabolite form of the foregoing, or a mixture of the foregoing, wherein the compound is a compound of Formula (IV)

Formula (IV)

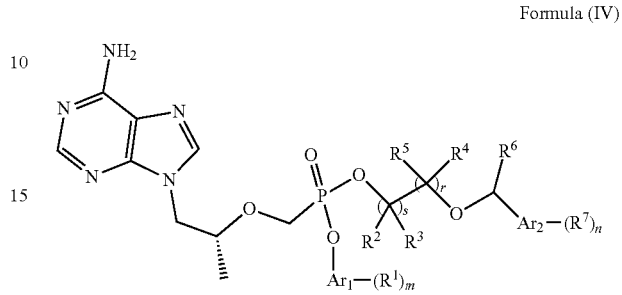

wherein $R^1$, $R^2$, $R^3$, $R^4$, $R^5$, $R^6$, $R^7$, m, n, s, r, $Ar_1$ and $Ar_2$ are as defined in claim 1.

9. The compound of claim 1, a pharmaceutically acceptable salt, ester, solvate, isomer thereof, any crystalline form or racemate of the foregoing, a metabolite form of the foregoing, or a mixture of the foregoing, wherein the compound is a member selected from the group of:

1

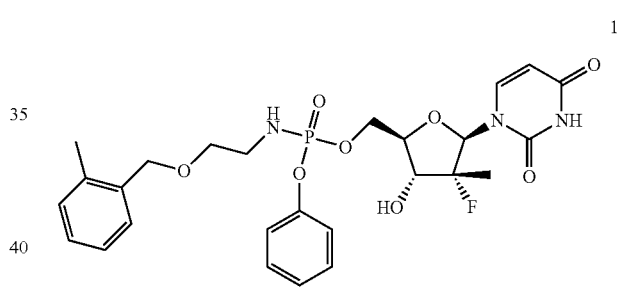

2

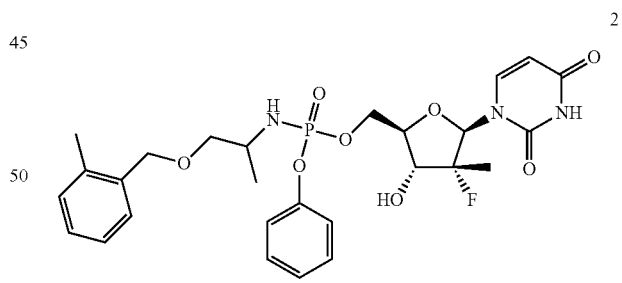

3

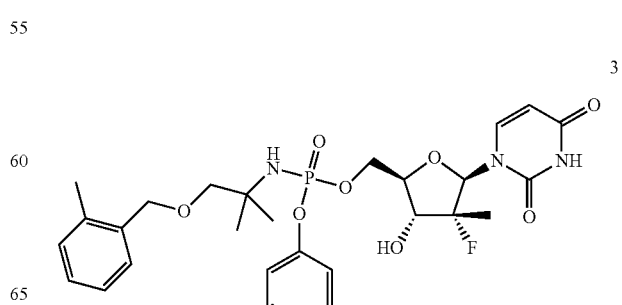

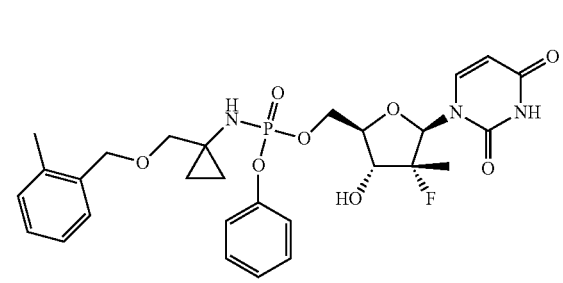
4
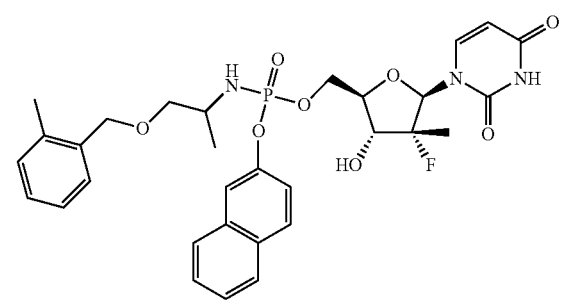
5
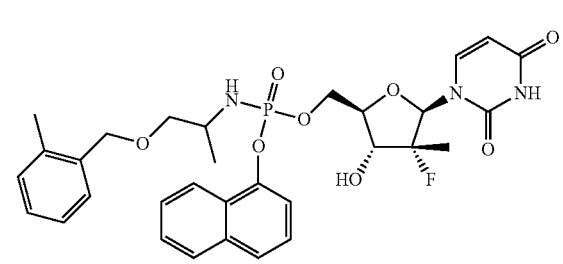
6
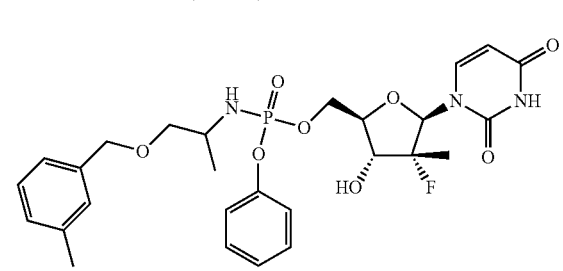
7
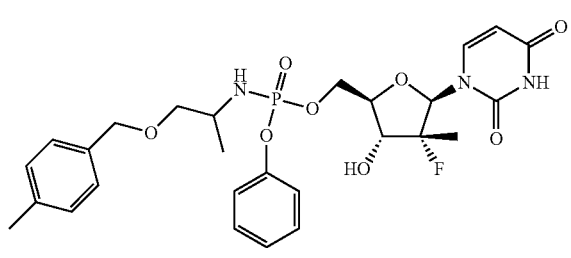
8
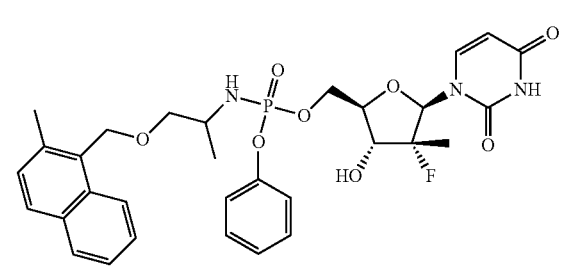
9
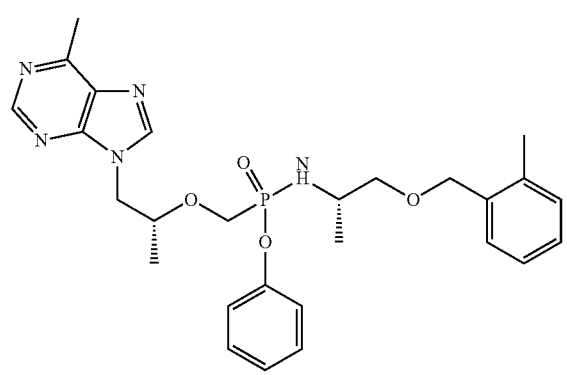
10
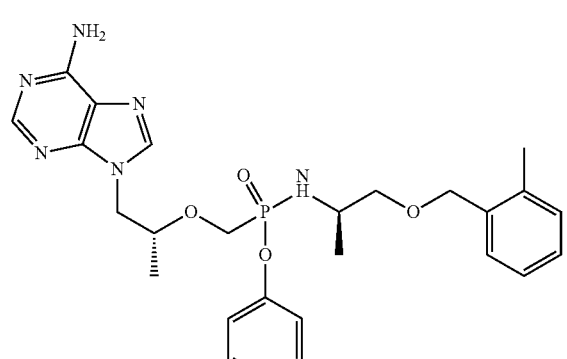
11
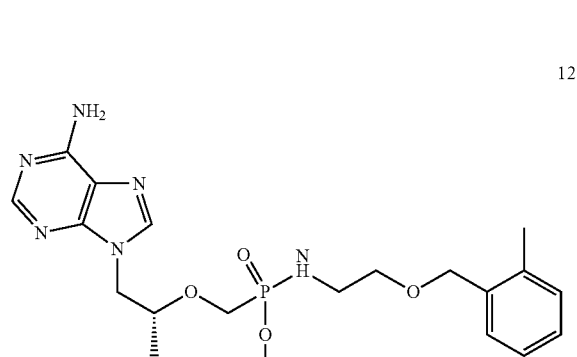
12
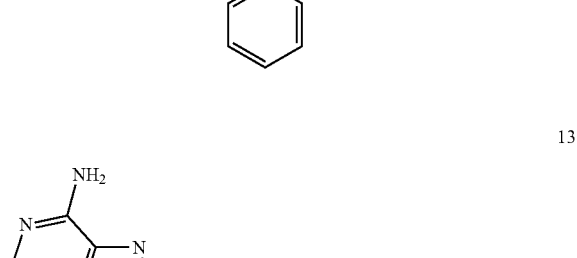
13
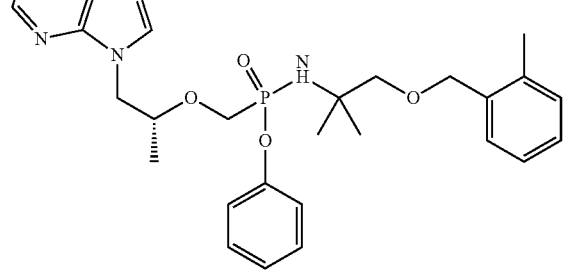

14
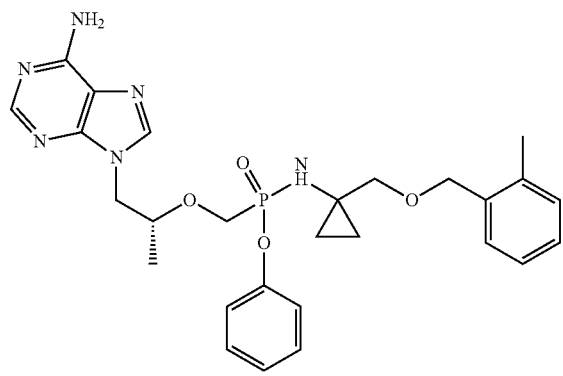
15
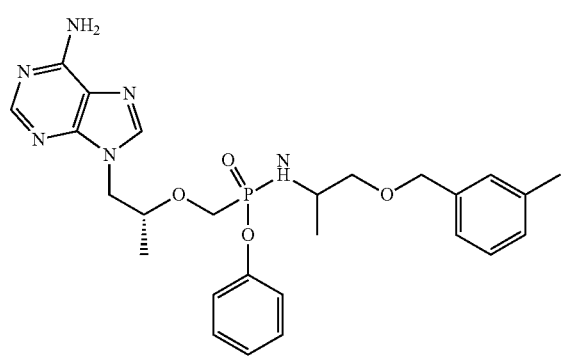
16
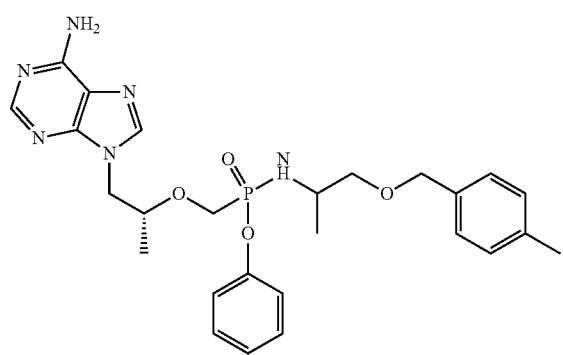
17
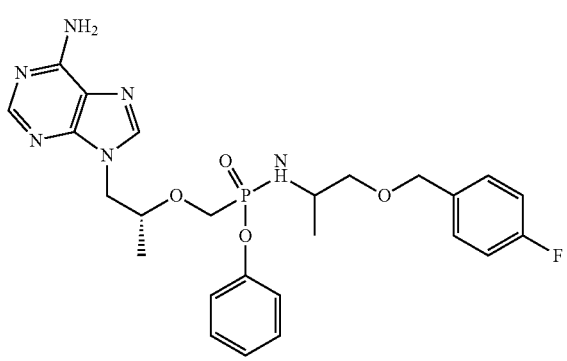
18
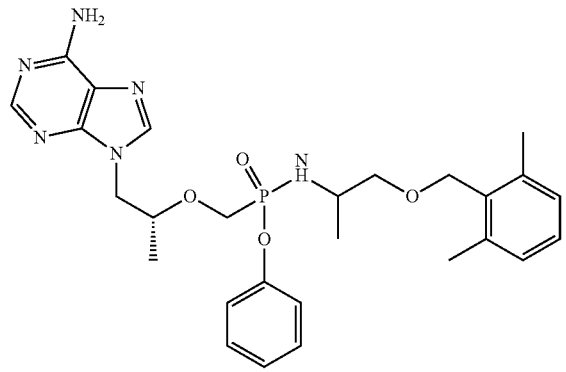
19
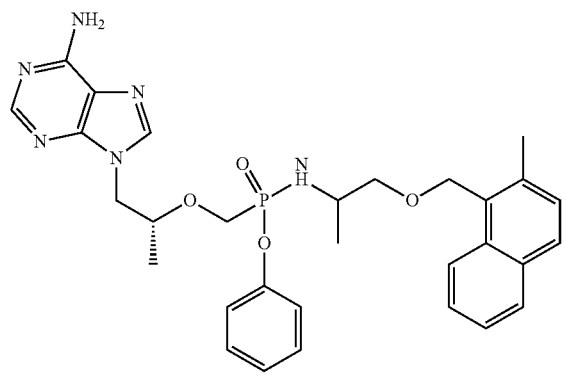
20
21

22
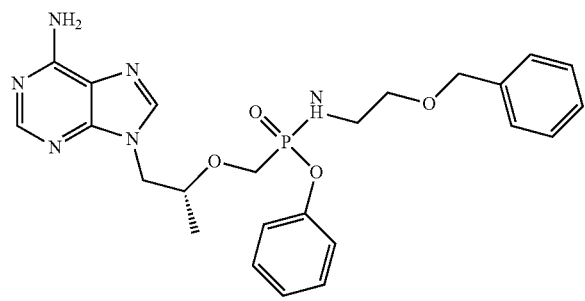
23
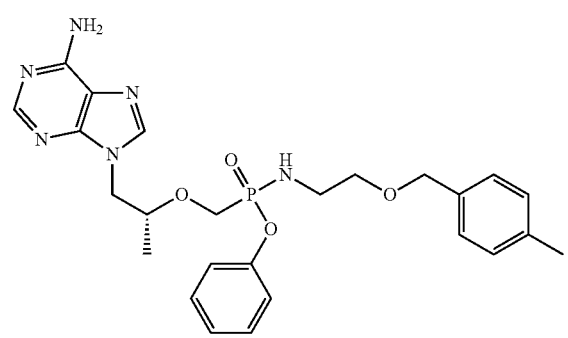
24
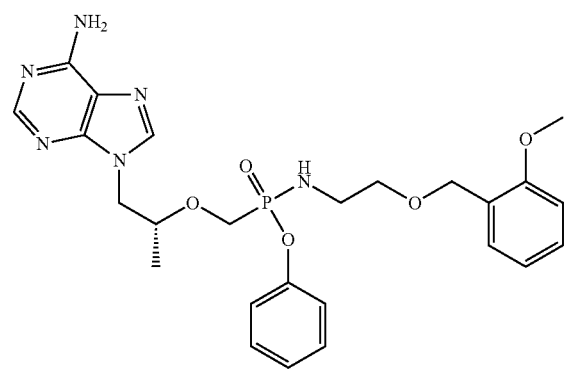
25
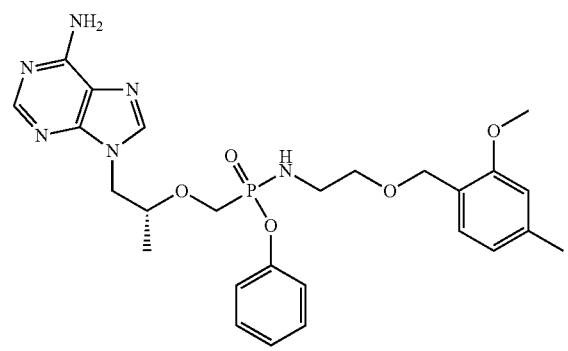
26
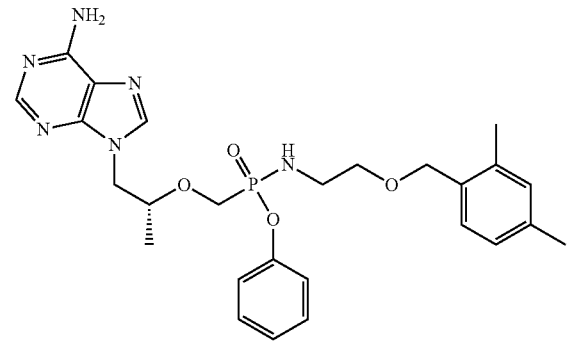
27
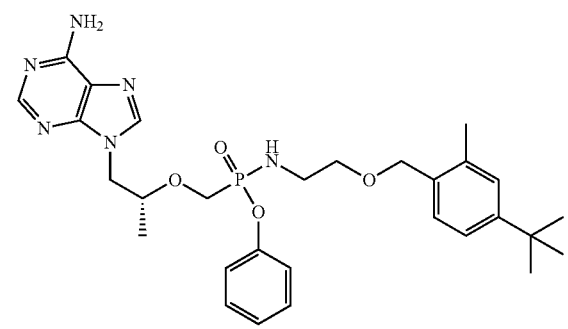
28
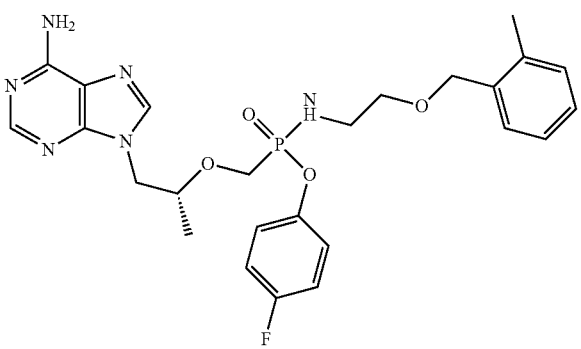
29

30
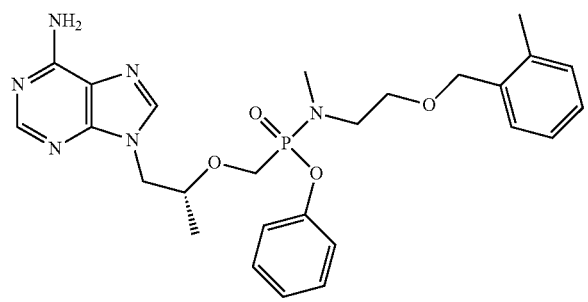
31
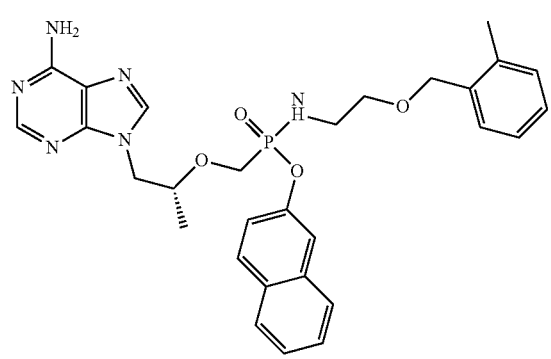
32
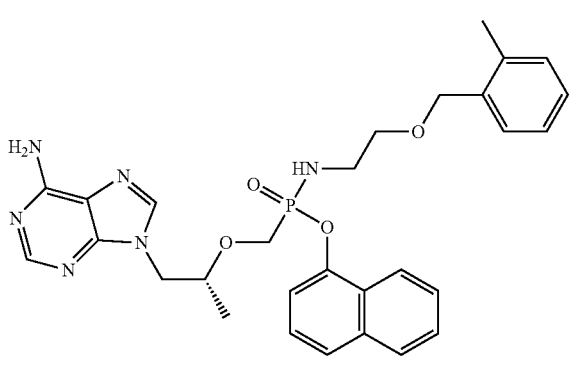
33
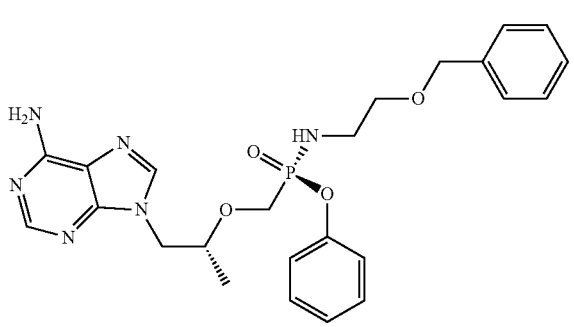
34
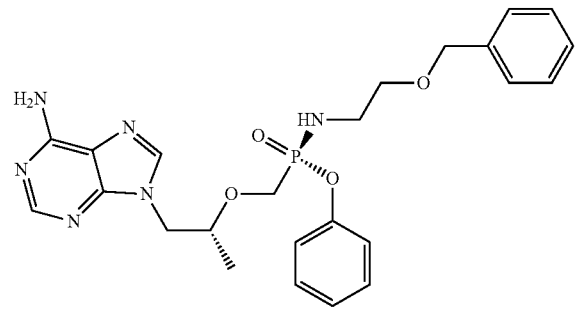
35
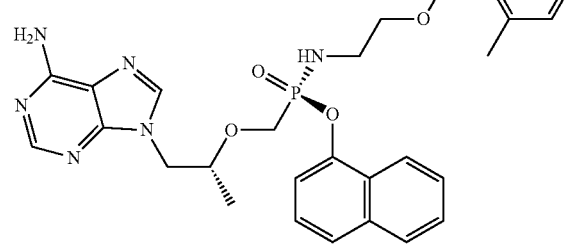
36
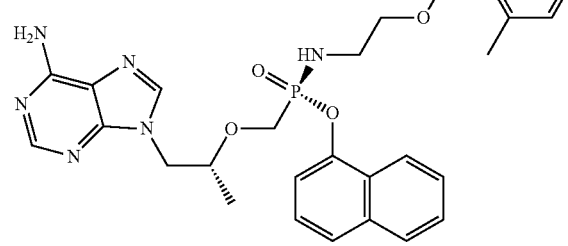
37
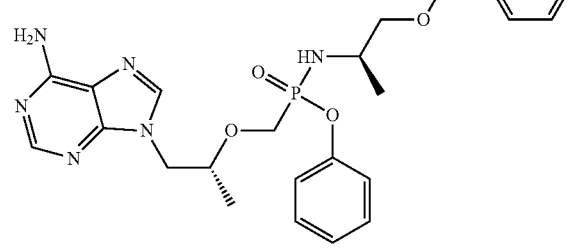

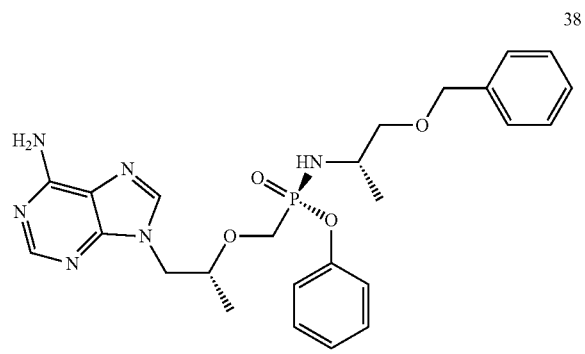
38
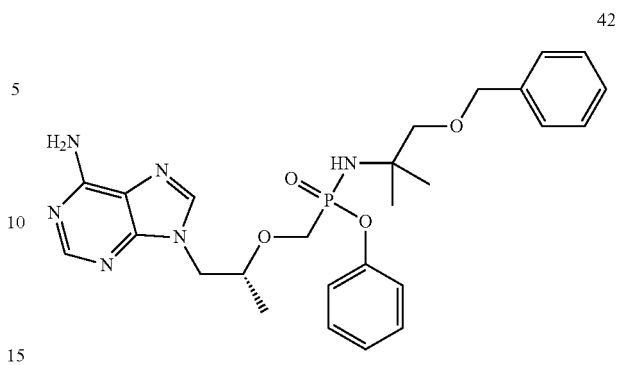
42
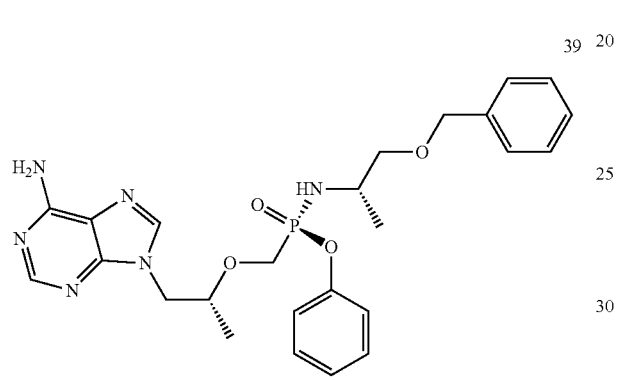
39
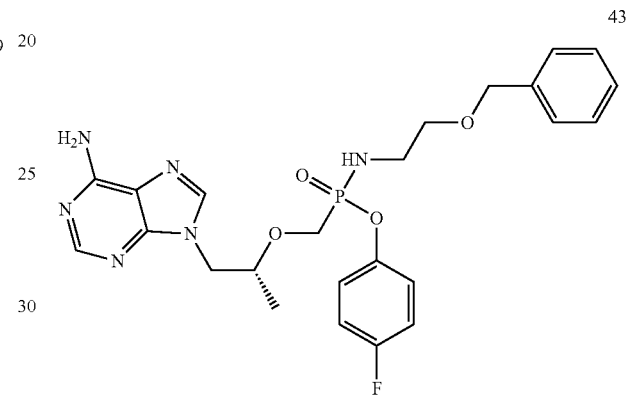
43
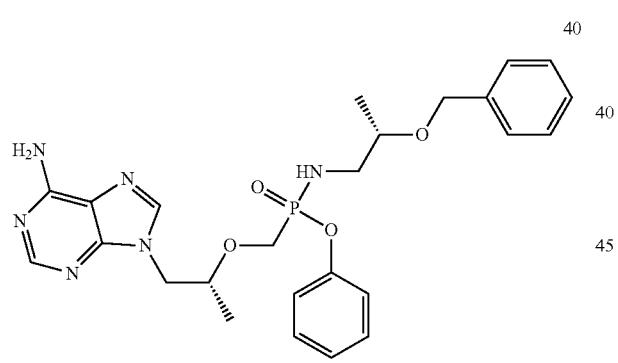
40
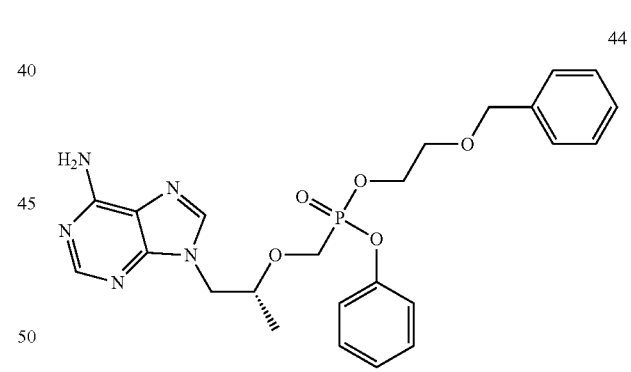
44
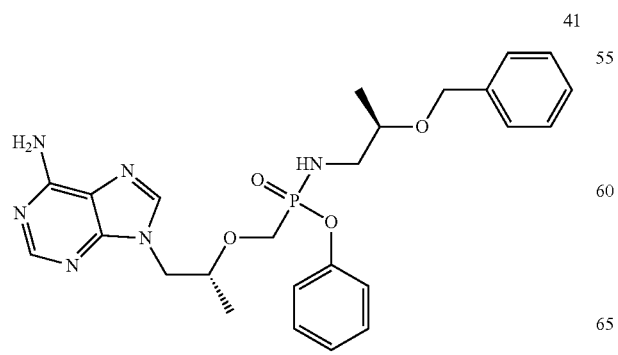
41
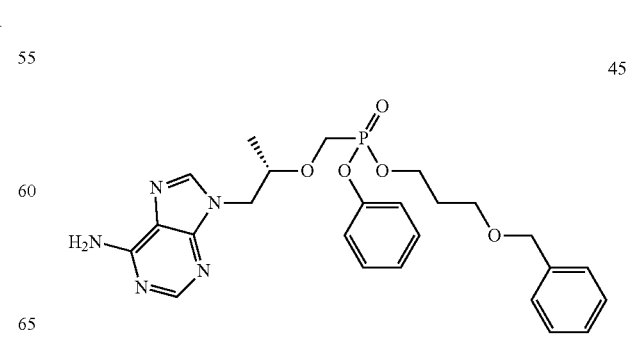
45

-continued

46
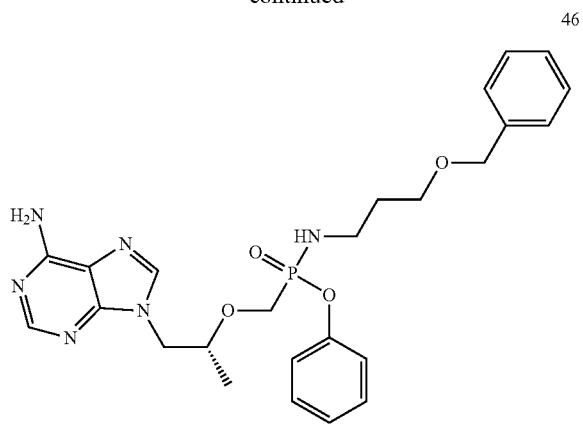

47
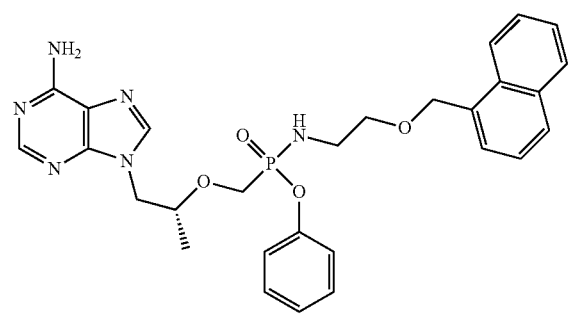

48
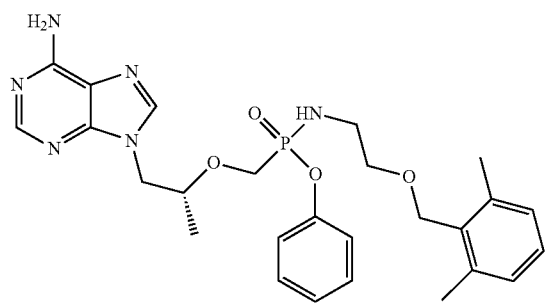

49
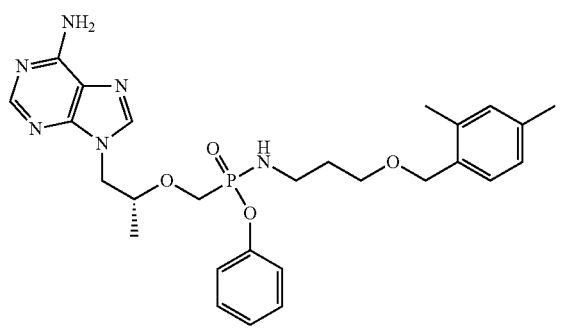

-continued

50
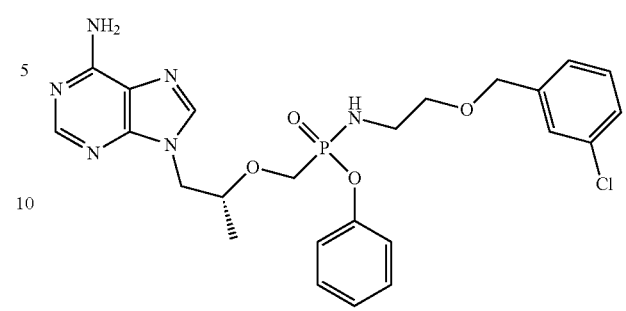

51, 52, 53
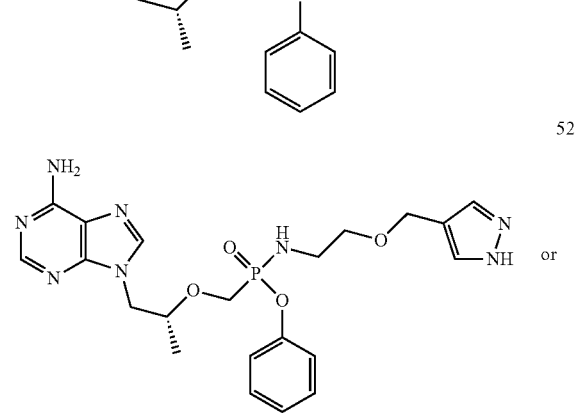

10. A pharmaceutical composition comprising the compound of claim 1, a pharmaceutically acceptable salt, ester, solvate, isomer thereof, any crystalline form or racemate of the foregoing, a metabolite form of the foregoing, or a mixture of the foregoing, preferably further comprising a pharmaceutically acceptable adjuvant, and more preferably further comprising an additional active ingredient(s) that can be co-administered with the compound of claim 1, a pharmaceutically acceptable salt, ester, solvate, isomers thereof, any crystalline form or racemate of the foregoing, a metabolite form of the foregoing, or a mixture of the foregoing, wherein the additional active ingredient(s) is(are) preferably selected from the group consisting of interferons, ribavirin or analogues thereof, HCV NS3 protease inhibitors, α-glucosidase 1 inhibitors, hepatoprotective agents, non-nucleoside inhibitors of HCV NS5B polymerase, HCV NS5A inhibitors, TLR-7 agonists, cyclophilin inhibitors, HCV IRES inhibitors, pharmacokinetic enhancers, and other drugs or therapeutic agents for the treatment of HCV, or a combination thereof, and the pharmaceutical composition is in a form selected from the group consisting of a solid formulation, a semisolid formulation, a liquid formulation, or a gaseous formulation.

11. The composition of claim 10, wherein the composition comprises the compound, a pharmaceutically acceptable salt, ester, solvate, isomer thereof, any crystalline form or racemate of the foregoing, a metabolite form of the foregoing, or a mixture of the foregoing in an amount of 0.01-1000 mg.

12. A method for prophylactically treating or treating a NS5B polymerase mediated disease, a DNA polymerase mediated disease or a reverse transcriptase mediated disease, comprising administering to a subject in need thereof an effective amount of the compound of claim 1, a pharmaceutically acceptable salt, ester, solvate, isomer thereof, any crystalline form or racemate of the foregoing, a metabolite form of the foregoing, or a mixture of the foregoing.

13. A method for prophylactically treating or treating a viral disease or cancer, comprising administering to a subject in need thereof an effective amount of the compound of claim 1, a pharmaceutically acceptable salt, ester, solvate, isomer thereof, any crystalline form or racemate of the foregoing, a metabolite form of the foregoing, or a mixture of the foregoing, wherein the viral disease is preferably selected from the group consisting of viral hepatitis type A, viral hepatitis type B, viral hepatitis type C, influenza, herpes, and acquired immunodeficiency syndrome (AIDS).

14. A method for preparing the compound of claim 1, a pharmaceutically acceptable salt, ester, solvate, isomer thereof, any crystalline form or racemate of the foregoing, a metabolite form of the foregoing, or a mixture of the foregoing, comprising the following steps:

wherein in step 1, reacting a phosphorus oxyhalide of Formula 2 with a compound of Formula 1 to obtain a compound of Formula 3;

wherein in step 2, reacting the compound of Formula 3 with a compound of Formula 4 to obtain a compound of Formula 5;

wherein in step 3, reacting the compound of Formula 5 with pentafluorophenol of Formula 6 to obtain a compound of Formula 7; and wherein in step 4, reacting the compound of Formula 7 with a compound of Formula 8 to obtain a compound of Formula (I);

wherein $R^1$, $R^2$, $R^3$, $R^4$, $R^5$, $R^6$, $R^7$, m, n, s, r, X, $Ar_1$, $Ar_2$, L and Base are as defined in claim 1; and each Y is the same or different, and is each independently selected from halogen;

or

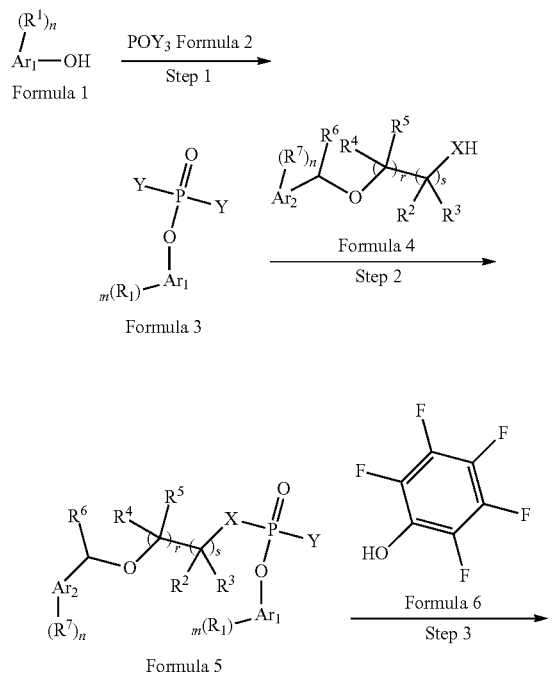

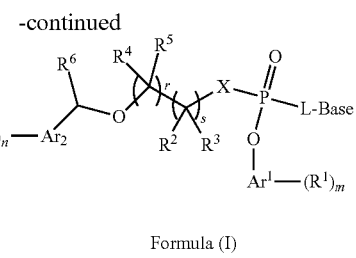

Formula (I)

wherein $R^1$, $R^2$, $R^3$, $R^4$, $R^5$, $R^6$, $R^7$, m, n, s, r, X, $Ar_1$, $Ar_2$, L and Base are as defined in claim 1;
or Scheme 3

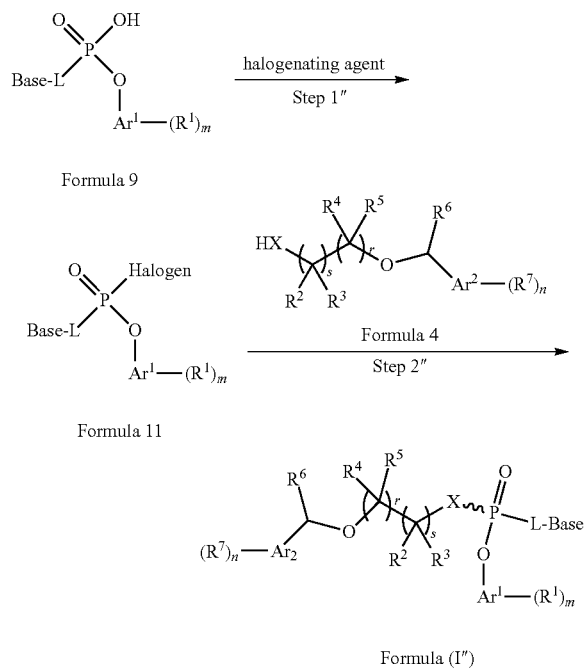

Formula (I″)

wherein

∿∿ represents either a solid wedge (▬◀) or dashed wedge (┉┉┉) chemical bond; and
$R^1$, $R^2$, $R^3$, $R^4$, $R^5$, $R^6$, $R^7$, m, n, s, r, X, $Ar_1$, $Ar_2$, L and Base are as defined in claim 1.

15. A method for prophylactically treating or treating a NS5B polymerase mediated disease, a DNA polymerase mediated disease or a reverse transcriptase mediated disease, comprising administering to a subject in need thereof an effective amount of the pharmaceutical composition of claim 10.

16. A method for prophylactically treating or treating a viral disease or cancer, comprising administering to a subject in need thereof an effective amount of the pharmaceutical composition of claim 10, wherein the viral disease is preferably selected from the group consisting of viral hepatitis type A, viral hepatitis type B, viral hepatitis type C, influenza, herpes, and acquired immunodeficiency syndrome (AIDS).

17. A pharmaceutical composition comprising the compound of claim 7, a pharmaceutically acceptable salt, ester, solvate, isomer thereof, any crystalline form or racemate of the foregoing, a metabolite form of the foregoing, or a mixture of the foregoing, preferably further comprising a pharmaceutically acceptable adjuvant, and more preferably further comprising an additional active ingredient(s) that can be co-administered with the compound of claim 7, a pharmaceutically acceptable salt, ester, solvate, isomers thereof, any crystalline form or racemate of the foregoing, a metabolite form of the foregoing, or a mixture of the foregoing, wherein the additional active ingredient(s) is(are) preferably selected from the group consisting of interferons, ribavirin or analogues thereof, HCV NS3 protease inhibitors, α-glucosidase 1 inhibitors, hepatoprotective agents, non-nucleoside inhibitors of HCV NS5B polymerase, HCV NS5A inhibitors, TLR-7 agonists, cyclophilin inhibitors, HCV IRES inhibitors, pharmacokinetic enhancers, and other drugs or therapeutic agents for the treatment of HCV, or a combination thereof, and the pharmaceutical composition is in the form of a solid formulation, a semisolid formulation, a liquid formulation, or a gaseous formulation.

18. The composition of claim 17, wherein the composition comprises the compound, a pharmaceutically acceptable salt, ester, solvate, isomer thereof, any crystalline form or racemate of the foregoing, a metabolite form of the foregoing, or a mixture of the foregoing in an amount of 0.01-1000 mg.

19. A method for prophylactically treating or treating a NS5B polymerase mediated disease, a DNA polymerase mediated disease or a reverse transcriptase mediated disease, comprising administering to a subject in need thereof an effective amount of the compound of claim 7, a pharmaceutically acceptable salt, ester, solvate, isomer thereof, any crystalline form or racemate of the foregoing, a metabolite form of the foregoing, or a mixture of the foregoing.

20. A method for prophylactically treating or treating a NS5B polymerase mediated disease, a DNA polymerase mediated disease or a reverse transcriptase mediated disease, comprising administering to a subject in need thereof an effective amount of the pharmaceutical composition of claim 17.

21. A method for prophylactically treating or treating a viral disease or cancer, comprising administering to a subject in need thereof an effective amount of the compound of claim 7, a pharmaceutically acceptable salt, ester, solvate, isomer thereof, any crystalline form or racemate of the foregoing, a metabolite form of the foregoing, or a mixture of the foregoing, wherein the viral disease is preferably selected from the group consisting of viral hepatitis type A, viral hepatitis type B, viral hepatitis type C, influenza, herpes, and acquired immunodeficiency syndrome (AIDS).

22. A method for prophylactically treating or treating a viral disease or cancer, comprising administering to a subject in need thereof an effective amount of the pharmaceutical composition of claim 17, wherein the viral disease is preferably selected from the group consisting of viral hepatitis type A, viral hepatitis type B, viral hepatitis type C, influenza, herpes, and acquired immunodeficiency syndrome (AIDS).

23. A pharmaceutical composition comprising the compound of claim 9, a pharmaceutically acceptable salt, ester, solvate, isomer thereof, any crystalline form or racemate of the foregoing, a metabolite form of the foregoing, or a mixture of the foregoing, preferably further comprising a pharmaceutically acceptable adjuvant, and more preferably further comprising an additional active ingredient(s) that can be co-administered with the compound of claim 9, a pharmaceutically acceptable salt, ester, solvate, isomers thereof, any crystalline form or racemate of the foregoing, a metabolite form of the foregoing, or a mixture of the foregoing, wherein the additional active ingredient(s) is(are) preferably selected from the group consisting of interferons, ribavirin or analogues thereof, HCV NS3 protease inhibitors, α-glucosidase 1 inhibitors, hepatoprotective agents, non-nucleoside inhibitors of HCV NS5B polymerase, HCV NS5A inhibitors, TLR-7 agonists, cyclophilin inhibitors, HCV IRES inhibitors, pharmacokinetic enhancers, and other drugs or therapeutic agents for the treatment of HCV, or a combination thereof, and the pharmaceutical composition is in the form of a solid formulation, a semisolid formulation, a liquid formulation, or a gaseous formulation.

24. The composition of claim 23, wherein the composition comprises the compound, a pharmaceutically acceptable salt, ester, solvate, isomer thereof, any crystalline form or racemate of the foregoing, a metabolite form of the foregoing, or a mixture of the foregoing in an amount of 0.01-1000 mg.

25. A method for prophylactically treating or treating a NS5B polymerase mediated disease, a DNA polymerase mediated disease or a reverse transcriptase mediated disease, comprising administering to a subject in need thereof an effective amount of the compound of claim 9, a pharmaceutically acceptable salt, ester, solvate, isomer thereof, any crystalline form or racemate of the foregoing, a metabolite form of the foregoing, or a mixture of the foregoing.

26. A method for prophylactically treating or treating a NS5B polymerase mediated disease, a DNA polymerase mediated disease or a reverse transcriptase mediated disease, comprising administering to a subject in need thereof an effective amount of the pharmaceutical composition of claim 23.

27. A method for prophylactically treating or treating a viral disease or cancer, comprising administering to a subject in need thereof an effective amount of the compound of claim 9, a pharmaceutically acceptable salt, ester, solvate, isomer thereof, any crystalline form or racemate of the foregoing, a metabolite form of the foregoing, or a mixture of the foregoing, wherein the viral disease is preferably selected from the group consisting of viral hepatitis type A, viral hepatitis type B, viral hepatitis type C, influenza, herpes, and acquired immunodeficiency syndrome (AIDS).

28. A method for prophylactically treating or treating a viral disease or cancer, comprising administering to a subject in need thereof an effective amount of the pharmaceutical composition of claim 23, wherein the viral disease is preferably selected from the group consisting of viral hepatitis type A, viral hepatitis type B, viral hepatitis type C, influenza, herpes, and acquired immunodeficiency syndrome (AIDS).

* * * * *